United States Patent
Bremel et al.

(10) Patent No.: US 12,374,421 B2
(45) Date of Patent: *Jul. 29, 2025

(54) BIOINFORMATIC PROCESSES FOR DETERMINATION OF PEPTIDE BINDING

(71) Applicant: IOGENETICS, LLC, Madison, WI (US)

(72) Inventors: Robert D. Bremel, Hillpoint, WI (US); Jane Homan, Hillpoint, WI (US)

(73) Assignee: IOGENETICS, LLC, Madison, WI (US)

( * ) Notice: Subject to any disclaimer, the term of this patent is extended or adjusted under 35 U.S.C. 154(b) by 69 days.

This patent is subject to a terminal disclaimer.

(21) Appl. No.: 14/895,746

(22) PCT Filed: Jun. 9, 2014

(86) PCT No.: PCT/US2014/041523
§ 371 (c)(1),
(2) Date: Dec. 3, 2015

(87) PCT Pub. No.: WO2014/200910
PCT Pub. Date: Dec. 18, 2014

(65) Prior Publication Data
US 2016/0132631 A1    May 12, 2016

Related U.S. Application Data

(60) Provisional application No. 61/833,248, filed on Jun. 10, 2013.

(51) Int. Cl.
G16B 5/00 (2019.01)
A61K 39/00 (2006.01)
(Continued)

(52) U.S. Cl.
CPC ............. *G16B 5/00* (2019.02); *A61K 39/098* (2013.01); *C07K 7/06* (2013.01); *C07K 7/08* (2013.01);
(Continued)

(58) Field of Classification Search
CPC .. A61K 39/098; A61K 2039/572; C07K 7/06; C07K 7/08; C12N 9/0051; G06F 17/16
See application file for complete search history.

(56) References Cited

U.S. PATENT DOCUMENTS 7,125,689 B2 * 10/2006 Carr ................... C07K 14/3153
435/69.1
2006/0257944 A1   11/2006 Fridman et al.
(Continued)

FOREIGN PATENT DOCUMENTS

WO     2011/119484     9/2011

OTHER PUBLICATIONS

Schneider et al. Proc. Natl. Acad. Sci. USA vol. 95, pp. 12179-12184, 1998.*

(Continued)

*Primary Examiner* — Karlheinz R. Skowronek
*Assistant Examiner* — Emilie A Neulen
(74) *Attorney, Agent, or Firm* — Casimir Jones, S.C.; J. Mitchell Jones

(57) ABSTRACT

This invention relates to the identification of peptide binding to ligands, and in particular to identification of epitopes expressed by microorganisms and by mammalian cells. The present invention provides polypeptides comprising the epitopes, and vaccines, antibodies and diagnostic products that utilize or are developed using the epitopes.

11 Claims, 23 Drawing Sheets

Specification includes a Sequence Listing.

(51) Int. Cl.
*A61K 39/02* (2006.01)
*C07K 7/06* (2006.01)
*C07K 7/08* (2006.01)
*C12N 9/02* (2006.01)
*G06F 17/16* (2006.01)
*G16B 20/00* (2019.01)
*G16B 20/30* (2019.01)
*G16B 20/50* (2019.01)
*G16B 40/00* (2019.01)
*G16B 40/20* (2019.01)

(52) U.S. Cl.
CPC ............ *C12N 9/0051* (2013.01); *G06F 17/16* (2013.01); *G16B 20/00* (2019.02); *G16B 20/30* (2019.02); *G16B 20/50* (2019.02); *G16B 40/00* (2019.02); *G16B 40/20* (2019.02); *A61K 2039/572* (2013.01); *C12Y 108/00* (2013.01)

(56) References Cited

U.S. PATENT DOCUMENTS

2007/0060518 A1* 3/2007 Liu ............... A61K 39/0008
530/327
2013/0123181 A1 5/2013 Pratt et al.
2013/0330335 A1* 12/2013 Bremel ............... G06F 19/18
424/134.1

OTHER PUBLICATIONS

Bremel et al. Immunome Res 6, 7, 1-15, 2010.*
Burden et al. Journal of Molecular Graphics and Modelling, 2005, 23, p. 481-489.*
Sette et al. Current Opinion in Immunology,2003,15:461-470.*
Irini A. Doytchinova et al.; Coupling In Silico and In Vitro Analysis of Peptide-MHC Binding: A Bioinformatic Approach Enabling Prediction of Superbinding Peptides and Anchorless Epitopes. J Immunol Jun. 15, 2004; 172 (12): 7495-7502. https://doi.org/10.4049/jimmunol.172.12.7495 (Year: 2004).*
Stevanović, S., Lemmel, C., Hantschel, M. and Eberle, U. (2003). Generating Data for Databases—The Peptide Repertoire of HLA Molecules. In Immunoinformatics: Bioinformatic Strategies for Better Understanding of Immune Function (eds Novartis Foundation, G. Bock and J. Goode). (Year: 2003).*
International Search Report & Written Opinion, International Patent Application No. PCT/US2014/041523, mailed Jan. 5, 2015.
Zhao et al. "Enhancing cytotoxic T cell repsonses with altered-peptide ligands" Arch Immunol Ther Exp 2001 vol. 49, No. 4, pp. 271-277.

* cited by examiner 10,000 random peptides

Figure 3 (Cont.)
Best peptides

```
5' TTCCCCGACGGCcctcctcgtccgacoggcaaaagatactgcatcaactcagcatccttgtccttcactcctgcagacCGCATGGAGGCCGAG
    F  P  D  G  P  P  R  P  T  G  K  R  Y  C  I  N  S  A  S  L  S  F  T  P  A  D  R  M  E  A  E
```

BIOINFORMATIC PROCESSES FOR DETERMINATION OF PEPTIDE BINDING

FIELD OF THE INVENTION

This invention relates to the identification of peptide binding to ligands, and in particular to identification of epitopes in proteins expressed by microorganisms and by mammalian cells.

BACKGROUND OF THE INVENTION

Infectious diseases, including some once considered to be controlled by antibiotics and vaccines, continue to be an important cause of mortality worldwide. Currently infectious and parasitic diseases account for over 15% of deaths worldwide and are experiencing a resurgence as a result of increasing antimicrobial drug resistance and as a secondary complication of HIV AIDS. (World Health Organization, Global Burden of Disease 2004). The field of reverse vaccinology adopts the approach of starting with the genome and identifying open reading frames and proteins which are suitable vaccine components and then testing their B-cell immunogenicity (Musser, J. M. 2006. Nat. Biotechnol. 24:157-158; Serruto, D., L. et al. 2009. Vaccine 27:3245-3250). Reverse vaccinology is an extraordinarily powerful approach, with potential to enable rapid identification of proteins with potential epitopes in silico from organisms for which a genome is available, whether or not the organism can be easily cultured in vitro. Diversity is a feature of all microbial species and most microbial species are represented in nature by many similar but non-identical strains some of which have acquired or lost metabolic traits such as growth characteristics, or antibiotic resistance. In some cases different isolates are antigenically different and do not offer cross protection to a subsequent infection with a different strain. The degree of variability between strains varies from one organism to another. Among the most variable are RNA viruses (e.g., but not limited to foot and mouth disease, influenza virus, rotavirus) which undergo constant mutation and exhibit constant antigenic drift posing a challenge to vaccine selection. Hence among the challenges to epitope mapping is to identify MHC high affinity binding peptides and B-cell epitope sequences which are conserved between multiple strains.

Vaccine development is not limited to those for infectious diseases. In Europe and America, cancer vaccine therapies are being developed, wherein cytotoxic T-lymphocytes inside the body of a cancer patient are activated by the administration of a tumor antigen. Results from clinical studies have been reported for some specific tumor antigens. However, when the diversity of cancers is considered, it is impossible to treat all cancers using a cancer vaccine consisting of only one type of tumor antigen. The diversity of cancer cells gives rise to diversity in the type or the amount of tumor antigens being expressed in the cancer cells. These antigens must be identified in order to develop therapies. What is needed are new and more efficient methods of identifying epitopes for use in developing vaccines, diagnostics, and therapeutics.

In some instances, disease can arise from an immune reaction directed to the body's own cells, known as autoimmunity. Autoimmunity can arise in a number of situations including, but not limited to a failure in development of tolerance, exposure of an epitope normally shielded from the immune surveillance, or as a secondary effect to exposure to an exogenous antigen which closely resembles or mimics the host cell in MHC or B cell binding characteristics. A growing number of autoimmune diseases are being identified as sequelae to exposure to epitopes in infectious agents which have mimics in the host tissues.

Brucellosis remains the most prevalent zoonosis worldwide and has its highest prevalence across North Africa, Middle East and Central Asia. Brucellosis is a debilitating chronic disease for people naturally infected through exposure to bacteria in milk and placental fluids of livestock. No effective vaccine exists to protect humans from brucellosis. Several weeks of antibiotic treatment are required, but may be unable to clear residual foci of bacteria. Historically, vaccines developed to control disease in cattle, sheep, and goats, the main natural reservoir, are comprised of live attenuated *Brucella* organisms, still capable of causing disease in humans and in livestock if incorrectly applied. Killed organisms are ineffective vaccines. A safe and effective vaccine is needed for veterinary use, and for prevention and potentially therapeutic use in humans.

The immune response is the consequence of many input signals including binding of epitopes to B cell receptors to initiate antibody production and the binding of peptides to MHC molecules within antigen presenting cells as pMHC complexes which are presented on the surface of antigen presenting cells to T cells, initiating a cellular response involving cytotoxic T cells and T helper cells which mediate both antibody production and cytotoxic T cell responses. Binding of the peptides to MHC molecules is a key step in the initiation of the immune response and is dependent on the genetics of the host. A short peptide may bind in either an N—C orientation or in a C—N orientation when present in a complex with an MHC groove.

A mathematical approach to further understanding of the structurally-based peptide binding mechanisms involved in immunologic and other protein based reactions and which can be implemented in silico would be of great value to the art.

Beyond the understanding of epitope structure and binding for the purposes of developing vaccines and biotherapeutics there is a broader need to be able to characterize protein interactions in binding reactions, including but not limited to enzymatic reactions, binding of ligands to cell receptors and other physiologic mechanisms.

SUMMARY OF THE INVENTION

The present invention is directed to the identification of immunogenic epitopes and the design and expression of peptides comprising epitopes with specific characteristics. It is further directed to methods for identifying and designing such epitopes and peptides comprising such epitopes. The present invention is also directed to the definition of certain antigens epitopes and peptides comprising these in *Brucella* spp. bacteria.

In some embodiments the present invention provides synthetic amino acid sequences which have been modified to increase or decrease their binding to one or more MHC molecules. In some embodiments the modifications may change the binding to one MHC allele molecule, whereas in others the changes may impact the binding to up to five different MHC allele molecules. The changes in the amino acid sequence implemented by the present invention may bring about a change of >1 or >2 standard deviation units in the relative binding affinity of a peptide to a particular MHC molecules. In some embodiments such change in binding affinity may result in higher affinity binding whereas in other embodiments it leads to a reduced binding affinity. The present invention in some embodiments, is applicable to MHC I alleles, whereas in other embodiments it is applicable to MHC II alleles. The changes in binding affinity may be the result of changes in the central core of the binding peptide or may be in the peripheral amino acids.

The present invention, which allows changes in MHC binding affinity to be introduced into peptides, may be applied to any protein, including but not limited to, from a plant protein, mammalian protein, a microbial protein, a viral protein, an allergen, an immunoglobulin, and a tumor associated antigen. In yet other embodiments the changes may be implemented in a biopharmaceutical protein, including but not limited to, a therapeutic drug protein and a vaccine.

The goals of the modifications to binding affinity implemented by the present invention may be, in one embodiment to increase the antigenicity and elicit an upregulation of the immune response, or, in the alternative, to cause a greater degree of immunosuppression or tolerization.

The present invention provides a computer implemented process for selecting amino acid changes which will specifically increase or decrease the MHC binding affinity. In some embodiments said computer implemented process involves initially developing a mathematical expression which serves as a descriptor of a peptide. Said mathematical expression is derived from multiple physical parameters of the amino acids making up the peptide. In some specific embodiments said descriptors comprise multiple principal components of the amino acid physical parameters, providing ranked and weighted uncorrelated proxies for the variance in the amino acids. Said mathematical descriptors are compared to experimentally derived datasets of peptide-MHC binding to derive predictive equations which may be applied to peptides from other proteins. In some embodiments the comparison is affected by least squares regression and is conducted by application of a neural net. In yet other embodiments the comparison may be made by application of other machine learning tools such as a support vector machine; however the choice of comparative method is not limiting. In particular embodiments the present invention can then be used to conduct simulation analyses to compare the impact on predicted binding of the substitution of various amino acids at any peptide position in order to select a change which increases or decreases predictive binding affinity. While in some specific embodiments of the present invention is directed to binding between a peptide and its ligand in the MHC molecules, it is understood that the same simulative process could be applied to other peptide ligand binding relationships and thus references to epitopes and MHC molecule binding should not be considered limiting. In some specific embodiments the simulation process may be applied to multiple amino acid sequences and may generate predictions for multiple MHC molecules. The changes predicted may be from the substitution of one or more than one amino acid. In some specific embodiments of the present invention the change in peptide ligand binding affinity may be brought about by the introduction of variant amino acids, not found within the usual 20 amino acids typically found in natural proteins.

In a previously described approach to prediction of peptide ligand binding (see, e.g., PCT/US2011/029192, incorporated by reference herein its entirety) the computer implemented description of peptides and the comparison of binding relative to a training set in order to develop predictive equations was described by reference to the sequence of amino acids in a protein processed from a starting point at the N terminal end of a peptide and progressing towards the C terminal end of the peptide. In the present invention we now provide a method of analysis of peptides which may be bound to their ligands in a reverse orientation, starting at the C terminal end and progressing to the N terminal end. This particular embodiment accounts for the situation in a peptide MHC binding relationship where the two binding partners are lying in opposite orientations to each other.

The frequent occurrence of B cell epitopes and MHC binding peptides in proximity to each other has been previously described (Bremel R D, Homan E J, 2013, Recognition of higher order patterns in proteins: immunologic kernels PLOS One. July 29;8 (7): e70115 and PCT/US2011/029192, incorporated by reference herein its entirety)). In one particular embodiment the present invention provides a means of locating a peptide sequence which comprises high affinity MHC binding peptides, by reference to an identified B cell linear epitope.

In some embodiments the present invention provides a means of identifying in a protein those specific peptide sequences which comprise a B cell binding epitope or antibody binding epitope but which are lacking in any high affinity MHC-binding peptides in the immediate proximity. In a particular embodiment this invention therefore enables the selection of peptides for inclusion in a vaccine intended to elicit an antibody response but not a cell mediated response. Conversely in yet another embodiment the invention allows the selection of peptides which will elicit a cell mediated response due to the presence of MHC binding peptides but will not elicit an antibody response due to the absence of B cell epitopes. Yet again this provides a tool for the design of vaccines in which specific categories of immune response are desired. In some specific embodiments the desired outcome may be to elicit and increased immune upregulation while in yet other embodiments the desired outcome is to increase down regulation or immunosuppression.

The present invention provides for the identification of epitopes and epitope dense regions in the proteins of *Brucella* species bacteria. In some embodiments the invention provides for the description and synthesis of a polypeptide comprising a B cell epitope and an overlapping or immediately adjacent MHC binding peptide derived from *Brucella* spp. In some particular embodiments the MHC binding peptide as and MHC I binding peptide whereas in others it is an MHC II binding peptide. In particular embodiments the aforementioned epitope peptides from *Brucella* spp bind with an affinity from the group of about greater than $10^6$ $M^{-1}$, about greater than $10^7 M^{-1}$, about greater than $10^8 M^{-1}$, and about greater than $10^9 M^{-1}$ The binding affinity may be to one or many MHC binding regions. In some particular embodiments the peptides identified as having binding affinity to B cell receptors and to MHC molecules and which are derived from *Brucella* spp are conserved across many isolates or strains of *Brucella* and said *Brucella* may be of several species including but not limited to *Brucella melitensis, Brucella abortus, Brucella suis, Brucella canis* and other species of the same genus. In particular embodiments the sequences of such peptide sequences comprising B cell epitopes and MHC binding of high affinity are provided. Other embodiments provide for the nucleic acid encoding said sequences or the said *Brucella* sequence encoded in a genetic vector, or expressed by a host cell. Having described the epitope peptides within *Brucella* the invention further describes antibodies and B cells which bid to said epitopes and various fusion products of said epitope and antibody to said epitope. By providing sequences containing the conserved epitope sequences of *Brucella* the present invention provides the constituents of a vaccine directed to protect from or to enhance recovery for brucellosis and various compositions therefor. In some embodiments the present invention provides the epitope constituents of a vaccine for human use against brucellosis; in yet other embodiments the invention provides the constituents for a vaccine for use in animals against brucellosis. It further provides the constituents of immunogens which may be used to direct the production of an antibody and to prepare a diagnostic array for detection of *Brucella* infection.

DESCRIPTION OF THE FIGURES

Figure 15:
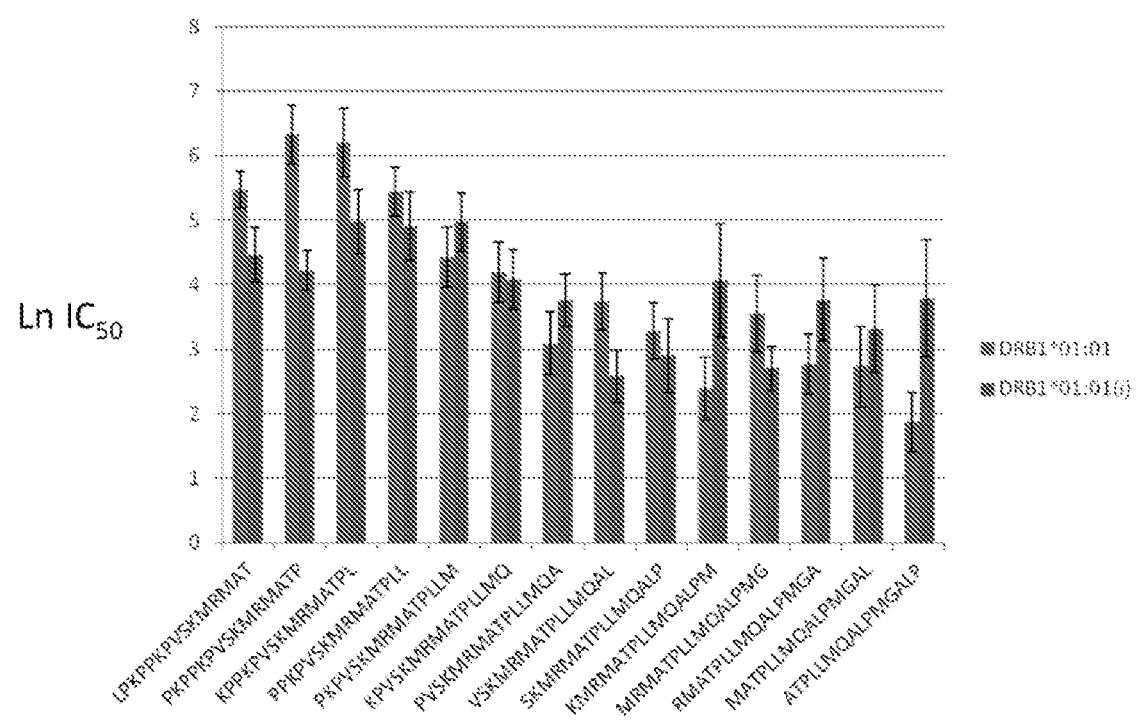

FIG. 15 shows the predicted MHC affinity for CLIP peptide in either the canonical orientation or the reverse orientation in binding groove DR1 (DRB1*01:01).

FIG. 20 shows altered flanking regions of RL9 peptide.

DEFINITIONS

Figure 1:
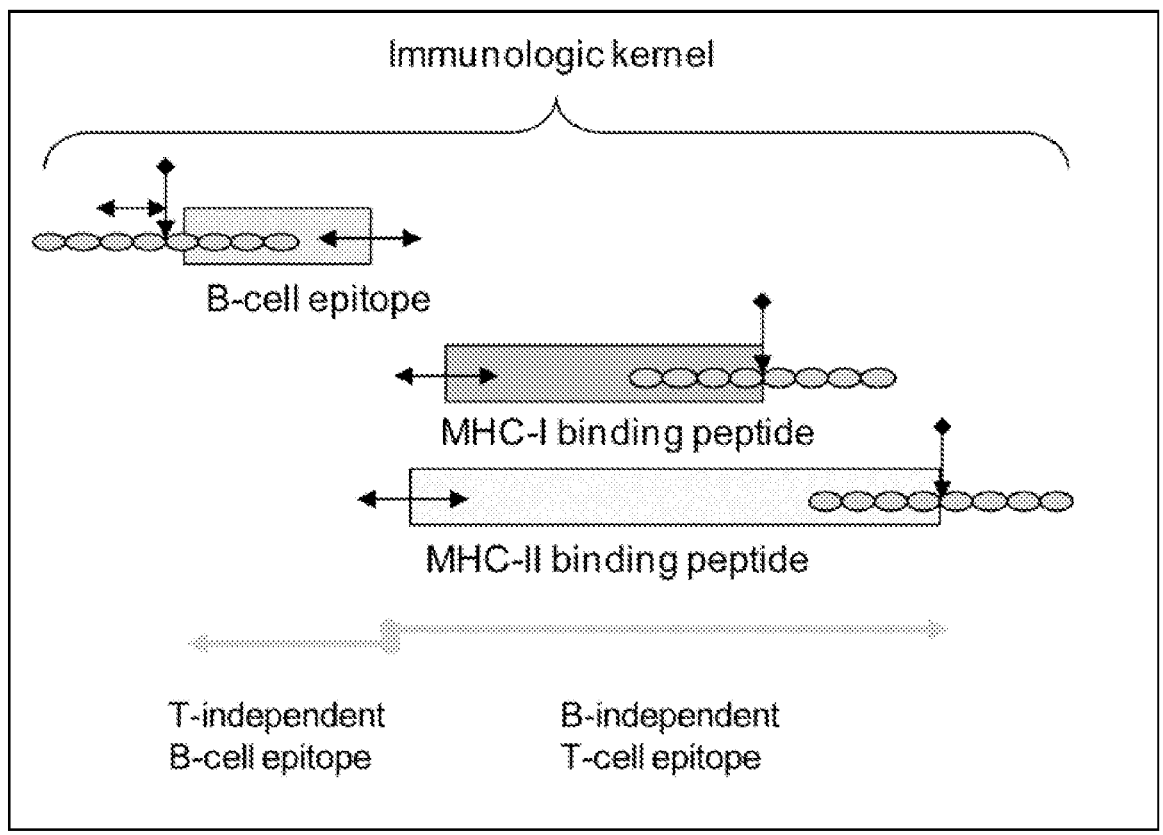
FIG. 1 shows the higher order relationship of B cell epitope, MHC binding and cathepsin cleavage as an "immunological kernel"

As used herein, the term "genome" refers to the genetic material (e.g., chromosomes) of an organism or a host cell.

As used herein, the term "proteome" refers to the entire set of proteins expressed by a genome, cell, tissue or organism. A "partial proteome" refers to a subset the entire set of proteins expressed by a genome, cell, tissue or organism. Examples of "partial proteomes" include, but are not limited to, transmembrane proteins, secreted proteins, and proteins with a membrane motif.

As used herein, the terms "protein," "polypeptide," and "peptide" refer to a molecule comprising amino acids joined via peptide bonds. In general, "peptide" is used to refer to a sequence of 20 or less amino acids and "polypeptide" is used to refer to a sequence of greater than 20 amino acids.

As used herein, the term, "synthetic polypeptide," "synthetic peptide" and "synthetic protein" refer to peptides, polypeptides, and proteins that are produced by a recombinant process (i.e., expression of exogenous nucleic acid encoding the peptide, polypeptide or protein in an organism, host cell, or cell-free system) or by chemical synthesis.

As used herein, the term "protein of interest" refers to a protein encoded by a nucleic acid of interest.

As used herein, the term "native" (or wild type) when used in reference to a protein refers to proteins encoded by the genome of a cell, tissue, or organism, other than one manipulated to produce synthetic proteins.

As used herein, the term "B-cell epitope" refers to a polypeptide sequence that is recognized and bound by a B-cell receptor. A B-cell epitope may be a linear peptide or may comprise several discontinuous sequences which together are folded to form a structural epitope. Such component sequences which together make up a B-cell epitope are referred to herein as B-cell epitope sequences. Hence, a B cell epitope may comprise one or more B-cell epitope sequences. A B cell epitope is also specifically bound by antibody produced by the same B cell.

As used herein, the term "predicted B-cell epitope" refers to a polypeptide sequence that is predicted to bind to a B-cell receptor by a computer program, for example, in addition to methods described herein, Bepipred (Larsen, et al., Immunome Research 2:2, 2006) and others as referenced by Larsen et al. (ibid) (Hopp T et al PNAS 78:3824-3828, 1981; Parker J et al, Biochem. 25:5425-5432, 1986). A predicted B-cell epitope may refer to the identification of B-cell epitope sequences forming part of a structural B-cell epitope or to a complete B-cell epitope.

As used herein, the term "T-cell epitope" refers to a polypeptide sequence bound to a major histocompatibility protein molecule in a configuration recognized by a T-cell receptor. Typically, T-cell epitopes are presented on the surface of an antigen-presenting cell.

As used herein, the term "predicted T-cell epitope" refers to a polypeptide sequence that is predicted to bind to a major histocompatibility protein molecule by the neural network (NN) algorithms described herein or as determined experimentally.

As used herein the terms "canonical" and "non-canonical" are used to refer to the orientation of an amino acid sequence. Canonical refers to an amino acid sequence presented or read in the N terminal to C terminal order; non-canonical is used to describe an amino acid sequence presented in the inverted or C terminal to N terminal order.

As used herein, the term "major histocompatibility complex (MHC)" refers to the MHC Class I and MHC Class II genes and the proteins encoded thereby. Molecules of the MHC bind small peptides and present them on the surface of cells for recognition by T-cell receptor-bearing T-cells. The MHC is both polygenic (there are several MHC class I and MHC class II genes) and polymorphic (there are multiple alleles of each gene). The terms MHC-I, MHC-II, MHC-1 and MHC-2 are variously used herein to indicate these classes of molecules. Included are both classical and non-classical MHC molecules. An MHC molecule is made up of multiple chains (alpha and beta chains) which associate to form a molecule. The MHC molecule contains a cleft which forms a binding site for peptides. Peptides bound in the cleft may then be presented to T-cell receptors. The term "MHC binding region" refers to the cleft region of the MHC molecule where peptide binding occurs.

As used herein, the term "haplotype" refers to the HLA alleles found on one chromosome and the proteins encoded thereby. Haplotype may also refer to the allele present at any one locus within the MHC. Each class of MHC is represented by several loci: e.g., HLA-A (Human Leukocyte Antigen-A), HLA-B, HLA-C, HLA-E, HLA-F, HLA-G, HLA-H, HLA-J, HLA-K, HLA-L, HLA-P and HLA-V for class I and HLA-DRA, HLA-DRB1-9, HLA-, HLA-DQA1, HLA-DQB1, HLA-DPA1, HLA-DPB1, HLA-DMA, HLA-DMB, HLA-DOA, and HLA-DOB for class II. The terms "HLA allele" and "MHC allele" are used interchangeably herein. HLA alleles are listed at hla.alleles.org/nomenclature/naming.html, which is incorporated herein by reference.

The MHCs exhibit extreme polymorphism: within the human population there are, at each genetic locus, a great number of haplotypes comprising distinct alleles—the IMGT/HLA database release (February 2010) lists 948 class I and 633 class II molecules, many of which are represented at high frequency (>1%). MHC alleles may differ by as many as 30-aa substitutions. Different polymorphic MHC alleles, of both class I and class II, have different peptide specificities: each allele encodes proteins that bind peptides exhibiting particular sequence patterns.

The naming of new HLA genes and allele sequences and their quality control is the responsibility of the WHO Nomenclature Committee for Factors of the HLA System, which first met in 1968, and laid down the criteria for successive meetings. This committee meets regularly to discuss issues of nomenclature and has published 19 major reports documenting firstly the HLA antigens and more recently the genes and alleles. The standardization of HLA antigenic specifications has been controlled by the exchange of typing reagents and cells in the International Histocompatibility Workshops. The IMGT/HLA Database collects both new and confirmatory sequences, which are then expertly analyzed and curated before been named by the Nomenclature Committee. The resulting sequences are then included in the tools and files made available from both the IMGT/HLA Database and at hla.alleles.org.

Each HLA allele name has a unique number corresponding to up to four sets of digits separated by colons. See e.g., hla.alleles.org/nomenclature/naming.html which provides a description of standard HLA nomenclature and Marsh et al., Nomenclature for Factors of the HLA System, 2010 Tissue Antigens 2010 75:291-455. HLA-DRB1*13:01 and HLA-DRB1*13:01:01:02 are examples of standard HLA nomenclature. The length of the allele designation is dependent on the sequence of the allele and that of its nearest relative. All alleles receive at least a four digit name, which corresponds to the first two sets of digits, longer names are only assigned when necessary.

The digits before the first colon describe the type, which often corresponds to the serological antigen carried by an allotype, The next set of digits are used to list the subtypes, numbers being assigned in the order in which DNA sequences have been determined. Alleles whose numbers differ in the two sets of digits must differ in one or more nucleotide substitutions that change the amino acid sequence of the encoded protein. Alleles that differ only by synonymous nucleotide substitutions (also called silent or non-coding substitutions) within the coding sequence are distinguished by the use of the third set of digits. Alleles that only differ by sequence polymorphisms in the introns or in the 5' or 3' untranslated regions that flank the exons and introns are distinguished by the use of the fourth set of digits. In addition to the unique allele number there are additional optional suffixes that may be added to an allele to indicate its expression status. Alleles that have been shown not to be expressed, 'Null' alleles have been given the suffix 'N'. Those alleles which have been shown to be alternatively expressed may have the suffix 'L', 'S', 'C', 'A' or 'Q'. The suffix 'L' is used to indicate an allele which has been shown to have 'Low' cell surface expression when compared to normal levels. The 'S' suffix is used to denote an allele specifying a protein which is expressed as a soluble 'Secreted' molecule but is not present on the cell surface. A 'C' suffix to indicate an allele product which is present in the 'Cytoplasm' but not on the cell surface. An 'A' suffix to indicate 'Aberrant' expression where there is some doubt as to whether a protein is expressed. A 'Q' suffix when the expression of an allele is 'Questionable' given that the mutation seen in the allele has previously been shown to affect normal expression levels.

In some instances, the HLA designations used herein may differ from the standard HLA nomenclature just described due to limitations in entering characters in the databases described herein. As an example, DRB1_0104, DRB1*0104, and DRB1-0104 are equivalent to the standard nomenclature of DRB1*01:04. In most instances, the asterisk is replaced with an underscore or dash and the semicolon between the two digit sets is omitted.

As used herein, the term "polypeptide sequence that binds to at least one major histocompatibility complex (MHC) binding region" refers to a polypeptide sequence that is recognized and bound by one more particular MHC binding regions as predicted by the neural network algorithms described herein or as determined experimentally.

As used herein, the term "T independent B cell epitope" means a polypeptide which comprises a B cell receptor-binding or antibody-binding peptide, but in which a high affinity MHC binding peptide is absent within 35 amino acids of the margins of said B cell binding or antibody binding peptide.

As used herein the term "B-independent T cell epitope" means a polypeptide which comprises a peptide which binds with high affinity to a MHC molecule but which has no B cell or antibody binding peptides within 35 amino acids of the margins of said MHC binding peptide.

As used herein, the term "allergen" refers to an antigenic substance capable of producing immediate hypersensitivity and includes both synthetic as well as natural immunostimulant peptides and proteins.

As used herein, the term "transmembrane protein" refers to proteins that span a biological membrane. There are two basic types of transmembrane proteins. Alpha-helical proteins are present in the inner membranes of bacterial cells or the plasma membrane of eukaryotes, and sometimes in the outer membranes. Beta-barrel proteins are found only in outer membranes of Gram-negative bacteria, cell wall of Gram-positive bacteria, and outer membranes of mitochondria and chloroplasts.

As used herein, the term "external loop portion" refers to the portion of transmembrane protein that is positioned between two membrane-spanning portions of the transmembrane protein and projects outside of the membrane of a cell.

As used herein, the term "tail portion" refers to refers to an n-terminal or c-terminal portion of a transmembrane protein that terminates in the inside ("internal tail portion") or outside ("external tail portion") of the cell membrane.

As used herein, the term "secreted protein" refers to a protein that is secreted from a cell.

As used herein, the term "membrane motif" refers to an amino acid sequence that encodes a motif not a canonical transmembrane domain but which would be expected by its function deduced in relation to other similar proteins to be located in a cell membrane, such as those listed in the publicly available psortb database.

As used herein, the term "consensus protease cleavage site" refers to an amino acid sequence that is recognized by a protease such as trypsin or pepsin.

As used herein, the term "affinity" refers to a measure of the strength of binding between two members of a binding pair, for example, an antibody and an epitope and an epitope and a MHC-I or II haplotype. $K_d$ is the dissociation constant and has units of molarity. The affinity constant is the inverse of the dissociation constant. An affinity constant is sometimes used as a generic term to describe this chemical entity. It is a direct measure of the energy of binding. The natural logarithm of K is linearly related to the Gibbs free energy of binding through the equation $\Delta G_0 = -RT\ LN(K)$ where R=gas constant and temperature is in degrees Kelvin. Affinity may be determined experimentally, for example by surface plasmon resonance (SPR) using commercially available Biacore SPR units (GE Healthcare) or in silico by methods such as those described herein in detail.

Affinity may also be expressed as the ic50 or inhibitory concentration 50, that concentration at which 50% of the peptide is displaced. Likewise ln(ic50) refers to the natural log of the ic50.

The term "$K_{off}$", as used herein, is intended to refer to the off rate constant, for example, for dissociation of an antibody from the antibody/antigen complex, or for dissociation of an epitope from an MHC haplotype.

The term "$K_d$", as used herein, is intended to refer to the dissociation constant (the reciprocal of the affinity constant "Ka"), for example, for a particular antibody-antigen interaction or interaction between an epitope and an MHC haplotype.

As used herein, the terms "strong binder" and "strong binding" refer to a binding pair or describe a binding pair that have an affinity of greater than $2 \times 10^7 M^{-1}$ (equivalent to a dissociation constant of 50 nM Kd)

As used herein, the term "moderate binder" and "moderate binding" refer to a binding pair or describe a binding pair that have an affinity of from $2 \times 10^7 M^{-1}$ to $2 \times 10^6 M^{-1}$.

As used herein, the terms "weak binder" and "weak binding" refer to a binding pair or describe a binding pair that have an affinity of less than $2 \times 10^6 M^{-1}$ (equivalent to a dissociation constant of 500 nM Kd)

The terms "specific binding" or "specifically binding" when used in reference to the interaction of an antibody and a protein or peptide or an epitope and an MHC haplotype means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the term "antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc. Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]). In other embodiments, suitable monoclonal antibodies, including recombinant chimeric monoclonal antibodies and chimeric monoclonal antibody fusion proteins are prepared as described herein.

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen-binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "support vector machine" refers to a set of related supervised learning methods used for classification and regression. Given a set of training examples, each marked as belonging to one of two categories, an SVM training algorithm builds a model that predicts whether a new example falls into one category or the other.

As used herein, the term "classifier" when used in relation to statistical processes refers to processes such as neural nets and support vector machines.

As used herein "neural net", which is used interchangeably with "neural network" and sometimes abbreviated as NN, refers to various configurations of classifiers used in machine learning, including multilayered perceptrons with one or more hidden layer, support vector machines and dynamic Bayesian networks. These methods share in common the ability to be trained, the quality of their training evaluated and their ability to make either categorical classifications or of continuous numbers in a regression mode.

Perceptron as used herein is a classifier which maps its input x to an output value which is a function of x, or a graphical representation thereof.

As used herein "recursive partitioning" or "recursive partitioning algorithm" refers to a statistical method for multivariable analysis. Recursive partitioning operates through a decision tree that strives to correctly classify members of the population based on several dichotomous dependent variables.

As used herein, the term "principal component analysis" refers to a mathematical process which reduces the dimensionality of a set of data (Wold, S., Sjorstrom, M., and Eriksson, L., Chemometrics and Intelligent Laboratory Systems 2001. 58: 109-130; Multivariate and Megavariate Data Analysis Basic Principles and Applications (Parts I&II) by L. Eriksson, E. Johansson, N. Kettaneh-Wold, and J. Trygg, 2006 $2^{nd}$ Edit. Umetrics Academy). Derivation of principal components is a linear transformation that locates directions of maximum variance in the original input data, and rotates the data along these axes. For n original variables, n principal components are formed as follows: The first principal component is the linear combination of the standardized original variables that has the greatest possible variance. Each subsequent principal component is the linear combination of the standardized original variables that has the greatest possible variance and is uncorrelated with all previously defined components. Further, the principal components are scale-independent in that they can be developed from different types of measurements.

As used herein, the term "vector" when used in relation to a computer algorithm or the present invention, refers to the mathematical properties of the amino acid sequence.

As used herein, the term "vector," when used in relation to recombinant DNA technology, refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors.

As used herein, the terms "biocide" or "biocides" refer to at least a portion of a naturally occurring or synthetic molecule (e.g., peptides or enzymes) that directly kills or promotes the death and/or attenuation of (e.g., prevents growth and/or replication) of biological targets (e.g., bacteria, parasites, yeast, viruses, fungi, protozoas and the like). Examples of biocides include, but are not limited to, bactericides, viricides, fungicides, parasiticides, and the like.

As used herein, the terms "protein biocide" and "protein biocides" refer to at least a portion of a naturally occurring or synthetic peptide molecule or enzyme that directly kills or promotes the death and/or attenuation of (e.g., prevents growth and/or replication) of biological targets (e.g., bacteria, parasites, yeast, viruses, fungi, protozoas and the like). Examples of biocides include, but are not limited to, bactericides, viricides, fungicides, parasiticides, and the like.

As used herein, the term "neutralization," "pathogen neutralization," "and spoilage organism neutralization" refer to destruction or inactivation (e.g., loss of virulence) of a "pathogen" or "spoilage organism" (e.g., bacterium, parasite, virus, fungus, mold, prion, and the like) thus preventing the pathogen's or spoilage organism's ability to initiate a disease state in a subject or cause degradation of a food product.

As used herein, the term "spoilage organism" refers to microorganisms (e.g., bacteria or fungi), which cause degradation of the nutritional or organoleptic quality of food and reduces its economic value and shelf life. Exemplary food spoilage microorganisms include, but are not limited to, *Zygosaccharomyces bailii, Aspergillus niger, Saccharomyces cerivisiae, Lactobacillus plantarum, Streptococcus faecalis,* and *Leuconostoc mesenteroides.*

As used herein, the term "microorganism targeting molecule" refers to any molecule (e.g., protein) that interacts with a microorganism. In preferred embodiments, the microorganism targeting molecule specifically interacts with microorganisms at the exclusion of non-microorganism host cells. Preferred microorganism targeting molecules interact with broad classes of microorganism (e.g., all bacteria or all gram positive or negative bacteria). However, the present invention also contemplates microorganism targeting molecules that interact with a specific species or sub-species of microorganism. In some preferred embodiments, microorganism targeting molecules interact with "Pathogen Associated Molecular Patterns (PAMPS)". In some embodiments, microorganism targeting molecules are recognition molecules that are known to interact with or bind to PAMPS (e.g., including, but not limited to, as CD14, lipopolysaccharide binding protein (LBP), surfactant protein D (SP-D), and Mannan binding lectin (MBL)). In other embodiments, microorganism targeting molecules are antibodies (e.g., monoclonal antibodies directed towards PAMPS or monoclonal antibodies directed to specific organisms or serotype specific epitopes).

As used herein the term "biofilm" refers to an aggregation of microorganisms (e.g., bacteria) surrounded by an extracellular matrix or slime adherent on a surface in vivo or ex vivo, wherein the microorganisms adopt altered metabolic states.

As used herein, the term "host cell" refers to any eukaryotic cell (e.g., mammalian cells, avian cells, amphibian cells, plant cells, fish cells, insect cells, yeast cells), and bacteria cells, and the like, whether located in vitro or in vivo (e.g., in a transgenic organism).

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acids are nucleic acids present in a form or setting that is different from that in which they are found in nature. In contrast, non-isolated nucleic acids are nucleic acids such as DNA and RNA that are found in the state in which they exist in nature.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

A "subject" is an animal such as vertebrate, preferably a mammal such as a human, a bird, or a fish. Mammals are understood to include, but are not limited to, murines, simians, humans, bovines, cervids, equines, porcines, canines, felines etc.).

An "effective amount" is an amount sufficient to effect beneficial or desired results. An effective amount can be administered in one or more administrations, As used herein, the term "purified" or "to purify" refers to the removal of undesired components from a sample. As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

The terms "bacteria" and "bacterium" refer to prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., CV Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red. In some embodiments, the bacteria are those capable of causing disease (pathogens) and those that cause product degradation or spoilage.

"Strain" as used herein in reference to a microorganism describes an isolate of a microorganism (e.g., bacteria, virus, fungus, parasite) considered to be of the same species but with a unique genome and, if nucleotide changes are non-synonymous, a unique proteome differing from other strains of the same organism. Typically strains may be the result of isolation from a different host or at a different location and time but multiple strains of the same organism may be isolated from the same host.

"Anergy" as used herein refers to a lack of reaction by the body's immune system to foreign substances. In some embodiments, anergy comprises a direct induction of peripheral lymphocyte tolerance. In some embodiments, an individual in a state of anergy is unable to mount a normal immune response against a specific antigen.

As used herein "regulatory T cells" refers to a subpopulation of T cells which are immunosuppressive and down-regulate the immune system. T regulatory cells may function to maintain tolerance to self-antigens, and downregulate autoimmune disease. Regulatory T cells may be abbreviated herein as $T_{reg}$, or Treg.

As used herein "orthogonal" refers to a parameter or a mathematical expression which is statistically independent from another such parameter or mathematical expression. Hence orthogonal and uncorrelated are used interchangeably herein.

As used herein "bagging" which is an abbreviated term for "bootstrap aggregation" is used to describe a process whereby small, balanced subsets of data are selected randomly from a larger training dataset and processed, followed by processing of a further randomly selected subset of data from the same dataset. This cycle is repeated multiple times with different random subsets from the same dataset. This process is used for training and validation of the classifiers, then allowing the resulting predictors to be applied to larger datasets. For instance 5 k-fold cross validation may be performed 5 times, each time starting with a different seed for the random number generator.

As used herein "ensemble" is used to describe a collection of similar equations or computer processes each contributing to an overall analysis. In some instances an ensemble may be a series of predictive equations each focused on a prediction specific to a particular circumstance. Ensembles may be used as a form of analysis as a "committee" where a determination is based on the "vote" of each member of the ensemble. Thus if 8 of 10 equations predict outcome "A" and 2 of 10 predict outcome "not A" then a prediction of 0.8 probability of A is made As used herein the term "training set" refers to a database or large set of peptides for which experimental determinations of certain properties have been reported. Such properties may include but not be limited to binding affinity to ligands of interest such as MHC molecules, enzyme cleavage properties or any other such properties which may be measured in an experimental assay. A training set then is used as an input in developing predictions through a machine learning tool which may include a neural net or support vector machine among many non-limiting examples.

DETAILED DESCRIPTION OF THE INVENTION

The present invention describes specific novel applications of the mathematical analysis of binding which allow manipulation of the binding affinity to increase or decrease the antigenicity of a specific epitope. It further describes approaches to selection of epitopes with specific types of binding interaction. In yet further embodiments, the present invention describes application of binding analysis to *Brucella* species to identify epitopes with specific biding characteristics.

This invention further relates to the identification of peptide epitopes from proteomes of microorganisms and host cells. Such epitopes upon interacting with the immune system may elicit an upregulation or down regulation of the immune response. Once peptide epitopes are identified, they can be synthesized or produced as recombinant products (e.g., the epitope itself or a polypeptide or protein comprising the epitope) and utilized in vaccines, diagnostics or as targets of drug therapy. The accurate prediction of peptides which are epitopes for either B-cell or T-cell mediated immunity is thus an important step in providing, among other things: understanding of how the proteome is presented to, and processed by, the immune system; information enabling development of improved vaccines, biotherapeutics, diagnostics, and antimicrobial drugs; and methods of identifying targets on membrane proteins potentially useful to other areas of research. A computer implemented process for analysis of peptide binding and epitope identification has been previously described by the inventors (see, e.g., PCT/US2011/029192, incorporated by reference herein its entirety) but for reference is summarized below. The present invention addresses specific novel embodiments and applications of peptide epitope analysis.

Overview of Computer Implemented Process for Analysis of Peptide Binding

The field of bioinformatics has provided powerful tools to analyze large datasets arising from sequenced genomes, proteomes and transcriptomes. But often analysis of the proteomic information has been based on individual amino acids, using sequences, not segments, and without translation to structure, biological function and location of the proteins in the whole organism. The leading proponents of reverse vaccinology identify the challenge of the future as the integration of sequence-based prediction with structural information (Serruto and Rappuoli. 2006. FEBS Lett. 580: 2985-2992.)

For the reasons stated above there is a need for a method to identify peptide epitopes for both B and T-cell immunity which can enhance the development of vaccines, therapeutics and vaccines. The present invention provides methods of B-cell epitope prediction and MHC binding region prediction, together with the topological/protein structural considerations. It also provides an integrated approach and enables the management of peptide epitope analysis from a desktop computer in a familiar spreadsheet format.

Accordingly, in some embodiments, the present invention provides computer implemented processes of identifying ligands (e.g., peptides) that interact with a partner or substrate, e.g., other polypeptides, including but not limited to, B-cell receptors and antibodies, MHC-I and II binding regions, protein receptors, polypeptide domains such as binding domains and catalytic domains, organic molecules, aptamers, nucleic acids and the like. In some embodiments, the present invention provides computer implemented processes of describing peptides that interact with a partner or substrate by formulation of a mathematical expression that correlates to or applies one or more physical properties of amino acid within an amino acid subset and applies the mathematical expression to predict the interaction (e.g., binding) of the amino acids subset with the partner. In some embodiments, the present invention provides computer implemented processes of identifying peptides that interact with a partner or substrate that formulate a mathematical expression that correlates to or describes one or more physical properties of amino acids within an amino acid subset, substitutes the amino acids with the mathematical expression, and applies the mathematical expression to predict the interaction (e.g., binding) of the amino acid subset with the partner. In some embodiments, the present invention provides computer implemented processes of identifying peptides that interact with a partner or substrate that formulate a mathematical expression based on the principal components of physical properties of amino acids within an amino acid subset and applies the mathematical expression to predict the interaction (e.g., binding) of the amino acids subset with the partner. In some embodiments, the present invention provides computer implemented processes of identifying peptides that interact with a partner or substrate that formulate a mathematical expression based on the principal components of physical properties of amino acids within an amino acid subset and applies the mathematical expression to predict the interaction (e.g., binding) of the amino acids subset with the partner. In some embodiments, the present invention provides computer implemented processes of identifying peptides that interact with a partner or substrate that formulate a mathematical expression based on the principal components of physical properties of amino acids within an amino acid subset and applies the mathematical expression to predict the interaction (e.g., binding) of the amino acids subset with the partner using a trained neural network. In some embodiments, the present invention provides computer implemented processes of identifying peptides that interact with MHC binding region, B cell receptor, or antibody that formulate a mathematical expression based on the principal components of physical properties of amino acids within an amino acid subset and applies the mathematical expression to predict the interaction (e.g., binding) of the amino acids subset with the partner using a trained neural network, for example a neural network trained for peptide binding to one more MHC alleles or binding regions.

In some embodiments, the present invention comprises a computer implemented process comprising: in-putting an amino acid sequence from a target source into a computer; analyzing more than one physical parameter of subsets of amino acids in the sequence via a computer processor; deriving a mathematical expression to describe amino acid subsets. The descriptors of amino acid subsets, or peptides, are then compared with the experimentally determined binding reactions of a large set of peptides, known as a training set. In some embodiments the comparison is conducted through the application of least squares regression. In some embodiments this analysis is achieved through the application of a neural network. In yet other embodiments other machine learning tools may be applied, such as but not limited to, a support vector machine. Through this process a series of predictive equations are developed which may be applied to any peptide from any protein of interest, once said peptide is converted to a mathematical descriptor based on its physical parameters. The physicochemical properties derived in the studies used for this calculation are shown in Table

TABLE 1

| | | |
|---|---|---|
| 1 | Polarity. | Zimmerman, J. M., Eliezer, N., and Simha, R., J.Theor.Biol. 1968. 21: 170-201. |
| 2 | Polarity (p). | Grantham, R., Science 1974. 185: 862-864. |
| 3 | Optimized matching hydrophobicity (OMH). | Sweet, R. M. and Eisenberg, D., J.Mol.Biol. 1983. 171: 479-488. |
| 4 | Hydropathicity. | Kyte, J. and Doolittle, R. F.,. J.Mol.Biol. 1982. 157: 105-132. |
| 5 | Hydrophobicity (free energy of transfer to surface in kcal/mole). | Bull, H. B. and Breese, K., Arch.Biochem.Biophys. 1974. 161: 665-670. |
| 6 | Hydrophobicity scale based on free energy of transfer (kcal/mole). | Guy, H. R., Biophys.J. 1985. 47: 61-70. |
| 7 | Hydrophobicity (delta G1/2 cal) | Abraham, D. J. and Leo, A. J., Proteins 1987. 2: 130-152. |
| 8 | Hydrophobicity scale (contact energy derived from 3D data). | Miyazawa, S. and Jernigan, R. L., Macromolecules 1985. 18: 534-552. |
| 9 | Hydrophobicity scale (pi-r). | Roseman, M. A., J.Mol.Biol. 1988. 200: 513-522. |
| 10 | Molar fraction (%) of 2001 buried residues. | Janin, J., Nature 1979. 277: 491-492. |
| 11 | Proportion of residues 95% buried (in 12 proteins). | Chothia, C., J.Mol.Biol. 1976. 105: 1-12. |
| 12 | Free energy of transfer from inside to outside of a globular protein. | Janin, J., Nature 1979. 277: 491-492. |
| 13 | Hydration potential (kcal/mole) at 25C. | Wolfenden, R., Andersson, L., Cullis, P. M., and Southgate, C. C., Biochemistry 1981. 20: 849-855. |
| 14 | Membrane buried helix parameter. | Rao, M. J. K. and Argos, P., Biochim.Biophys.Acta 1986. 869: 197-214. |
| 15 | Mean fractional area loss (f) [average area buried/ standard state area]. | Rose, G. D., Geselowitz, A. R., Lesser, G. J., Lee, R. H., and Zehfus, M. H., Science 1985. 229: 834-838. |
| 16 | Average area buried on transfer from standard state to folded protein. | Rose, G. D., Geselowitz, A. R., Lesser, G. J., Lee, R. H., and Zehfus, M. H., Science 1985. 229: 834-838. |
| 17 | Molar fraction (%) of 3220 accessible residues. | Janin, J., Nature 1979. 277: 491-492. |
| 18 | Hydrophilicity. | Hopp, T. P., Methods Enzymol. 1989. 178: 571-585. |

TABLE 1-continued

| | | |
|---|---|---|
| 19 | Normalized consensus hydrophobicity scale. | Eisenberg, D., Schwarz, E., Komaromy, M., and Wall, R., J.Mol.Biol. 1984. 179: 125-142. |
| 20 | Average surrounding hydrophobicity. | Manavalan, P. and Ponnuswamy, P. K., Nature 1978. 275: 673-674. |
| 21 | Hydrophobicity of physiological L-alpha amino acids | Black, S. D. and Mould, D. R., Anal.Biochem. 1991. 193: 72-82 |
| 22 | Hydrophobicity scale (pi-r)2. | Fauchere, J. L., Charton, M., Kier, L. B., Verloop, A., and Pliska, V., Int.J.Pept.Protein Res. 1988. 32: 269-278. |
| 23 | Retention coefficient in HFBA. | Browne, C. A., Bennett, H. P., and Solomon, S., Anal.Biochem. 1982. 124: 201-208. |
| 24 | Retention coefficient in HPLC, pH 2.1. | Meek, J. L., Proc.Natl.Acad.Sci.U.S.A 1980. 77: 1632-1636. |
| 25 | Hydrophilicity scale derived from HPLC peptide retention times. | Parker, J. M., Guo, D., and Hodges, R. S., Biochemistry 1986. 25: 5425-5432. |
| 26 | Hydrophobicity indices at ph 7.5 determined by HPLC. | Cowan, R. and Whittaker, R. G., Pept.Res. 1990. 3: 75-80. |
| 27 | Retention coefficient in TFA | Browne, C. A., Bennett, H. P., and Solomon, S., Anal.Biochem. 1982. 124: 201-208. |
| 28 | Retention coefficient in HPLC, pH 7.4 | Meek, J. L., Proc.Natl.Acad.Sci.U.S.A 1980. 77: 1632-1636. |
| 29 | Hydrophobicity indices at pH 3.4 determined by HPLC | Cowan, R. and Whittaker, R. G., Pept.Res. 1990. 3: 75-80. |
| 30 | Mobilities of amino acids on chromatography paper (RF) | Akintola, A. and Aboderin, A. A., Int.J.Biochem. 1971. 2: 537-544. |
| 31 | Hydrophobic constants derived from HPLC peptide retention times | Wilson, K. J., Honegger, A., Stotzel, R. P., and Hughes, G. J., Biochem.J. 1981. 199: 31-41. |

In some preferred embodiments, amino acid physical property principal components are used as the inputs to build mathematical descriptors of peptides. A particular advantage of principal component analysis is that the weighting and ranking of the principal components reflect the contribution of each to the underlying variance. Principal components thus provide uncorrelated or orthogonal proxies which are weighted and ranked.

Briefly, for MHC-II a protein is broken down into 15-mer peptides each offset by 1 amino acid. The peptide 15-mers are converted into vectors of principal components wherein each amino acid in a 15-mer is replaced by three z-scale descriptors. $\{z1(aa1),z2(aa1),z3(aa1)\}$, $\{z1(aa2),z2(aa2),z3(aa2)\}$, $\{z1(aa15),z2(aa15),z3(aa15)\}$ that are effectively physical property proxy variables. With these descriptors ensembles of neural network prediction equation sets are developed, using publicly available datasets of peptide-MHC binding data, wherein the inhibitory concentration 50% ($ic_{50}$) has been catalogued as a measure of binding affinity of the peptides for a number of different HLAs. Because the $ic_{50}$ data have a numerical range in excess of 10,000-fold they are natural logarithm transformed to give the data better distributional properties for predictions and subsequent statistical analysis used the $\ln(ic_{50})$. For each of the 15-mers predicted $\ln(ic_{50})$ values are computed for fourteen different human DRB class MHC-II alleles DRB1*0101, DRB1*0301, DRB1*0401, DRB1*0404, DRB1*0405, DRB1*0701, DRB1*0802, DRB1*0901, DRB1*1101, DRB1*1302, DRB1*1501, DRB3*0101, DRB4*0101, DRB5*0101, or, for example, human DPQ class and human DQB alleles. The peptide data is indexed to the N-terminal amino acid and thus each prediction corresponds to the 15-amino acid peptide downstream from the index position. See, e.g., An integrated approach to epitope analysis I: Dimensional reduction, visualization and prediction of MHC binding using amino acid principal components and regression approaches. Bremel R D, Homan E J. Immunome Res. 2010 Nov. 2; 6:7; An integrated approach to epitope analysis II: A system for proteomic-scale prediction of immunological characteristics. Bremel R D, Homan E J. Immunome Res. 2010 Nov. 2; 6:8.

An identical process is then followed with all 9-mer peptides for prediction of binding to 35 MHC-I alleles: A*0101, A*0201, A*0202, A*0203, A*0206, A*0301, A*1101, A*2301, A*2402, A*2403, A*2601, A*2902, A*3001, A*3002, A*3101, A*3301, A*6801, A*6802, A*6901, B*0702, B*0801, B*1501, B*1801, B*2705, B*3501, B*4001, B*4002, B*4402, B*4403, B*4501, B*5101, B*5301, B*5401, B*5701, B*5801. Each of the alleles has a different characteristic mean and standard deviation of binding affinity. Thus, for statistical comparisons involving multiple HLA alleles the predicted $\ln(ic_{50})$ values are standardized to zero mean and unit standard deviation on a within-protein basis. The same process has been repeated with murine alleles and may be applied to the MHC molecules of any other species for which there are training sets available. It may further applied to any additional human alleles for which training sets become available.

The current invention provides a novel extension of statistical work of Wold and his colleagues who introduced the concept of amino acid principal components of small peptides in a predictive way with a partial least squares (PLS) regression process. See, e.g., Sjostrom M, Eriksson L, Hellberg S, Jonsson J, Skagerberg B, et al. (1989) Peptide QSARS: PLS modelling and design in principal properties, Prog Clin Biol Res 291: 313-317; Hellberg S, Sjostrom M, Skagerberg B, Wold S (1987) Peptide quantitative structure-activity relationships, a multivariate approach. J Med Chem 30: 1126-1135; Linusson A, Elofsson M, Andersson I E, Dahlgren M K (2010) Statistical molecular design of balanced compound libraries for QSAR modeling. Curr Med Chem 17: 2001-2016; Linusson A, Gottfries J, Lindgren F, Wold S (2000) Statistical molecular design of building blocks for combinatorial chemistry. J Med Chem 43: 1320-1328.

The methodology elaborated herein enables the description of binding of an amino acid subset or peptide derived from a protein to a binding partner, based on the use of principal components as proxies for the salient physical parameters of the peptide. Having used the principal components to reduce the dimensionality of the descriptors to a mathematical expression, it is then possible to analyze the binding interface of the peptide by statistical comparison to the binding of training sets of peptides to MHC molecules. In applications described herein, this technology is applied to understanding the binding to binding partners derived from the humoral and cellular immune system (B cell receptors or antibodies and MHC molecules which present peptides to T-cell epitopes). This however should not be considered limiting and the methodology may also be applied to other peptide binding and recognition events. Examples of such events include but are not limited to enzyme recognition of peptides, receptor binding of peptides (including but not limited to sensory receptors such as olfactory or taste receptors, receptors which bind to protein hormones, viral receptors on cell surfaces etc). Indeed the approach of using principal components to describe a peptide interface with a binding partner is applicable whether said binding partner is another protein or a lipid, carbohydrate or other substrate.

The detailed processes of the computer assisted methods are described in PCT/US2011/029192, incorporated by reference herein its entirety. The present invention addresses specific applications of the processes.

Modification of Binding Affinity

Once an epitope has been identified by the computer implemented process outlined above and as further described in PCT/US2011/029192, the present invention provides means to design a synthetic epitope wherein the binding affinity of such a peptide epitope to a MHC molecule is increased or decreased relative to the native peptide. Therefore the present invention provides an approach to design an MHC binding peptide with increased or reduced binding affinity. By changing the duration of binding, or dwell time of the peptide in a MHC molecular groove the outcome of the immune stimulation which results from said pMHC engaging a T cell receptor can be changed. In some embodiments the change in binding affinity may result in an increase in T helper and cytotoxic T cell responses and the amplification of an immune response. In yet other embodiments the change in binding affinity may result in an immunosuppressive response. The present invention provides the means to bring about such immunomodulation. In yet other embodiments the present invention enables changes in the epitope peptide which change the amino acid motif exposed to T cell recognition and thus may result in stimulation of a different T cell population. In some embodiments this may have the goal of increasing or reducing the immune response or on yet other embodiments of guiding the immune response along a particular clonal expansions pathway.

The alteration in binding affinity can be accomplished by making one or more amino acid changes in the peptide. The present invention allows the simulation of the effect on predicted binding affinity resulting from many possible amino acid changes and hence the selection of those changes which bring about the desired change through increase or reduction of binding.

In yet other instances such changes may be effected to change the amino acids exposed to the T cells, in other embodiments such changes may be effected to change the binding to the MHC molecular groove. As binding is specific to each allele of MHC the change in amino acids produces an increase or decrease in binding specific to a particular MHC allele. In some embodiments amino acid changes may be made to effect a change in binding to 1, or 2, or 3 or up to 5 or more MHC alleles simultaneously.

The present invention provides approaches for increasing and decreasing MHC binding by adjustment of amino acids in an MHC binding peptide. Such peptides may be from epitopes derived from infectious organisms including, but not limited to, viruses, bacteria, fungi, rickettsia, helminthes and other pathogens and parasites. Examples of the infectious organisms which may be analyzed and from which peptides may be identified as epitopes and subjected to modification as described herein to change the binding to MHC molecules are the following:

*Francisella* spp., *Bartonella* spp., *Borrelia* spp., *Campylobacter* spp., *Chlamydia* spp., *Simkania* spp., *Escherichia* spp. *Ehrlichia* spp. *Clostridium* spp., *Enterococcus* spp., *Haemophilius* spp., *Coccidioides* spp., *Bordetella* spp., *Coxiella* spp., *Ureaplasma* spp., *Mycoplasma* spp., *Trichomatis* spp., *Helicobacter* spp., *Legionella* spp., *Mycobacterium* spp., *Corynebacterium* spp., *Rhodococcus* spp., *Rickettsia* spp., *Arcanobacterium* spp., *Bacillus* spp., *Listeria* spp., *Yersinia* spp., *Shigella* spp., *Neisseria* spp., *Streptococcus* spp., *Staphylococcus* spp., *Vibrio* spp., *Salmonella* spp., *Treponema* spp., *Brucella* spp., *Campylobacter* spp., *Shigella* spp., *Mycoplasma* spp., *Pasteurella* spp., *Pseudomonas* ssp., and *Burkholderii* spp, Human and porcine rhinovirus, Human coronavirus, Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, *Candida, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi, Ancylostama, Strongylus, Trichostrongylus, Haemonchus, Ostertagia, Ascaris, Toxascaris, Uncinaria, Trichuris, Dirofilaria, Toxocara, Necator, Enterobius, Strongyloides* and *Wuchereria; Acanthamoeba* and other amoebae, *Cryptosporidium, Fasciola, Hartmanella, Acanthamoeba, Giardia lamblia, Isospora belli, Leishmania, Naegleria, Plasmodium* spp., *Pneumocystis carinii, Schistosoma* spp., *Toxoplasma gondii*, and *Trypanosoma* spp., among other viruses, bacteria, archaea, protozoa, fungi, and the like.

The present invention also provides approaches for increasing and decreasing MHC binding by adjustment of amino acids in an MHC binding peptide where such peptides are from epitopes derived from proteins from noninfectious sources, including but not limited to endogenous epitopes associated with autoimmune diseases, tumor associated antigens, and allergens. These are addressed in more detail below.

Many of the major non-infectious diseases cause characteristic epitopes to be displayed on the surface of cells. Cancers may be divided into two types, those associated with an underlying viral etiology and those which arise from a mutation of genes which control cell growth and division. In both cases, the surface epitopes may differ from normal cells either through expression of viral coded epitopes or overexpression of normal self proteins (e.g., HER-2 human epidermal growth factor receptor 2 overexpression in some breast cancers) (Sundaram et al. 2002. Biopolymers 66:200-216). The appearance of distinct epitopes offers the opportunity to target immunotherapies and vaccines to tumor cells (Sundaram et al., 2002 Biopolymers (Pept Sci), 66:200-216; Loo and Mather. 2008. Curr. Opin. Pharmacol. 8:627-631; Reichertand and Valge-Archer. 2007. Nat. Rev. Drug Discov. 6:349-356; King et al. 2008. QJM. 101:675-683).

Accordingly, in some embodiments, the protein or peptide sequence information used to identify epitopes is from a cancer or tumor. Examples include, but are not limited to, sequence information from bladder carcinomas, breast carcinomas, colon carcinomas, kidney carcinomas, liver carcinomas, lung carcinomas, including small cell lung cancer, esophagus carcinomas, gall-bladder carcinomas, ovary carcinomas, pancreas carcinomas, stomach carcinomas, cervix carcinomas, thyroid carcinomas, prostate carcinomas, and skin carcinomas, including squamous cell carcinoma and basal cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myclogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, leiomyosarcoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. In some embodiments, sequence information from individual proteins from the cancer cells are analyzed for epitopes according the process of the present invention. In some embodiments, sequence information from a set of proteins, such as transmembrane proteins, from the cancer cells are analyzed for epitopes according to the process of the present invention.

A number of diseases have also been identified as the result of autoimmune reactions in which the body's adaptive immune defenses are turned upon itself. Among the diseases recognized to be the result of autoimmunity, or to have an autoimmune component are celiac disease, narcolepsy, rheumatoid arthritis and multiple sclerosis (Jones, E. Y. et al, 2006. Nat. Rev. Immunol. 6:271-282). In a number of other instances infections are known to lead to a subsequent autoimmune reaction, including, for example but not limited to, in Lyme Disease, Streptococcal infections, and chronic respiratory infections (Hildenbrand, P. et al, 2009. Am. J. Neuroradiol. 30:1079-1087; Lee, J. L. et al, Autoimmun. Rev. 10.1016 0.2009; Leidinger, P. et al Respir. Res. 10:20, 2009). Enhanced ability to define and characterize peptides which form epitopes on the surface of cells in autoimmune will therefore facilitate the development of interventions which can ameliorate such diseases. Accordingly, in some embodiments, sequence information from cells that are involved in an autoimmune reaction or disease is analyzed according to the methods of the present invention. In some embodiments, sequence information from individual proteins from the cells are analyzed for epitopes according the process of the present invention. In some embodiments, sequence information from a set of proteins, such as transmembrane proteins, from the cells are analyzed for epitopes according to the process of the present invention.

In some particular embodiments the autoimmune diseases are those affecting the skin, which often cause autoimmune blistering diseases. These include but are not limited to pemphigus vulgaris and pemphigus foliaceus, bullous pemphigoid, paraneoplastic pemphigus, pemphigoid gestationis, mucous membrane pemphigus, linear IgA disease, Anti-Laminin pemphigoid, and epidermolysis bullosa aquisitiva. Some of the proteins which have been implicated as the target of the autoimmune response include desmogelin 1, 3 and 4, E-adherin, alpha 9 acetyl choline receptor, pemphaxin, plakoglobin, plakin, envoplakin, desmoplakin, BP 180, BP230, desmocholin, laminin, type VII collagen, tissue transglutaminase, endomysium, anexin, ubiquitin, Castlemans disease immunoglobulin, and gliadin. This list is illustrative and should not be considered limiting. In some instances peptides which bind antibodies and thus contain B cell epitopes have been described. Giudice et al., Bullous pemphigoid and herpes gestationis autoantibodies recognize a common non-collagenous site on the BP180 ectodomain. J Immunol 1993, 151:5742-5750; Giudice et al., Cloning and primary structural analysis of the bullous pemphigoid autoantigen BP180. J Invest Dermatol 1992, 99:243-250; Salato et al., Role of intramolecular epitope spreading in pemphigus vulgaris. Clin Immunol 2005, 116:54-64; Bhol et al., Correlation of peptide specificity and IgG subclass with pathogenic and nonpathogenic autoantibodies in pemphigus vulgaris: a model for autoimmunity. Proc Natl Acad Sci USA 1995, 92:5239-5243. Further T cell epitopes have been characterized Hacker-Foegen et al., T cell receptor gene usage of BP180-specific T lymphocytes from patients with bullous pemphigoid and pemphigoid gestationis. Clin Immunol 2004, 113:179-186. However, no systematic attempt has been made to plot the occurrence of all MHC binding regions and B cell eptopes in the proteins associated with cutaneous autoimmune disease, nor to determine the coincidence of B-cell epitopes with high affinity MHC binding regions.

In some embodiments, the present invention provides peptides from the aforementioned proteins associated with cutaneous autoimmune diseases which have characteristics of B cell epitopes and which bind with high affinity to MHC molecules, whether those two features are in overlapping or contiguous peptides or peptides that are bordering within 3 amino acids of each other.

A number of autoimmune disorders have been linked to immune responses triggered by infectious organisms which bear immune mimics of self-tissue epitopes. Examples include, but are not limited to, Guillan Bane (Yuki N (2001) Lancet Infect Dis 1 (1): 29-37, Yuki N (2005) Curr Opin Immunol 17 (6): 577-582; Kieseier B C et al, (2004) Muscle Nerve 30 (2): 131-156), rheumatoid arthritis (Rashid T et al (2007) Clin Exp Rheumatol 25 (2): 259-267), rheumatic fever (Guilherme L, Kalil J (2009) J Clin Immunol). In one embodiment the computer based analysis system described herein allows characterization of epitope mimics and can be applied to a variety of potential mimic substrates, including but not limited to vaccines, biotherapeutic drugs, food ingredients, to enable prediction of whether an adverse reaction could arise through exposure of an individual to a molecular mimic and which individuals (i.e. comprising which HLA haplotypes) may be most at risk.

Allergy is another example of an immune epitope mediated disease. The present invention in one particular embodiment is applicable to the modification of allergen peptides to induce immunosuppression or tolerization or to generate a vaccine against the allergen. Among the protein allergens from which peptides may be identifies as epitopes and modified are those listed in the SDAP Structural database (see the website at Fermi.utmb.edu/SDAP/index.html): These include abut are not limited to allergens derived from the following species *Acarus siro, Actinidia chinensis, Actinidia deliciosa, Aedes aegyptii, Alnus glutinosa, Alternaria alternate, Amaranthus retroflexus, Ambrosia artemisiifolia, Ambrosia psilostachya, Ambrosia trifida, Ananas comosus, Anacardium occidentale, Anisakis simplex, Anthoxanthum odoratum, Apis cerana, Apis dorsata, Apium graveolens, Apis mellifera, Arachis hypogaea, Arabidopsis thaliana, Archaeopotamobius sibiriensis, Argas reflexus, Artemia franciscana, Artemisia vulgaris, Prunus persica, Ascaris lumbricoides, Ascaris suum, Aspergillus fumigatus, Aspergillus flavus, Aspergillus niger, Aspergillus oryzae, Aspergillus versicolor, Asparagus officinalis, Bertholletia excelsa, Betula verrucosa (Betula pendula), Beta vulgaris, Blattella germanica, Blomia tropicalis, Bombus pennsylvanicus, Bombus terrestris, Bombyx mori, Bos domesticus, Brassica juncea, Brassica napus, Brassica oleracea, Brassica rapa, Brugia malayi, Canis familiaris (Canis domesticus), Candida albicans, Candida boidinii, Capsicum annuum, Carpinus betulus, Carya illinoinensis, Carica papaya, Castanea sativa, Catharanthus roseus, Cavia porcellus, Charybdis feriatus, Chamaecyparis obtusa, Chenopodium album, Chironomus kiiensis, Chironomus thummi thummi, Citrus limon, Citrus reticulata, Citrus sinensis, Cladosporium cladosporioides, Cladosporium herbarum, Clupea harengus, Coffea arabica, Coprinus comatus, Corylus avellana, Crangon crangon, Crassostrea gigas, Crocus sativus, Cryptomeria japonica, Ctenocephalides felis felis, Cucumis melo, Culicoides nubeculosus, Cupressus arizonica, Cupressus sempervirens, Curvularia lunata (Cochliobolus lunatus), Cynodon dactylon, Cyprinus carpio, Dactylis glomerate, Daucus carota, Dendronephthya nipponica, Dermatophagoides farinae, Dermatophagoides microceras, Dermatophagoides pteronyssinus, Dictyocaulus viviparus, Dirofilaria immitis, Dolichovespula arenaria, Dolichovespula maculata, Epicoccum purpurascens, Equus caballus, Euroglyphus maynei, Fagopyrum esculentum, Fagus sylvatica, Fagopyrum tataricum, Felis domesticus, Festuca pratensis, Forcipomyia taiwana, Fragaria ananassa, Fraxinus excelsior, Fusarium culmorum, Fusarium solani, Gadus callarias, Gadus morhua, Gallus domesticus, Glossina morsitans morsitans, Glycyphagus domesticus, Glycine max, Haliotis diversicolor, Haliotis midae, Harmonia axyridis, Helianthus annuus, Helix aspersa, Hevea brasiliensis, Holcus lanatus, Homarus americanus, Homo sapiens, Hordeum vulgare, Humulus japonicus, Juglans nigra, Juglans regia, Juniperus ashei, Juniperus oxycedrus, Juniperus sabinoides, Juniperus virginiana, Lactuca sativa, Lens culinaris, Lepidoglyphus destructor, Lepisma saccharina, Lepidorhombus whiffiagonis, Ligustrum vulgare, Liposcelis bostrichophila, Litchi chinensis, Litopenaeus vannamei, Lolium perenne, Lupinus angustifolius, Lycopersicon esculentum, Malus domestica, Malassezia furfur, Malassezia sympodialis, Manihot esculenta, Mercurialis annua, Metapenaeus ensis, Mimachlamys nobilis, Morus nigra, Musa acuminata, Mus musculus, Myrmecia pilosula, Olea europea, Oncorhynchus mykiss, Oreochromis mossambicus, Oryctolagus cuniculus, Oryza sativa, Ostrya carpinifolia, Pandalus borealis, Panulirus stimpsoni, Parietaria judaica, Parietaria officinalis, Paspalum notatum, Penaeus aztecus, Penicillium brevicompactum, Penicillium citrinum, Penicillium chrysogenum* (formerly *P. notatum*), *Penicillium crustosum, Penaeus indicus, Penaeus monodon, Penicillium oxalicum, Periplaneta americana, Perna viridis, Persea americana, Petroselinum crispum, Phalaris aquatica, Phaseolus vulgaris, Phleum pratense, Phoenix dactylifera, Pisum savitum, Pistacia vera, Platanus x acerifolia (Platanus acerifolia), Plantago lanceolata, Platanus orientalis, Plodia interpunctella, Poa pratensis, Polistes annularies, Polistes dominulus, Polistes exclamans, Polistes fuscatus, Polistes gallicus, Polistes metricus, Polybia paulista, Polybia scutellaris (P. scutellaris rioplatensis), Pontastacus leptodactylus, Prunus armeniaca, Prunus avium, Prunus domestica, Prunus dulcis, Psilocybe cubensis, Pyrus communis, Quercus alba, Rana esculenta, Rattus norvegius, Rhodotorula mucilaginosa, Ricinus communis, Rubus idaeus, Salsola kali, Salmo salar, Sardinops sagax, Schizophyllum commune, Scomber australasicus, Scomber japonicus, Scomber scombrus, Sebastes marinus, Secale cereale, Sesamum indicum, Sinapis alba, Solenopsis geminata, Solenopsis invicta, Solenopsis richteri, Solenopsis saevissima, Solanum tuberosum, Sorghum halepense, Stachybotrys chartarum, Syringa vulgaris, Tabanus yao, Taraxacum officinale, Thaumetopoea pityocampa, Theragra chalcogramma, Thunnus albacares, Todarodes pacificus, Triticum aestivum, Trichophyton rubrum, Trichophyton tonsurans, Triatoma protracta, Triplochiton scleroxylon, Tyrophagus putrescentiae, Vespula flavopilosa, Vespula germanica, Vespula maculifrons, Vespula pennsylvanica, Vespula squamosa, Vespula vulgaris, Vespula vidua, Vespa crabro, Vespa mandarins, Vespa magnifica, Vigna radiata, Vitis vinifera, Xiphias gladius, Zea mays, Ziziphus mauritiana.*

Modification of Imunogenicity of Biopharmaceuticals

A particular group of proteins which may be antigenic are biopharmaceuticals. Many proteins are used as therapeutics and protein drugs are the fastest growing. There are many classes of protein drug but a particularly large group comprise recombinant antibodies and antibody fusions. As foreign or non self proteins introduced into the body the biotherapeutic protein is taken up and processed by antigen presenting cells and processed for presentation to T cells as a pMHC complex. Many biotherapeutics elicit an adverse reaction, most often inducing antibodies which act as inhibitors. The process of development of biotherpautics which involves manipulation of amino acids to increase antibody affinity or to humanize the antibody introduces motifs which are seen as antigenic. A particular embodiment of the present invention therefore is to identify epitopes within biotherapeutic proteins and to permit the simulation of amino acid changes which can increase or decrease MHC binding of particular peptides. In some particular embodiments the application of the present invention is to design biotherapeutics which are particularly appropriate for patients of certain MHC alleles.

Orientation of the Binding Peptide

The binding of a peptide within a MHC molecular groove is a function of binding affinity, and space shape of the molecule determining the fit. As shown in PCT/US2011/029192, binding affinity can be predicted based on multiple physical parameters of the constituent amino acids of a peptide. Cleavage by cathepsin cuts the protein, or sub sequences therefor to release a 9-mer or a 10-mer, a 15-mer, or a 11-22-mer, or other size of peptide which binds in the MHC I or MHC II groove. It is a general practice of those skilled in the art to analyze protein amino acid sequences starting from the N terminal and moving towards the C terminal, a direction which may be termed canonical. Within the environment of an intracellular space where a MHC-peptide binding reaction takes place there is no such convention and consequently a binding space shape fit may be achieved in either canonical or non-canonical orientation. The present invention examines situations where both canonical and non-canonical pMHC binding occurs and provides a computer implemented process for predicting MHC binding to peptides in either orientation.

Relationship of B and T Cell Responses

We have previously demonstrated that proteins comprise B cell epitopes, MHC binding and cathepsin cleavage which often are placed in close proximity to each other to constitute an epitope dense region or immunological kernel (See, e.g., PCT/US2011/029192, Bremel and Homan, 2013 supra) in which all signals necessary to coordinate an immune response are present. On the establishment of a B cell synapse the B cell receptor and B cell epitope binding is followed by internalization of a sequence of the protein containing the aforesaid binding point. In the process those sequences immediately adjacent to the B cell epitope are most likely to be internalized simultaneously and give rise to pMHC complexes and surface presentation on B cells towards T cells.

In some instances however epitope maps of proteins identify B cell linear epitopes which occur separated from high affinity MHC binding regions, these are T independent B cell epitopes and are unlikely to generate a specific memory.

Vaccination may have as its goal the upregulation of the immune response to generate antibodies and a cytotoxic T cell response to eliminate an exogenous epitope such as one residing on a pathogen or a tumor cell. In other instances vaccination may have as its goal the induction of tolerization or immunosuppression to prevent or mitigate autoimmunity or allergy. The goal of vaccination is typically to induce a long term immunological memory in which re-exposure results in an anamnestic response. In other instances the goal may be to calibrate the duration of a specific immune response and reduce either the antibody response or the cytotoxic T cell response. Under such circumstances it may be beneficial to be able to identify epitopes which stimulate one arm of the immune response but not the other. In some specific embodiments therefor an antibody response without a T cell response may be desired; one example of this which is non-limiting is in Alzheimers disease (Ghochikyan A et al Neurosci Lett. 2014). In yet other embodiments a T cell response in the absence of an antibody response may be the preferred outcome. The present invention, by allowing detailed mapping of epitopes, provides the tools for the identification and selection of epitopes for incorporation in a vaccine based on whether they will induce an antibody response, cellular response, or both. The present invention allows selection of amino acid sequences with precision which have the desired combination of B cell epitopes and high affinity MHC binding sequences needed for T cell epitopes.

Identification of Immunological Kernels

B-cell epitopes may be linear peptide sequences of varying length or may depend on three dimensional topology comprising multiple short peptide sequences. In contrast, T-cell epitopes lie within short linear peptide sequences (e.g., 8-mers or 9-mers up to 15-mers with or without a few N- or C-terminal flanking residues which are bound by the MHC receptor after proteasomal processing (Janeway 2001. Immunobiology. Garland Publishing). T-cell epitopes have multiple roles in vaccination controlling the outcome of both antibody mediated and cell-mediated responses (Kaufmann 2007). As has been previously demonstrated (Bremel and Homan, 2013, supra and PCT/US2011/029192) there is a commonly occurring intraprotein organization in which B cell epitopes are typically flanked by a cathepsin cleavage site on one side of a B cell linear epitope and a sequence of amino acids starting 3-7 amino acids on the other side of the linear B cell epitope in which there are multiple overlaid peptides which have high affinity for biding to multiple MHC molecules, including both MHC I and MHC II. This relationship is shown in FIG. 1. While the location within a protein of such an immunological kernel may be identified by mapping by the computer assisted methods described herein and in a prior filing (uTOPE 1), given the frequent association of B-cell epitopes and MHC binding, it is possible to utilize B cell linear epitopes as a marker for the adjacent MHC binding peptides. In such an application the B cell binding or antibody binding sequence is determined and a sequence of amino acids selected extending 20-30 amino acids from that B cell binding epitope, in preferred embodiments extending towards the C terminal but in some other embodiments on the N terminal side of the B cell epitope. The present invention therefore comprises using a B cell linear epitope as a marker and selection tool for identification and isolation of a MHC binding peptide. Not all sequences flanking a B cell epitope will provide a high affinity MHC binding peptide but the probability of a MHC binding peptide is higher starting within 3-10 amino acids adjacent to the B linear cell epitope and extending up to 30-40 amino acids from such an epitope.

Epitope Analysis of *Brucella* Spp

The present invention enables the high throughput processing of whole microbial proteomes to identify sequences of interest as epitopes, particularly with a view to development of vaccines comprising synthetic peptides. As discussed above *Brucella* spp cause a heavy disease toll on both humans and animals and the development of an effective vaccine is a long sought after goal.

Brucellosis is most prevalent zoonosis worldwide (WHO (2006) The control of neglected zoonotic diseases; Report of a Joint WHO/DFID-AHP Meeting with the participation of FAO and OIE. Geneva; Pappas G et at (2006) The new global map of human brucellosis. Lancet InfectDis 6: 91-99. Brucellosis is a debilitating chronic disease for those naturally infected through exposure to bacteria in milk and placental fluids of ruminant livestock (Corbel M J (1997) Brucellosis: an overview. EmergInfectDis 3: 213-221). As infection also occurs by inhalation of aerosols and the infective dose is low, *Brucella melitensis* is a potential bioterror agent with capacity to infect large numbers of people. A model developed by the CDC of a bioterrorist attack scenario on a U.S. city with aerosolized *B. melitensis* estimated a financial impact of $477.7 million per 100,000 people exposed Kaufmann A F, et at (1997) The economic impact of a bioterrorist attack: are prevention and postattack intervention programs justifiable? EmergInfectDis 3: 83-94); less deadly but far more costly than an anthrax attack.

No effective vaccine exists to protect humans from brucellosis. Several weeks of antibiotic treatment are required, but may be unable to clear residual foci of bacteria. Historically, vaccines developed to control disease in cattle, sheep, and goats, the main natural reservoir, are comprised of live attenuated *Brucella* organisms, still capable of causing disease in humans. Killed organisms are ineffective vaccines. DNA and subunit recombinant vaccines offer the potential of safety but have yet to provide long lasting or broad coverage. A safe and effective vaccine suitable for human use is needed to offer protection to those facing occupational exposure, and to provide large scale protection and post-exposure intervention in the face of deployment of brucellosis as a bioterror weapon. The longer incubation period of brucellosis offers the opportunity to implement post-exposure vaccination in the face of mass exposure to enhance clearance.

In one embodiment therefore the present invention has been applied to analyze multiple complete proteomes of *Brucella* spp and identify epitope dense regions of amino acids which when expressed as synthetic proteins can serve as vaccine components. In particular the present invention is useful for identifying epitopes that are conserved across different strains of an infectious microorganism.

Vaccines

Vaccines are considered to be the most effective medical intervention (Rappuoli et al. 2002. Science 297:937-939), reducing the burden of infectious diseases which kill millions worldwide. A comprehensive reverse vaccinology approach leading to identification of multiple peptides capable of inducing both antibody and cell mediated responses will allow rational design of vaccines to be achieved more rapidly, more precisely, and to produce more durable protection, while avoiding deleterious cross reactivities. By distilling down the epitope to the minimal effective size, from protein to peptide, we can facilitate engineering of delivery vehicles to display an array of several epitopes, inducing an immunity which poses multiple barriers to escape mutation. Reverse vaccinology, assisted by our invention, has particular potential for controlling emerging pathogens where vaccines or epitope targeting drugs can be designed and implemented based on genome sequences even before in vitro culture systems are worked out.

In some embodiments, the present invention provides a vaccine comprising one or more of the polypeptides which comprise epitopes as described above. In some embodiments, the present invention provides compositions comprising one or more of the polypeptides described above and an adjuvant. In some embodiments, the vaccines comprise recombinant or synthetic polypeptides derived from a transmembrane protein from a target cell or organisms that comprises one or more B-cell epitopes and/or peptides that bind to one or more members of an MHC or HLA superfamily. Suitable target cells and organisms include, but are not limited to, prokaryotic and eukaryotic organisms, bacteria, archaea, protozoas, viruses, fungi, helminthes, carcinomas, tumors, cancer cells, etc. as described in detail above.

As used herein, the term "vaccine" refers to a composition comprising any combination of peptides or single peptide formulation. There are various reasons why one might wish to administer a vaccine of a combination of the peptides of the present invention rather than a single peptide. Depending on the particular peptide that one uses, a vaccine might have superior characteristics as far as clinical efficacy, solubility, absorption, stability, toxicity and patient acceptability are concerned. It should be readily apparent to one of ordinary skill in the art how one can formulate a vaccine of any of a number of combinations of peptides of the present invention. There are many strategies for doing so, any one of which may be implemented by routine experimentation.

The peptides of the present invention may be administered as a single agent therapy or in addition to an established therapy, such as inoculation with live, attenuated, or killed virus, or any other therapy known in the art to treat the target disease or epitope-sensitive condition.

The appropriate dosage of the peptides of the invention may depend on a variety of factors. Such factors may include, but are in no way limited to, a patient's physical characteristics (e.g., age, weight, sex), whether the compound is being used as single agent or adjuvant therapy, the type of MHC restriction of the patient, the progression (i.e., pathological state) of the infection or other epitope-sensitive condition, and other factors that may be recognized by one skilled in the art. In general, an epitope or combination of epitopes may be administered to a patient in an amount of from about 50 micrograms to about 5 mg; dosage in an amount of from about 50 micrograms to about 500 micrograms is especially preferred.

In some embodiments, the peptides are expressed on bacteria, such as lactococcus and lactobacillus, or expressed on virus or virus-like particles for use as vaccines. In some embodiments, the peptides are incorporated into other carriers as are known in the art. For example, in some embodiments, the polypeptides comprising one or more epitopes are conjugated or otherwise attached to a carrier protein. Suitable carrier proteins include, but are not limited to keyhole limpet hemocyanin, bovine serum albumin, ovalbumin, and thyroglobulin. In yet other embodiments the polypeptide may be fused to an Fc region of an immunoglobulin for delivery to a mucosal site bearing corresponding receptors.

One may administer a vaccine of the present invention by any suitable method, which may include, but is not limited to, systemic injections (e.g., subcutaneous injection, intradermal injection, intramuscular injection, intravenous infusion) mucosal administrations (e.g., nasal, ocular, oral, vaginal and anal formulations), topical administration (e.g., patch delivery), or by any other pharmacologically appropriate technique. Vaccination protocols using a spray, drop, aerosol, gel or sweet formulation are particularly attractive and may be also used. The vaccine may be administered for delivery at a particular time interval, or may be suitable for a single administration.

Vaccines of the invention may be prepared by combining at least one peptide with a pharmaceutically acceptable liquid carrier, a finely divided solid carrier, or both. As used herein, "pharmaceutically acceptable carrier" refers to a carrier that is compatible with the other ingredients of the formulation and is not toxic to the subjects to whom it is administered. Suitable such carriers may include, for example, water, alcohols, natural or hardened oils and waxes, calcium and sodium carbonates, calcium phosphate, kaolin, talc, lactose, combinations thereof and any other suitable carrier as will be recognized by one of skill in the art. In a most preferred embodiment, the carrier is present in an amount of from about 10 uL (micro-Liter) to about 100 uL.

In some embodiments, the vaccine composition includes an adjuvant. Examples of adjuvants include, but are not limited to, mineral salts (e.g., aluminum hydroxide and aluminum or calcium phosphate gels); oil emulsions and surfactant based formulations (e.g., MF59 (microfluidized detergent stabilized oil-in-water emulsion), QS21 (purified saponin), Ribi Adjuvant Systems, AS02 [SBAS2] (oil-in-water emulsion+MPL+QS-21), Montanide ISA-51 and ISA-720 (stabilized water-in-oil emulsion); particulate adjuvants (e.g., virosomes (unilamellar liposomal vehicles incorporating influenza haemagglutinin), ASO4 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+M. Phlei cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators (e.g., hGM-CSF or hIL-12 (cytokines that can be administered either as protein or plasmid encoded), Immudaptin (C3d tandem array); and inert vehicles, such as gold particles. In various embodiments, vaccines according to the invention may be combined with one or more additional components that are typical of pharmaceutical formulations such as vaccines, and can be identified and incorporated into the compositions of the present invention by routine experimentation. Such additional components may include, but are in no way limited to, excipients such as the following: preservatives, such as ethyl-p-hydroxybenzoate; suspending agents such as methyl cellulose, tragacanth, and sodium alginate; wetting agents such as lecithin, polyoxyethylene stearate, and polyoxyethylene sorbitan mono-oleate; granulating and disintegrating agents such as starch and alginic acid; binding agents such as starch, gelatin, and acacia; lubricating agents such as magnesium stearate, stearic acid, and talc; flavoring and coloring agents; and any other excipient conventionally added to pharmaceutical formulations.

Further, in various embodiments, vaccines according to the invention may be combined with one or more of the group consisting of a vehicle, an additive, a pharmaceutical adjunct, a therapeutic compound or agent useful in the treatment of the desired disease, and combinations thereof.

In another aspect of the present invention, a method of creating a vaccine is provided. The method may include identifying an immunogenic epitope; synthesizing a peptide epitope from the immunogenic epitope; and creating a composition that includes the peptide epitope in a pharmaceutical carrier. The composition may have characteristics similar to the compositions described above in accordance with alternate embodiments of the present invention. Accordingly, the present invention provides vaccines and therapies for a variety of infections and clinical conditions. These infections and conditions include, but are not limited to, Mediterranean fever, undulant fever, Malta fever, contagious abortion, epizootic abortion, Bang's disease, brucellosis, *Salmonella* food poisoning, enteric paratyphosis, Bacillary dysentery, *Pseudotuberculosis*, plague, pestilential fever, Tuberculosis, Vibrios, Circling disease, Weil's disease, Hemorrhagic jaundice (Leptospira icterohaemorrhagiae), canicola fever (*L. canicola*), dairy worker fever (*L. hardjo*), Relapsing fever, tick-borne relapsing fever, spirochetal fever, vagabond fever, famine fever, Lyme arthritis, Bannworth's syndrome, tick-borne meningopolyneuritis, erythema chronicum migrans, Vibriosis, Colibacteriosis, colitoxemia, white scours, gut edema of swine, enteric paratyphosis, Staphylococcal alimentary toxicosis, staphylococcal gastroenteritis, Canine Corona Virus (CCV) or canine parvovirus enteritis, feline infectious peritonitis virus, transmissible gastroenteritis (TGE) virus, Hagerman Redmouth Disease (ERMD), Infectious Hematopoietic necrosis (IHN), porcine *Actinobacillus* (*Haemophilus*) pleuropneumonia, Hansen's disease, Streptotrichosis, Mycotic Dermatitis of Sheep, Pseudoglanders, Whitmore's disease, Francis' disease, deer-fly fever, rabbit fever, O'Hara disease, Streptobacillary fever, Haverhill fever, epidemic arthritic erythema, sodoku, Shipping or transport fever, hemorrhagic septicemia, Ornithosis, Parrot Fever, Chlamydiosis, North American blastomycosis, Chicago disease, Gilchrist's disease, Cat Scratch Fever, Benign Lymphoreticulosis, Benign nonbacterial Lymphadenitis, Bacillary Angiomatosis, Bacillary Peliosis Hepatitis, Query fever, Balkan influenza, Balkan grippe, abattoir fever, Tick-borne fever, pneumorickettsiosis, American Tick Typhus, Tick-borne Typhus Fever, Vesicular Rickettsiosis, Kew Gardens Spotted Fever, Flea-borne Typhus Fever, Endemic Typhus Fever, Urban Typhus, Ringworm, Dermatophytosis, Tinea, Trichophytosis, Microsporosis, Jock Itch, Athlete's Foot, Sporothrix schenckii, dimorphic fungus, Cryptococcosis and histoplasmosis, Benign Epidermal Monkeypox, Herpesvirus simiae, Simian B Disease, Type C lethargic encephalitis, Yellow fever, Black Vomit, hantavirus pulmonary syndrome, Korean Hemorrhagic Fever, Nephropathia Epidemica, Epidemic Hemorrhagic Fever, Hemorrhagic Nephrosonephritis, lymphocytic choriomeningitis, California encephalitis/La Crosse encephalitis, African Hemorrhagic Fever, Green or Vervet Monkey Disease, Hydrophobia, Lyssa, Infectious hepatitis, Epidemic hepatitis, Epidemic jaundice, Rubeola, Morbilli, Swine and Equine Influenza, Fowl Plague, Newcastle disease, Piroplasmosis, toxoplasmosis, African Sleeping Sickness, Gambian Trypanosomiasis, Rhodesian Trypanosomiasis, Chagas's Disease, Chagas-Mazza Disease, South American Trypanosomiasis, Entamoeba histolytica, Balantidial dysentery, cryptosporidiosis, giardiasis, Cutaneous leishmaniasis; Bagdad boil, Delhi boil, Baum ulcer, Visceral leishmaniasis: kala-azar, Microsporidiosis, Anisakiasis, Trichinosis, Angiostrongylosis, eosinophilic meningitis or meningoencephalitis (*A. cantonensis*), abdominal angiostrongylosis (*A. costaricensis*), Uncinariasis, Necatoriasis, Hookworm Disease, Capillariasis, Brugiasis, Toxocariasis, Oesophagostomiasis, Strongyloidiasis, Trichostrongylosis, Ascaridiasis, Diphyllobothriasis, Sparganosis, Hydatidosis, Hydatid Disease, *Echinococcus granulosis*, Cystic hydatid disease, Tapeworm Infection, Schistosomiasis and the like. Malignant diseases caused by infectious pathogens are contemplated as well. The examples of such diseases include for example Burkitt's lymphoma caused by EBV, Rous sarcoma caused by Rous retrovirus, Kaposi' sarcoma caused by herpes virus type 8, adult T-cell leukemia caused by HTLV-I retrovirus, or hairy cell leukemia caused by HTLV-II, and many other tumors and leukemias caused by infectious agents and viruses. Further it may provide vaccines and therapies for emerging diseases yet to be defined, whether emerging from natural reservoirs or resulting from exposure to genetically engineered bioterror organisms.

In still further embodiments, the present invention provides vaccine compositions which may be applied for treatment of cancer. In some embodiments, the vaccines comprise recombinant or synthetic polypeptides from a transmembrane protein from a cancer cell that comprises one or more B-cell epitopes and/or peptides that bind to one or more members of an MHC or HLA superfamily. The polypeptides are identified as described above. In some embodiments, the polypeptides are attached to a carrier protein and/or used in conjunction with an adjuvant. Examples of can that can be treated include, but are not limited to, bladder carcinomas, breast carcinomas, colon carcinomas, kidney carcinomas, liver carcinomas, lung carcinomas, including small cell lung cancer, esophagus carcinomas, gall-bladder carcinomas, ovary carcinomas, pancreas carcinomas, stomach carcinomas, cervix carcinomas, thyroid carcinomas, prostate carcinomas, and skin carcinomas, including squamous cell carcinoma and basal cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myclogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, leiomyosarcoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In another embodiment the present invention provides therapies for a variety of autoimmune diseases which may include but are not limited to Ankylosing Spondylitis, Atopic allergy, Atopic Dermatitis, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune uveitis, Bullous Pemphigoid, Castleman's disease, Celiac disease, Cogan syndrome, Cold agglutinin disease, Crohns Disease, Dermatomyositis, Diabetes mellitus type 1, Eosinophilic fasciitis, Gastrointestinal pemphigoid, Goodpasture's syndrome, Graves' disease, Guillain-Barré syndrome, Anti-ganglioside Hashimoto's encephalitis, Hashimoto's thyroiditis, Systemic Lupus erythematosus, Miller-Fisher syndrome, Mixed Connective Tissue Disease, Myasthenia gravis, Narcolepsy, Pemphigus vulgaris, Polymyositis, Primary biliary cirrhosis, Psoriasis, Psoriatic Arthritis, Relapsing polychondritis, Rheumatoid arthritis, Sjögren's syndrome, Temporal arteritis, Ulcerative Colitis, Vasculitis, and Wegener's granulomatosis.

Antibodies

In some embodiments, the present invention provides for the development of antigen binding proteins (e.g., antibodies or fragments thereof) that bind to a polypeptide as described above. Monoclonal antibodies are preferably prepared by methods known in the art, including production of hybridomas, use of humanized mice, combinatorial display techniques, and the like. See, e.g., of Kohler and Milstein, Nature, 256:495 (1975), Wood et al., WO 91/00906, Kucherlapati et al., WO 91/10741; Lonberg et al., WO 92/03918; Kay et al., WO 92/03917 [each of which is herein incorporated by reference in its entirety]; N. Lonberg et al., Nature, 368:856-859 [1994]; L. L. Green et al., Nature Genet., 7:13-21 [1994]; S. L. Morrison et al., Proc. Nat. Acad. Sci. USA, 81:6851-6855 [1994]; Bruggeman et al., Immunol., 7:33-40 [1993]; Tuaillon et al., Proc. Nat. Acad. Sci. USA, 90:3720-3724 [1993]; and Bruggernan et al. Eur. J. Immunol., 21:1323-1326 [1991]); Sastry et al., Proc. Nat. Acad. Sci. USA, 86:5728 [1989]; Huse et al., Science, 246:1275 [1989]; and Orlandi et al., Proc. Nat. Acad. Sci. USA, 86:3833 [1989]); U.S. Pat. No. 5,223,409; WO 92/18619; WO 91/17271; WO 92/20791; WO 92/15679; WO 93/01288; WO 92/01047; WO 92/09690; WO 90/02809 [each of which is herein incorporated by reference in its entirety]; Fuchs et al., Biol. Technology, 9:1370-1372 [1991]; Hay et al., Hum. Antibod. Hybridomas, 3:81-85 [1992]; Huse et al., Science, 46:1275-1281 [1989]; Hawkins et al., J. Mol. Biol., 226:889-896 [1992]; Clackson et al., Nature, 352:624-628 [1991]; Gram et al., Proc. Nat. Acad. Sci. USA, 89:3576-3580 [1992]; Garrad et al., Bio/Technolog, 2:1373-1377 [1991]; Hoogenboom et al., Nuc. Acid Res., 19:4133-4137 [1991]; and Barbas et al., Proc. Nat. Acad. Sci. USA, 88:7978 [1991].

The antigen binding proteins of the present invention include chimeric and humanized antibodies and fragments thereof, including scFv's. (See e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 [each of which is herein incorporated by reference in its entirety]; Better et al., Science, 240:1041-1043 [1988]; Liu et al., Proc. Nat. Acad. Sci. USA, 84:3439-3443 [1987]; Liu et al., J. Immunol., 139:3521-3526 [1987]; Sun et al., Proc. Nat. Acad. Sci. USA, 84:214-218 [1987]; Nishimura et al., Canc. Res., 47:999-1005 [1987]; Wood et al., Nature, 314:446-449 [1985]; and Shaw et al., J. Natl. Cancer Inst., 80:1553-1559 [1988]), U.S. Pat. No. 5,225,539 (incorporated herein by reference in its entirety); Jones et al., Nature, 321:552-525 [1986]; Verhoeyan et al., Science, 239:1534 [1988]; and Beidler et al., J. Immunol., 141:4053 [1988]).

Applications

The method of the present invention are useful for a wide variety of applications, including but not limited to, the design and development of vaccines, biotherapeutic antigen binding proteins, diagnostic antigen binding proteins, and biotherapeutic proteins.

In some embodiments, the methods of the present invention are used to identify peptides that bind to one or more MHC or HLA binding regions. This application is highly useful in the development, design and evaluation of vaccines and the polypeptides included in the vaccine that are intended to initiate an immune response. In some embodiments, the methods of the present invention allow for the determination of the predicted binding affinities of one or more MHC binding regions for polypeptide(s)(and the epitopes contained therein) that is included in a vaccine or is a candidate for inclusion in a vaccine. Application of these methods identifies epitopes that are bound by particular MHC binding regions with high affinity, but at only low affinity by other MHC binding regions. Thus, the effectiveness of the epitopes for vaccination of population, subpopulation or individual with a particular haplotype can be determined. Thus, the processes of the present invention allow identification of populations or individuals that are predicted to be more or less responsive to the vaccine. If desired, the vaccine can then be designed to target a subset of the population with particular MHC binding regions or be designed to provide an immunogenic response in a high percentage of subjects within a population or subpopulation, for example, greater than 50%, 60%, 70%, 80%, 90%, 95% or 99% of all subjects within a population or subpopulation. The present invention therefore facilitates design of vaccines with selected polypeptides with a predicted binding affinity for MHC binding regions, and thus which are designed to elicit an immune response in defined populations (e.g., subpopulations or the entire population or a desired/target percentage of the population).

These methods are particularly applicable to the design of subunit vaccines that comprise isolated polypeptides. In some embodiments, polypeptides selected for a vaccine bind to one or more MHC binding regions with a predicted affinity for at least one MHC binding region of about greater than $10^5$ $M^{-1}$, about greater than $10^6$ $M^{-1}$, about greater than $10^7$ $M^{-1}$, about greater than $10^8$ $M^{-1}$, or about greater than $10^9$ $M^{-1}$. In some embodiments, these binding affinities are achieved for about 1% to 5%, 5% to 10%, 10% to 50%, 50% to 100%, 75% to 100% or 90% to 100% or greater than 90%, 95%, 98%, or 99% of subjects within a population or subpopulation.

It is also contemplated that different microorganism strains, viral strains or protein isotypes will vary in their ability to elicit immune responses from subjects with particular binding regions. Accordingly, the methods of the present invention are useful for selecting particular microorganism strains, viral strains or protein isotypes that are including in a vaccine. As above, the methods of the present invention allow for the determination of the predicted binding affinities of one or more MHC binding regions for epitopes contained in the proteome of an organism or protein isotype that are included vaccine or are candidates for inclusion in a vaccine. Application of these methods identifies epitopes that are bound by particular MHC binding regions with high affinity, but at only low affinity by other MHC binding regions. This process allows identification of populations or individuals that are predicted to be more or less responsive to the vaccine. If desired, the vaccine can then be designed to target a subset of the population with particular MHC binding regions or be designed to provide coverage of a high percentage of subjects within a population or subpopulation, for example, greater than 50%, 60%, 70%, 80%, 90%, 95% or 99% of all MHC subjects within a population or subpopulation. The present invention therefore facilitates design of vaccines with selected strains of an organism or virus or protein isotype, and thus which are designed to elicit an immune response in defined populations (e.g., subpopulations or the entire population or a desired/target percentage of the population). In some embodiments, strains of an organism or virus or protein isotype selected for a vaccine bind to one or more MHC binding regions with a predicted affinity for at least one MHC binding region of about greater than $10^5$ $M^{-1}$, about greater than $10^6$ $M^{-1}$, about greater than $10^7$ $M^{-1}$, about greater than $10^8$ $M^{-1}$, or about greater than $10^9$ $M^{-1}$. In some embodiments, these binding affinities are achieved for from one individual to about 1% to 5%, 5% to 10%, 10% to 50%, 50% to 100%, 75% to 100% or 90% to 100% or greater than 70%, 80%, 90%, 95%, 98%, 99%, 99.5% or 99.9% of subjects within a defined population or defined subpopulation.

Accordingly, these methods are particularly applicable to the development, design and/or production of therapeutic vaccines. In some embodiments, vaccines are designed to optimize the response of an individual patient of known MHC allotype. In these embodiments, the vaccine is designed to include epitopes that have a high predicted binding affinity for one or more MHC alleles in a subject. For example, in some embodiments, the vaccine comprises 1, 2, 3, 4, 5, 10 or 20 peptides with a predicted affinity for at least one MHC binding region of about greater than $10^5$ $M^{-1}$, about greater than $10^6$ $M^{-1}$, about greater than $10^7$ $M^{-1}$, about greater than $10^8$ $M^{-1}$, or about greater than $10^9$ $M^{-1}$. In some embodiments, the epitope is immunogenic for subjects whose HLA alleles are drawn from a group comprising 1, 5, 10 or 20 or more different HLA alleles. In some embodiments, the epitope is selected to be immunogenic for the HLA allelic composition of an individual patient.

Biopharmaceuticals are an increasing percentage of therapeutics approved and in development. As more protein drugs are more widely used, adverse reactions arising from immune response to the protein drugs are more commonly recognized, often among a narrow sector of the patient population of specific immunogenetics. There has been an increasing interest in de-antigenizing biopharmaceuticals. This is true of antibody-based biopharmaceuticals and replacement enzyme, hormone and blood clotting factor therapies. It is therefore of interest to be able to modify biopharmaceuticals to reduce the antigenicity of certain epitopes for certain patient genetic groups. In some instances this could lead to the development of multiple biopharmaceutical products with the same therapeutic goal but designed for specific patient groups. In some instances the target epitope is a peptide that ensures a T helper cell response (CD4) by binding to a MHC-II molecule; in other instances the epitope of interest binds to a MHC-I and induces a cytotoxic T cell response. In yet other embodiments the binding induces a Treg response.

As more allergens are characterized and there is better understanding of the epitopes which give rise to allergic reactions there is interest in developing peptides which can be used to tolerize or desensitize allergic individuals by inducing anergy. In some instances such peptides capable of inducing anergy have a higher binding affinity for MHC molecules than the allergen.

T cell receptors are somewhat promiscuous in their recognition of peptide-MHC combinations; it is recognized that the most important amino acids in the binding peptide are the central 5 amino acids both in the case of a 15-mer binding a MHC-II molecule and in the 9-mer binding MHC-I. For clarity in the following examples, FIG. 45 characterizes the peptide which binds in the MHC grooves as comprising 3 zones, two flanking sequences A and C and a core 5-mer shown as B.

Accordingly, embodiments of the present invention provide compositions and methods for optimizing MHC binding of peptide ligands (e.g., for use in research, screening, and therapeutic (e.g., pharmaceutical)) applications. Exemplary compositions and methods are described, for example, in Examples 14 and 15 below.

The ability to predict MHC binding affinity of any 15-mer or 9-mer peptide based on the principal component analysis of the component amino acids lays the foundation for being able to rapidly simulate the binding affinity of large numbers of variant peptides to any given MHC allele or combinations of alleles. A very large number of possible variants may exist; however by selecting a random sample of for example, but not limited to, 5000 or 10000 or 1,000,000 possible combinations of amino acids based on the amino acid frequency in the parent protein, it is possible to rapidly arrive at a small number of peptides that fulfill the criteria of predicted binding affinity for HLA alleles of interest. This small subset can then be tested in vitro or in animal models. This represents a very significant savings in time and money over testing of all variants empirically without guidance as to the changes in MHC binding. The use of principal component analysis makes it possible to simulate changes in binding affinity rapidly by calculating the predicted binding affinity a set of peptide combinations which achieve the desired result from among the many millions of potential amino acid combinations. In one embodiment the present invention provides a process that rapidly identifies a group of 20 or 30 or up to 100 peptides, which comprise alternative epitopes with binding affinity of at least 2 standard deviations higher or lower than the original peptide. This is a group which is practicable to test to ensure that bioactivity is retained.

Example 1

Application of Principal Component Analysis to Modify Binding Affinity of Selected Peptides The following examples below show how purposefully varying the amino acid composition of one or more of the core or flanking sequences in a MHC binding peptide (see zones A, B, and C shown in FIG. 2) can produce different results, either increasing or decreasing the antigenicity of a selected peptide for a specific set of HLA alleles of interest. While the examples are intended to illustrate the concepts they are not limiting and the same, or generally similar procedures, can be applied to peptides selected from other proteins to achieve desired changed in antigenicity.

TABLE 2

Figure 2:
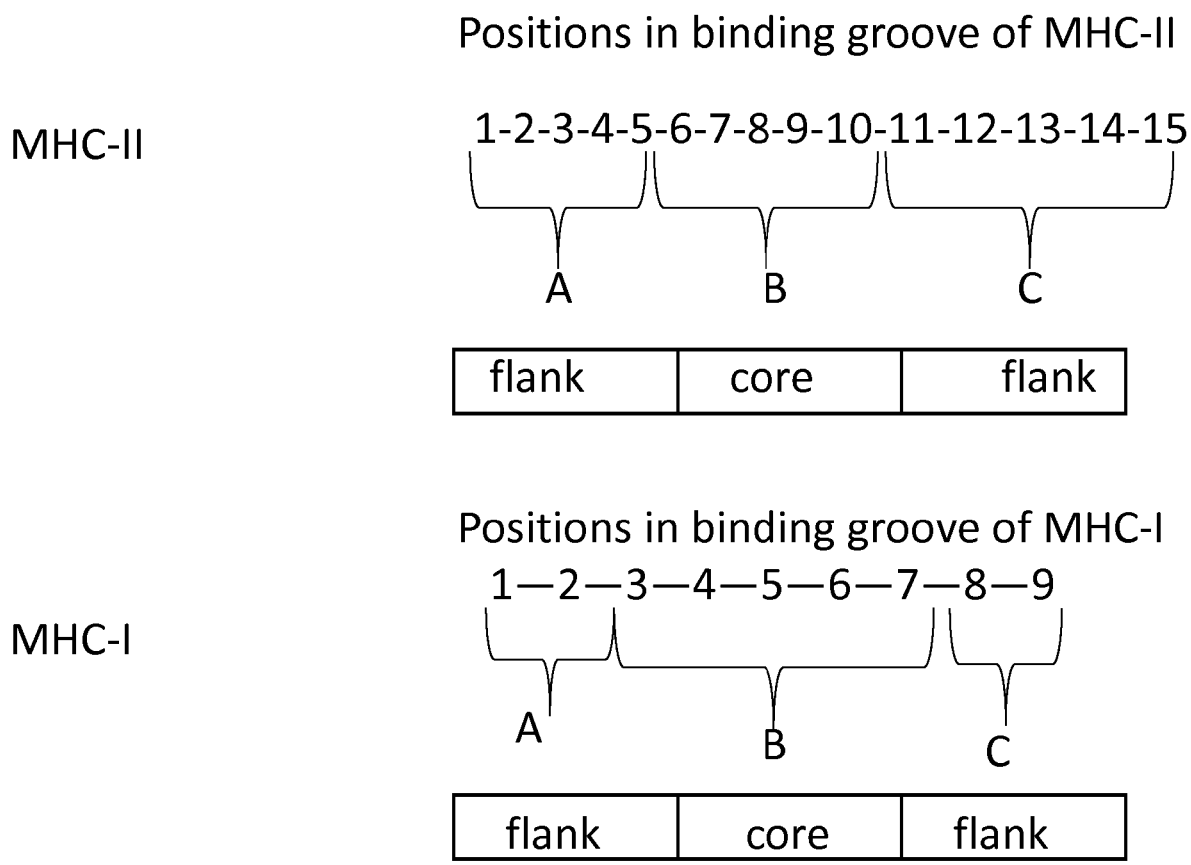
FIG. 2 illustrates the approach to optimization of a MHC binding peptide to achieve specific results. The central core 5 amino acids determine the T cell receptor binding; the flanking regions can be varied to change the MHC allele binding affinity. In the examples a combination of fixing and variation of the flanks (labeled as A and C) and core (labeled as B) are used.

| | Goal | Variations by Zone(as shown in FIG. 2) | | | Protein used in example |
|---|---|---|---|---|---|
| Example A | Increase affinity of MHC-II 15-mer | Flank Vary | Core Fix | Flank Vary | Ara h1 peanut allergen |
| Example B | Decrease antigenicity of MHC-II 15 mer | Flank Fix | Core Vary | Flank Fix | Immunoglobulin 1A9 heavy chain |
| Example C | Decrease antigenicity of MHC-II 15mer | Flank Fix Flank Vary | Core Fix Core Fix | Flank vary Flank Vary | Immunoglobulin 1A9 heavy chain |
| Example D | Increase binding affinity MHC-I 9 mer | Flank Vary | Core Fix | Flank Vary | Prostate specific Antigen |

Example 1 A

Maintaining the Core Sequence to Retain the T-Cell Recognition and Varying the Flanking Regions to Increase Predicted Binding Affinity to One or More MHC Alleles of Interest; Example Applied to Peanut Allergen Ara h1

The protein Ara h1 is a known allergen protein of peanuts. In this example, it is shown how the MHC binding of specific peptides can be increased by varying the flanking regions (Zone A and C) of a 15-mer.

A specific 15 mer peptide LNRHDNQNLRVAKIS (SEQ ID NO: 28415) from Ara h1 is modified to simultaneously increase the affinity for MHC-II alleles DRB1-0101 and DBR1-0301. The central 5 amino acids (zone B) are held constant as those are expected to be recognized by the T-cell receptor. For each flanking region (A and C) as 10 of 15 amino acids can be varied, there are $20^{10}$ possible variants. 10000 peptides were selected at random based on the overall frequency in the protein. The binding affinity based on the principal component analysis of each new 15 mer (A-B-C) was then evaluated to determine which peptide changes give increased affinity for the DRB alleles of interest while maintaining the core constant.

Figure 3:
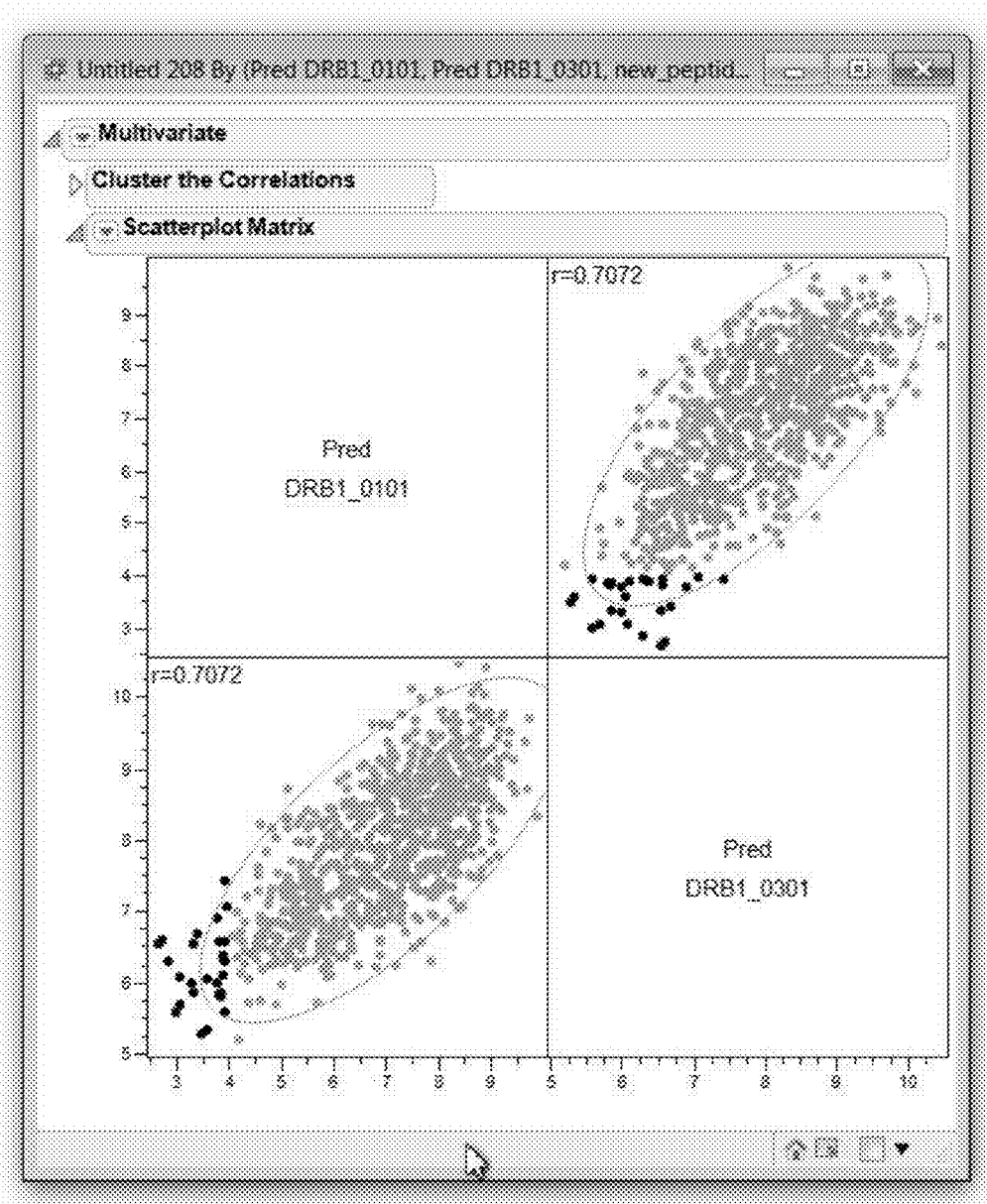
FIG. 3 shows the modification of the naturally occurring 15 mer peptide from peanut allergen Ara h1 LNRHDNQNLRVAKIS (SEQ ID NO: 28415) to maximize binding to two MHC-II alleles: DRB1*01:01 & DRB1*03:01. The right hand column in the table shows a subset of 10,000 peptides selected at random; this subset comprises 27 peptide variants, which have the same core 5 amino acids ~NQNLR~ (SEQ ID NO: 28424) and that offer the best binding to the two MHC alleles of interest. In the scatter plot showing all peptide variants tested the black dots show the best binders in the table. The ellipse is the 95% statistical confidence zone.
Figure 4:
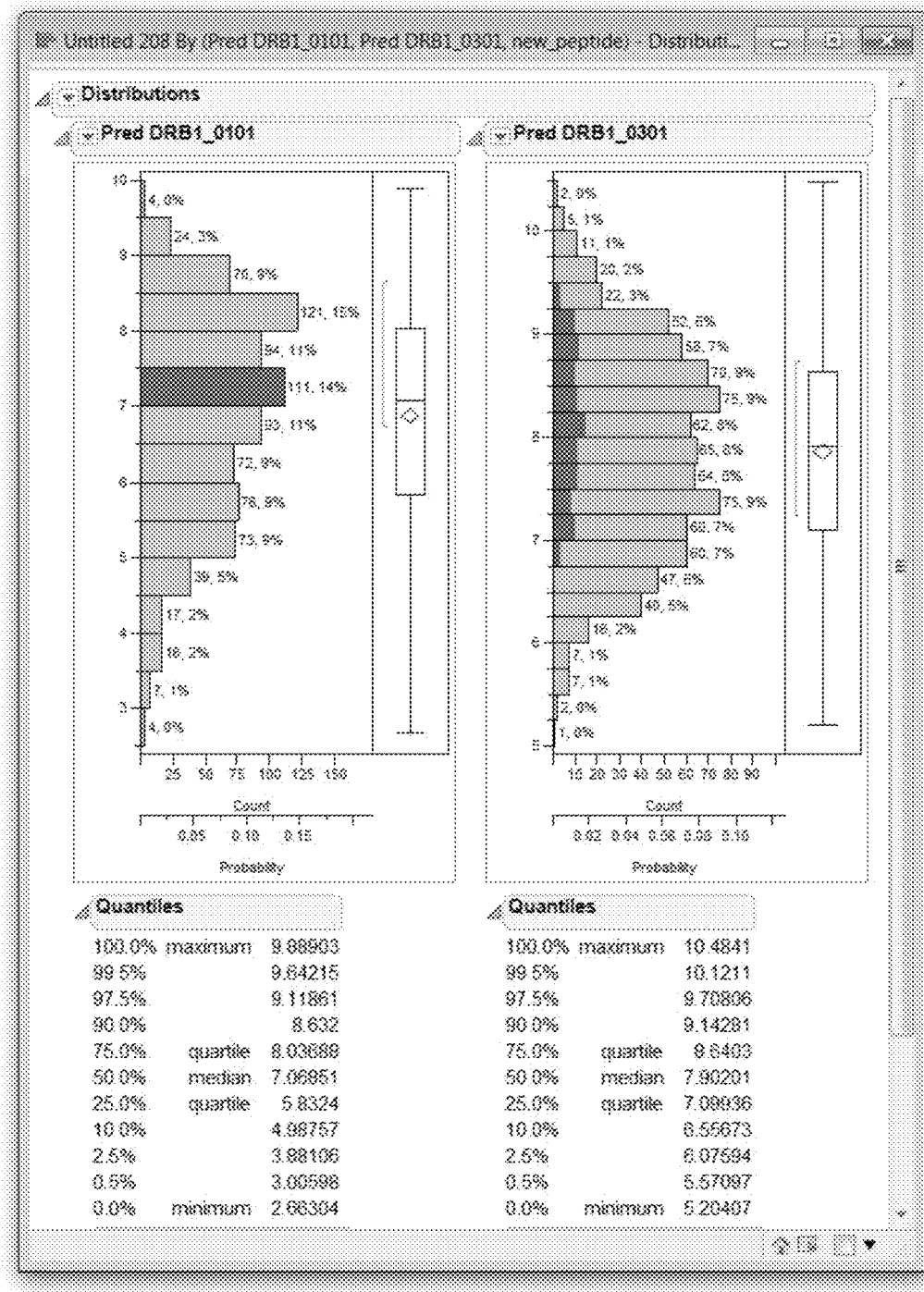
FIG. 4 shows that in the peanut allergen Ara h1 the selected peptide LNRHDNQNLRVAKIS (SEQ ID NO: 28415) in its native form is among 11 15 mer peptides that have a binding affinity for DRB1_0101 near the median for all 15mers in the parent protein. When the affinity of this subset is examined for binding to DRB1_0301 they are also seen to be within approximately the median 75% of binding affinity. In the right hand panel, the affinity of the best selected peptides shown in FIG. 46 is shown, lying in the highest 3% affinity for DRB1_0101 and the highest 15% for DRB1_0301.
Figure 4:
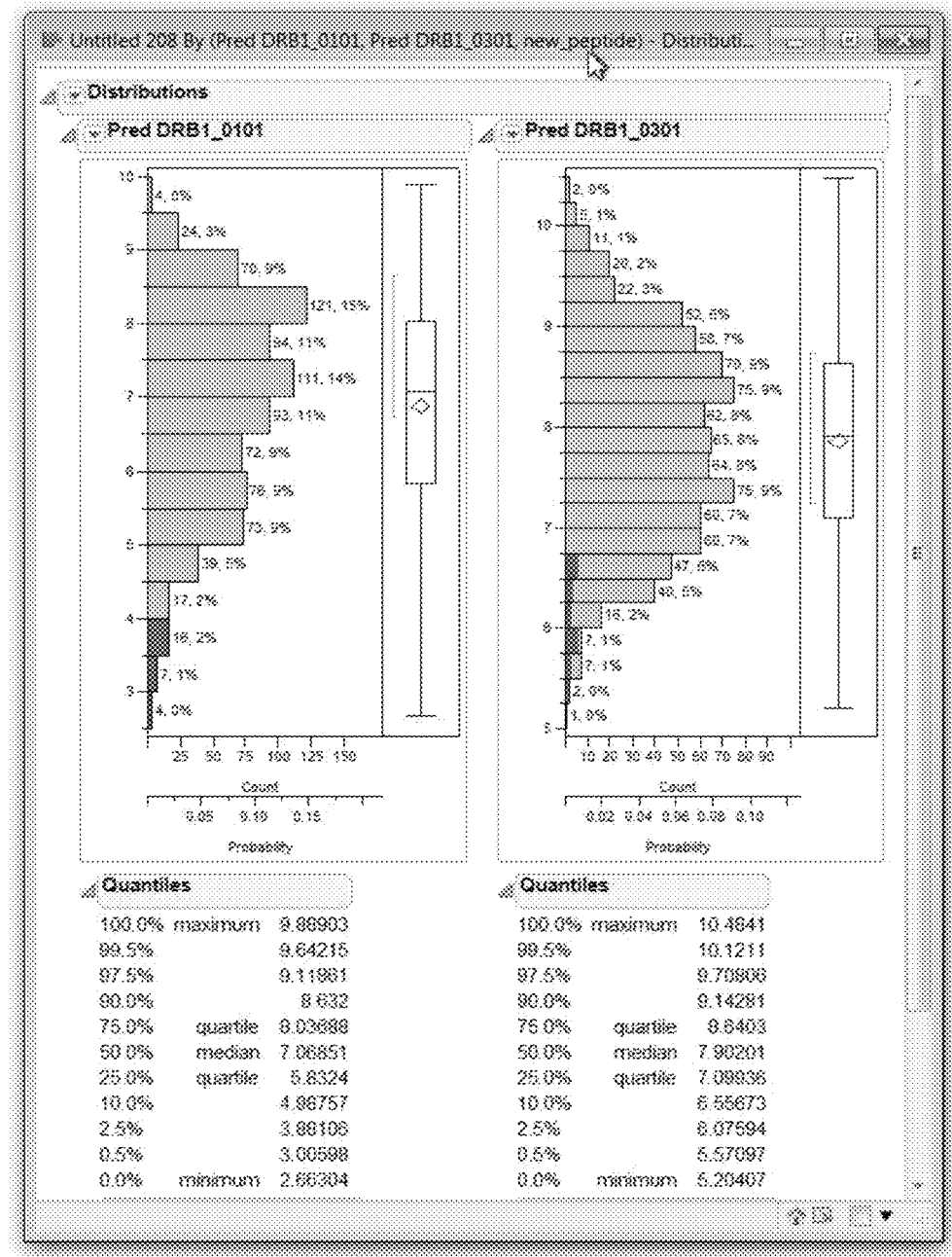

In FIGS. 3 and 4 the selected peptides are shown and their position as outliers of highest predicted binding affinity is shown. The predicted binding affinity of peptide LNRHDNQNLRVAKIS (SEQ ID NO: 28415) is found in the mid-region of the distribution and the peptides highlighted in these figures have an $e^3$ (approximately 20 fold) increase in predicted binding affinity for the two HLA alleles indicated. These are peptides suitable for testing as potential antigens for inducing anergy in individuals of this alleleic composition.

Example 1B

Maintaining the Flanking Sequences and the Binding to MHC Alleles of Interest while Varying the Core Region to Decrease Binding Affinity to T Cell Receptors: Application to an Immunoglobulin This example describes the reduction of recognition of a selected peptide by T cell receptors, while maintaining or increasing the predicted binding to, and occupancy of, MHC alleles of interest. This approach can be used, for example, to remove an adverse T cell stimulation to a biopharmaceutical protein molecule. In this instance the flanking 5mers (A and C in FIG. 2) are maintained constant and the core 5mer (B) is varied. The total possible permutations are $20^5$. A random 5000 5-mers are selected based on the amino acid frequency in the protein as a whole. Using principal component analysis the predicted binding affinity is determined.

Figure 5:
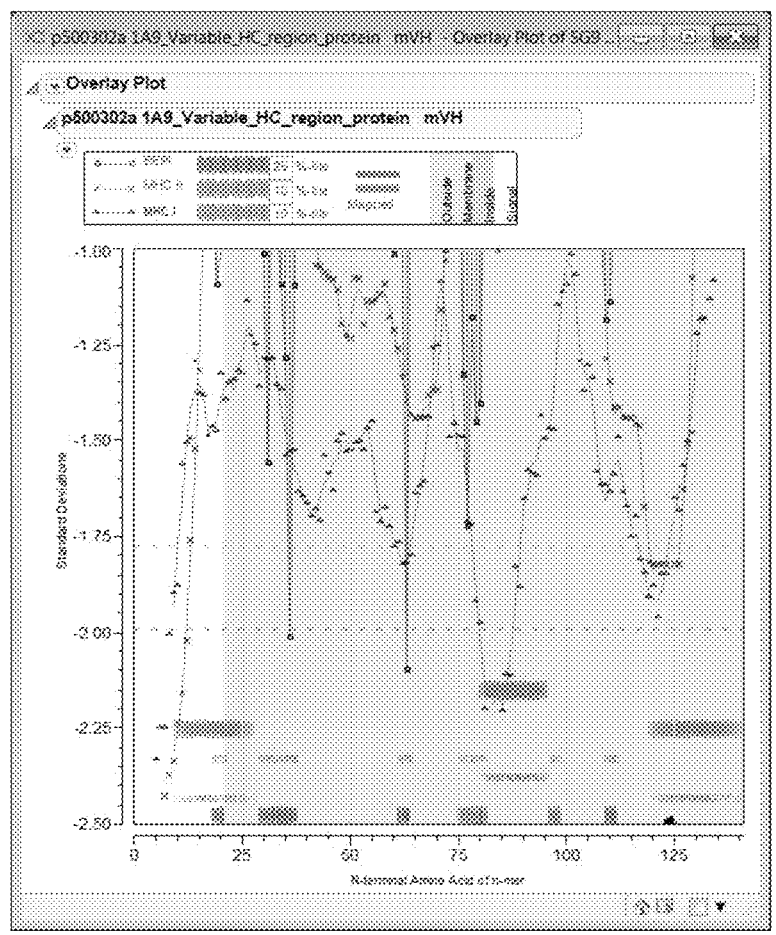
FIG. 5 shows (left hand panel) the permuted population average binding affinity of peptides in the heavy chain variable region of anti-cryptosporidial antibody 1A9. This plot was made using the methods described herein. The 15 mer peptide starting at position 124, which has a relatively high predicted binding affinity was selected for manipulation. The top right histogram shows the binding affinity of this peptide lies in the top 4% for DRB1_0101 and the top 12% for DRB1_0301 relative to all other 15 mer peptides in the parent protein. This high affinity is also shown in the scatterplot bottom right.
Figure 5:
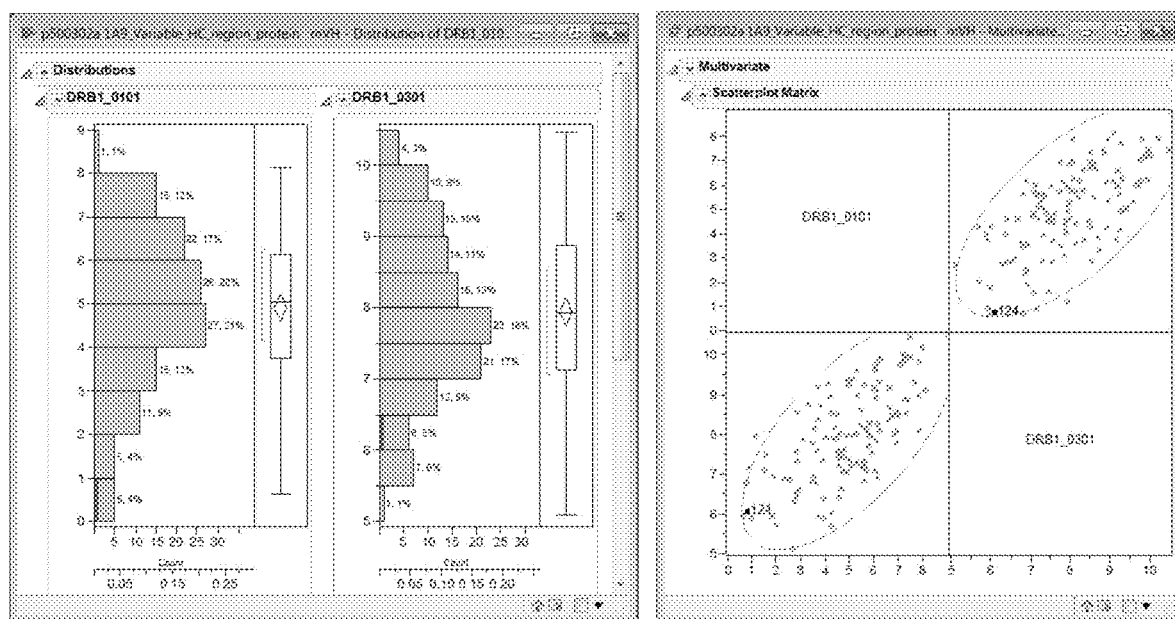
Figure 6:
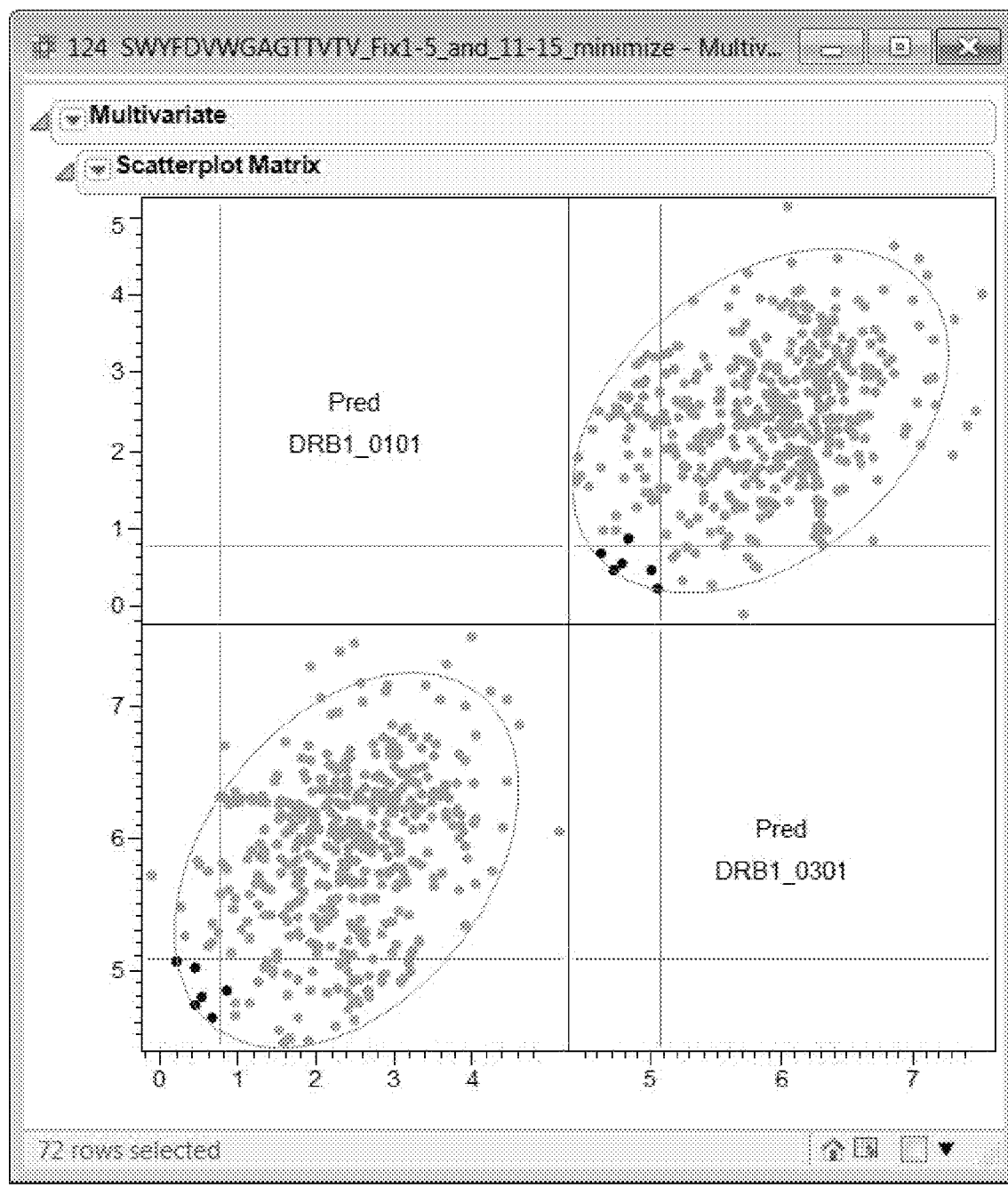
FIG. 6 shows that the 15mer peptide starting at 124 in heavy chain 1A9 has affinity for DRB1-0101 and DRB1_0301 lying at the intersection of the lines on the scatter plot. The black dots represent the alternative peptides selected in which the core 5 amino acids have been varied to change the T cell binding while maintaining the flanks unchanged. The scatter plot and histogram show the affinity for both of the selected peptides of interest are the same or higher as in the native peptide.
Figure 6:
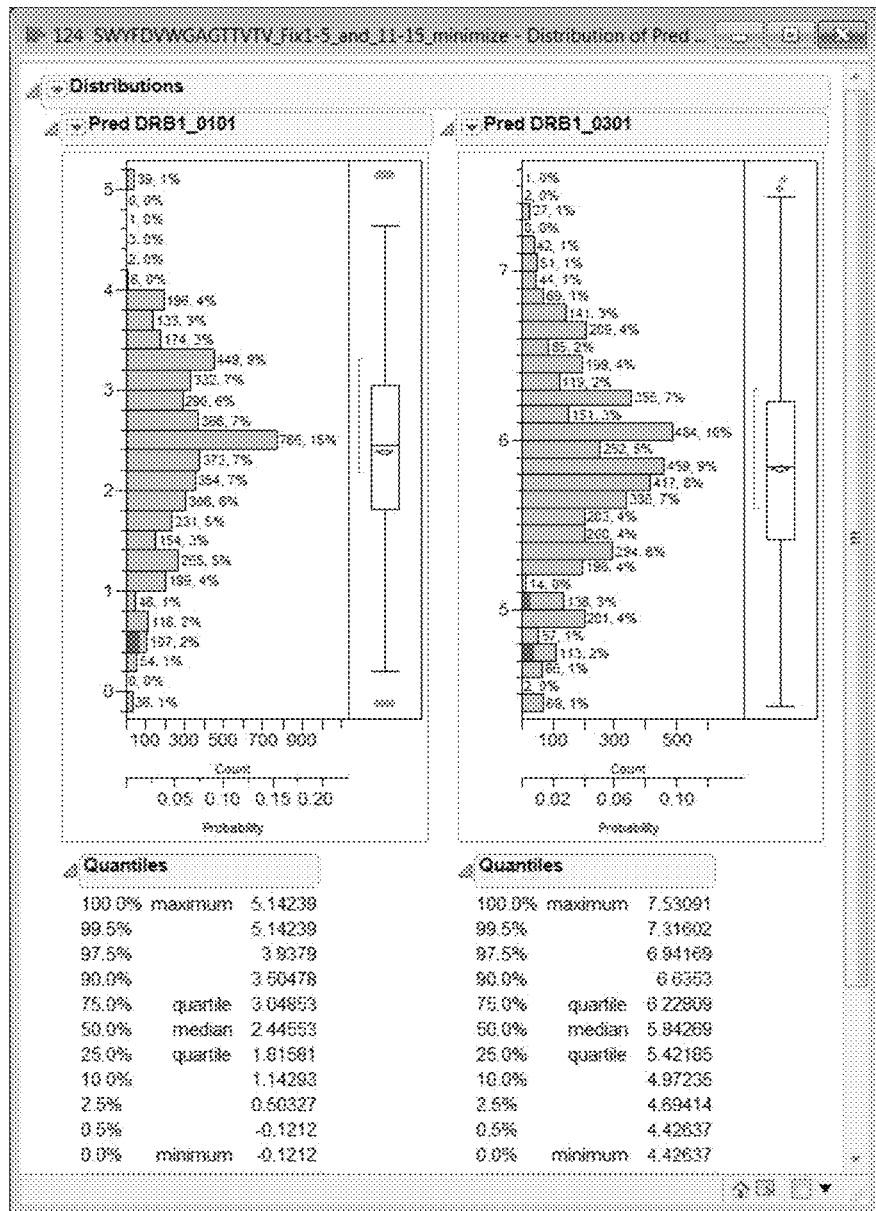
Figure 7:
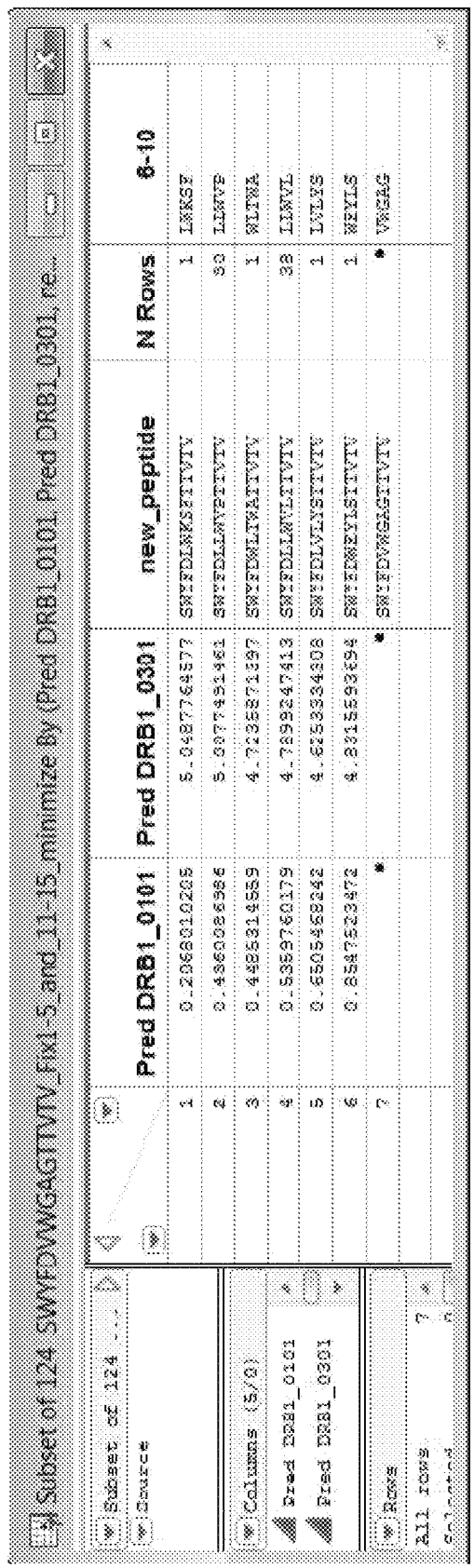
FIG. 7 shows that when a subset of 5000 15 mers variants of peptide 124 of antibody heavy chain variable region of 1A9 is used in which the flanks are fixed and core varied, 435 unique variants of the core 5 amino acids were generated, of which only 6 unique 5-mer variants met the criteria of maintaining high affinity binding for the alleles of interest, DRB1_0101 and DRB1_0301.

This example examined a selected peptide from the variable region of the heavy chain of an immunoglobulin 1A9. FIG. 5 shows the permuted distribution of predicted affinity to all peptides in this particular protein and shows histograms and scatter plot showing how the selected peptide, starting at position 124 a peptide that has a quite high predicted affinity for both of the target alleles, compares to other 15 mer peptides within the same protein, for two HLA alleles DRB1_0101 and DRB1_0301. The goal of the modification in this instance was to maintain the binding affinity for these MHC alleles the same or higher while changing the core 5mer. Of the possible $20^5$ variants, 5000 randomly optimized variants of the core 5-mer (B in FIG. 45) were generated based on the frequency of amino acids in the parent protein. This process produced 435 variants identified as unique (the random optimization process tends to identify certain peptides multiple times). Of these 435, 6 maintained affinity of binding to the MHC alleles of interest. Hence the selection process results in 6 peptides from the sample of 5000 that maintain or increase the binding to the MHC molecule but that are expected to bind to a corresponding T cell receptor more poorly if at all. These peptides are shown in FIGS. 6 and 7. In the scatterplot on FIG. 6 these are the dark peptides lying outside the lines showing the original binding affinity of peptide 124 to the two MHC alleles of interest. Each of the resultant 6 variants is then tested to determine the continued functionality of the protein of interest. The process described provides a rapid means of selecting candidates for testing that maintain all desired MHC binding characteristics. Effectively these 6 new peptides are epitope mimics of the original peptide.

Example 1C

Maintaining the Core Sequence and Varying Flanking Regions to Decrease Binding Affinity to One or More MHC Alleles of Interest: Application to an Immunoglobulin This example describes a method of reducing the predicted binding affinity of an MHC allele to one or more MHC alleles, thus reducing antigenicity. The approach is that of maintaining the core zone constant but changing the binding affinity of one or both flanking regions to vary how well the peptide is bound by the MHC molecule groove for the alleles of interest.

Figure 8:
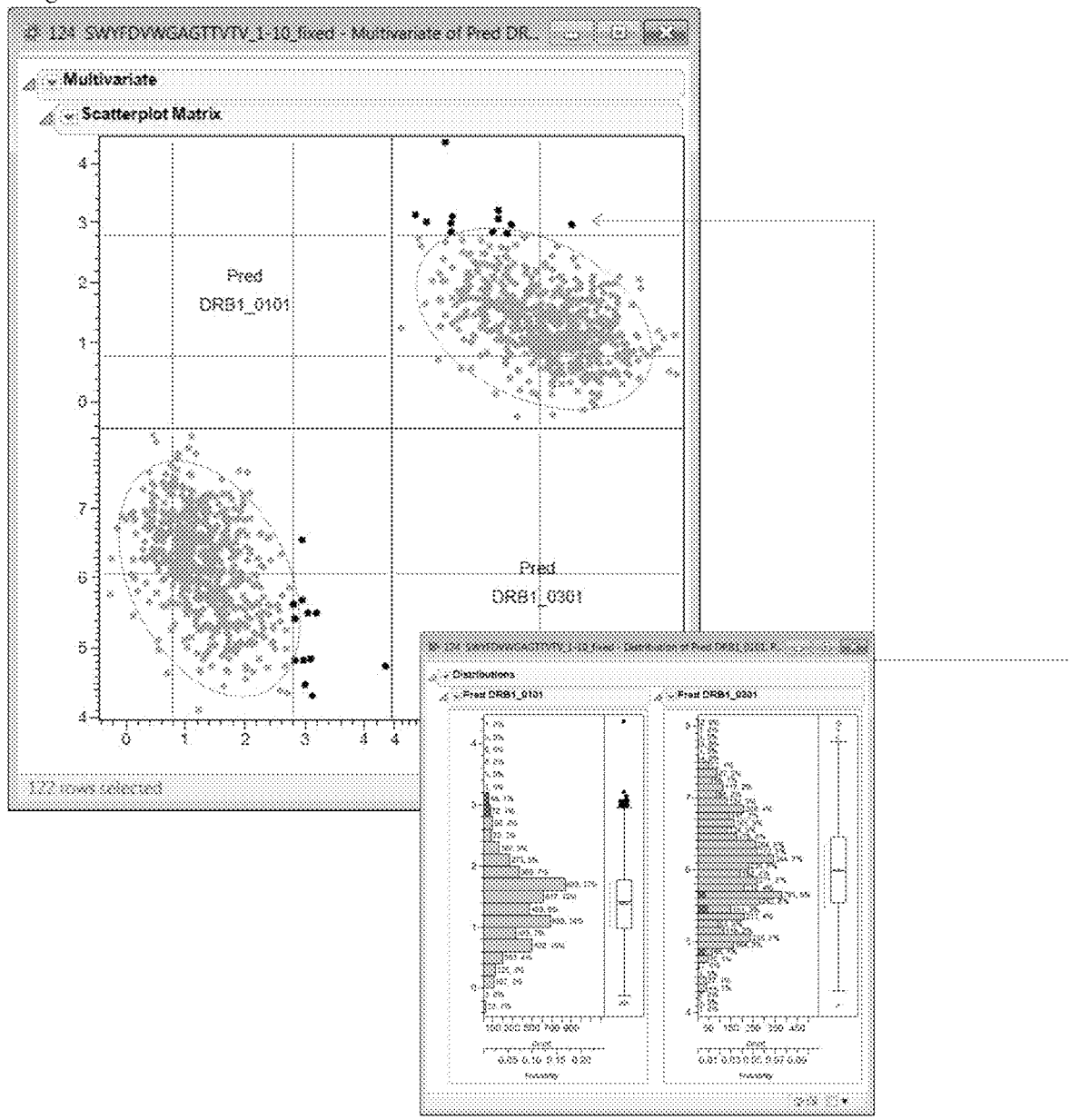
FIG. 8 shows a scatter plot of binding affinity of 15 mer peptides created by varying peptide 124 of antibody 1A9. The 5000 variants were created by holding amino acids 1-10 constant and varying the C terminal flank 5mer. The axes mark the binding affinity of the native peptide to DRB1_0101 and DRB1_0301. One variant peptide shows a higher binding affinity for both alleles and hence falls outside both axes.

Again using the 15 mer peptide initiating at amino acid position 124 of the heavy chain variable region of immunoglobulin 1A9, and maintaining 10 amino acids constant and varying the C terminal 5mer we evaluated the peptides which resulted in simultaneous reduced affinity for DRB1_0101 and DRB1_0301. As above, using a sample of 5000 peptides of the total $20^5$ possibilities, it would found that one variant resulted in a decreased affinity for DRB1_0101 (from $e^{0.8}$ to $e^{2.8}$) and simultaneously decreased affinity for DRB1_0301. Hence this method resulted in peptides that offered lower binding affinity and thus antigenicity. This is shown in FIG. 8.

Figure 9:
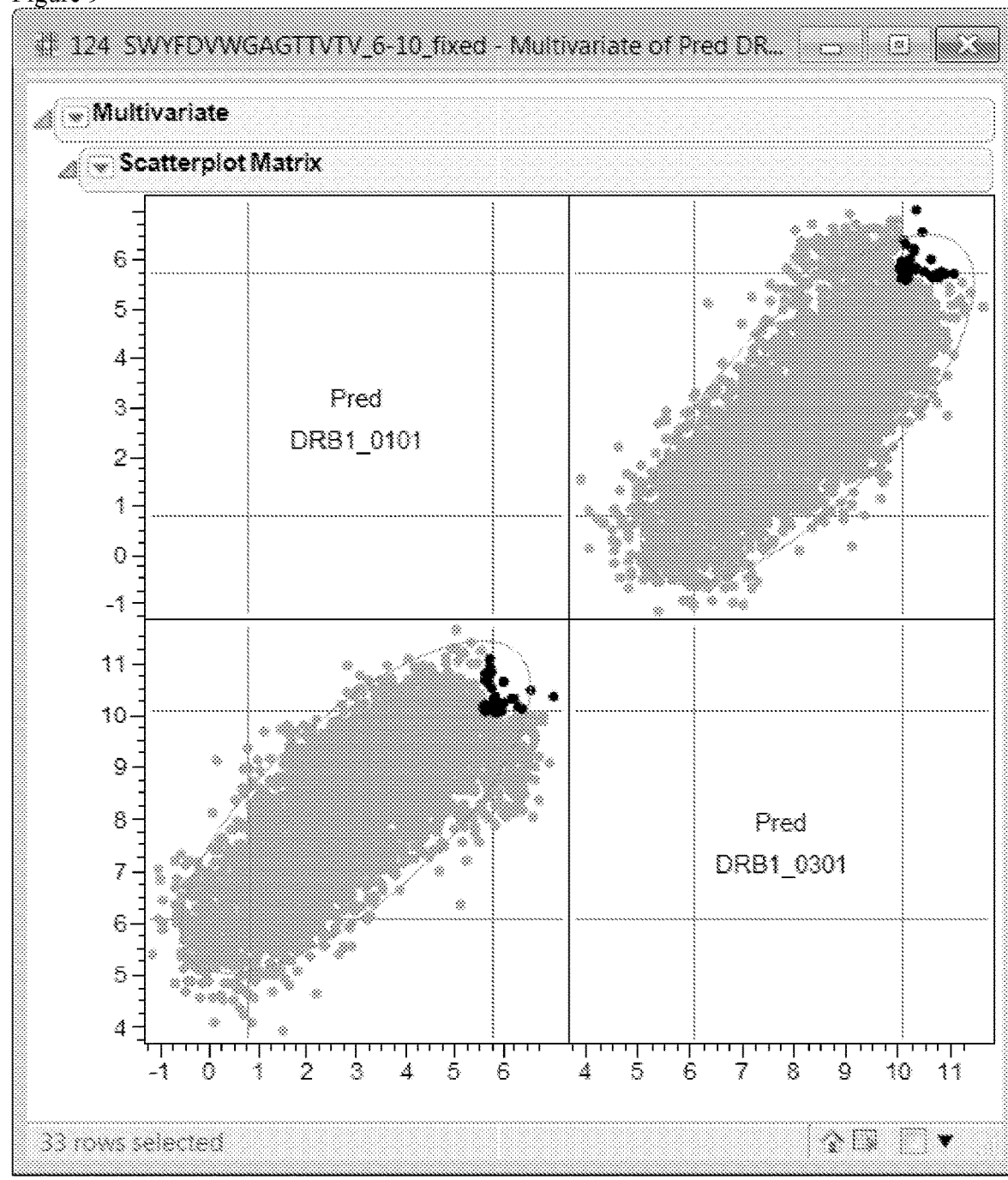
FIG. 9 shows a scatter plot of binding affinity of 15 mer peptides created by varying peptide 124 of antibody 1A9. The 5000 variants were created by holding amino acids 6-10 constant and varying both terminal flank 5mers. The axes mark the binding affinity of the native peptide to DRB1_0101 and DRB1_0301. In this case, 33 variant peptides are generated that show a higher binding affinity for both alleles and hence fall outside both axes.

When both flanking 5 mers were varied it was possible to generate 33 peptides from a sample of 5000 peptides, which had reduced binding for both alleles. In this case the 33 peptides achieved an $e^5$ reduction (148 fold lower) in binding for DRB1_0101 and an e4 (approximately 55 fold) reduction in binding for DRB1_0301. This is shown in FIG. 9.

Example 1D

Figure 10:
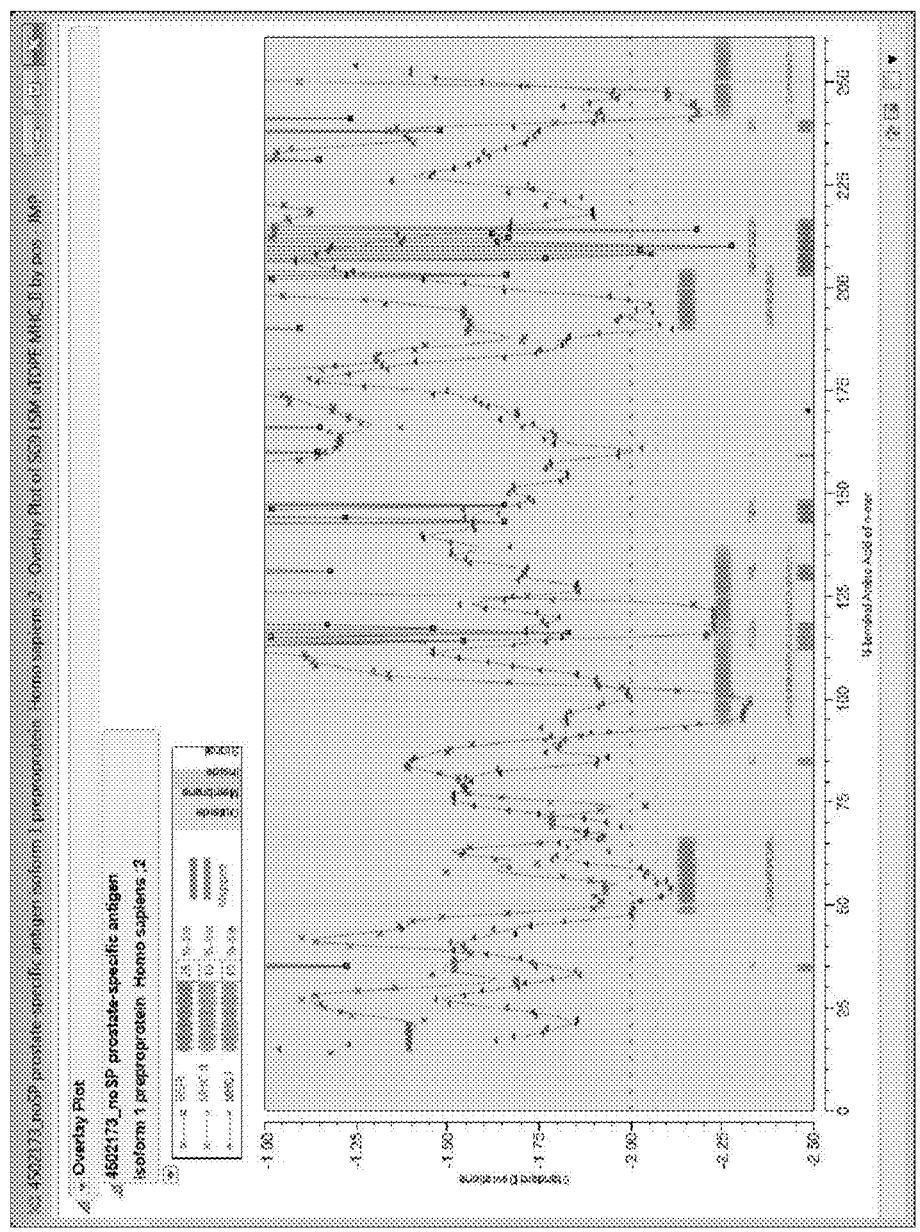
FIG. 10 shows the permuted population average binding affinity of peptides in the prostate specific antigen protein isoform 1 (PSA). This plot was made using the methods described herein. The 9 mer peptide starting at position 74 was selected for manipulation.
Figure 11:
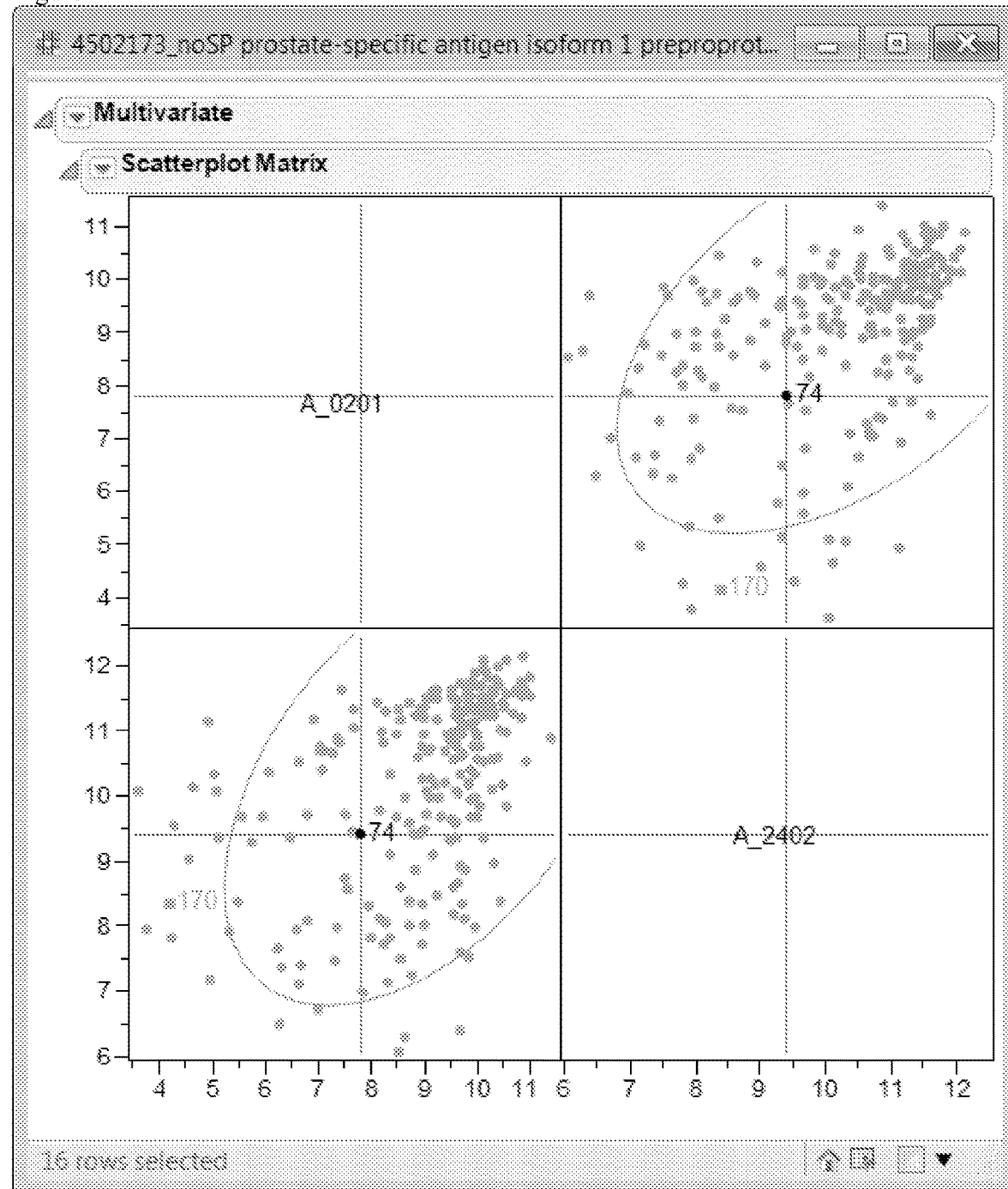
FIG. 11 shows the predicted binding affinity to MHC I alleles A_0201 and A_2402 of the 9 mer starting at position 74 in PSA relative to other 9mers in the parent protein. The intersection of the axes marks the binding affinity to both alleles. The gray dots are the affinities of all of the other peptides in the protein.
Figure 12:
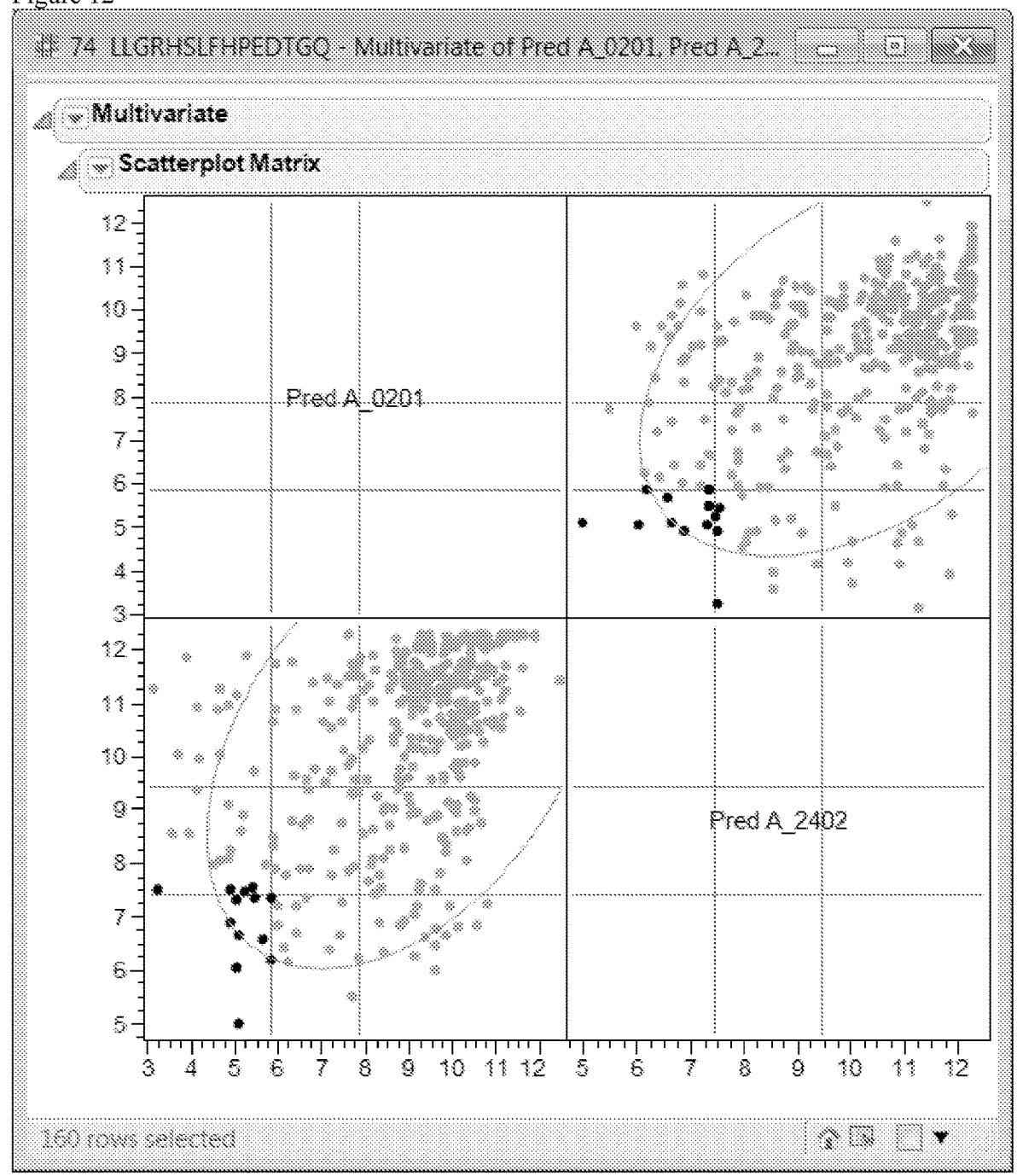
FIG. 12 shows the predicted binding affinity to MHC I alleles A_0201 and A_2402 of selected variants of the 9 mer starting at position 74 in PSA relative to other 9mers in the parent protein. The variants were the from among 5000 random combinations derived from the position 74 9 mer in which the core 5 mer was fixed and the two 2-mer flanking regions were varied to increase affinity. The selected peptides lie outside intersection of the axes marking the binding affinity to both alleles and have an $e^2$ (7.4 fold) increase in affinity.
Figure 13:
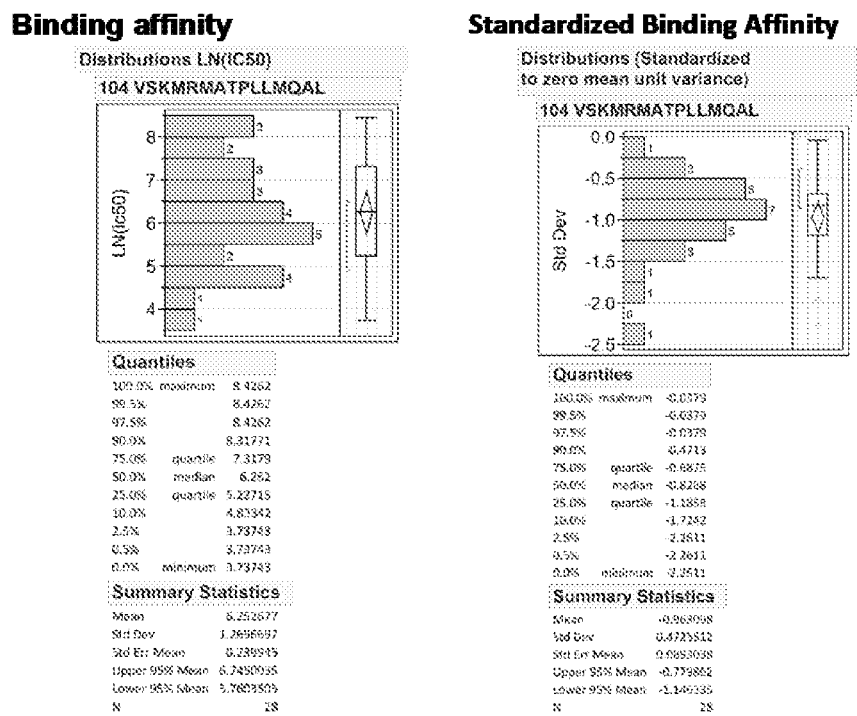
FIG. 13 shows the statistical characteristic of the primary CLIP peptide in the context of a canonical 15-mer for 28 human MHC II alleles. CLIP peptide binds to many different MHC II molecules with a moderate affinity of about e6.26=525 nM equivalent to about $-0.96\sigma$ (approx $-1\sigma$) below the mean.
Figure 14:
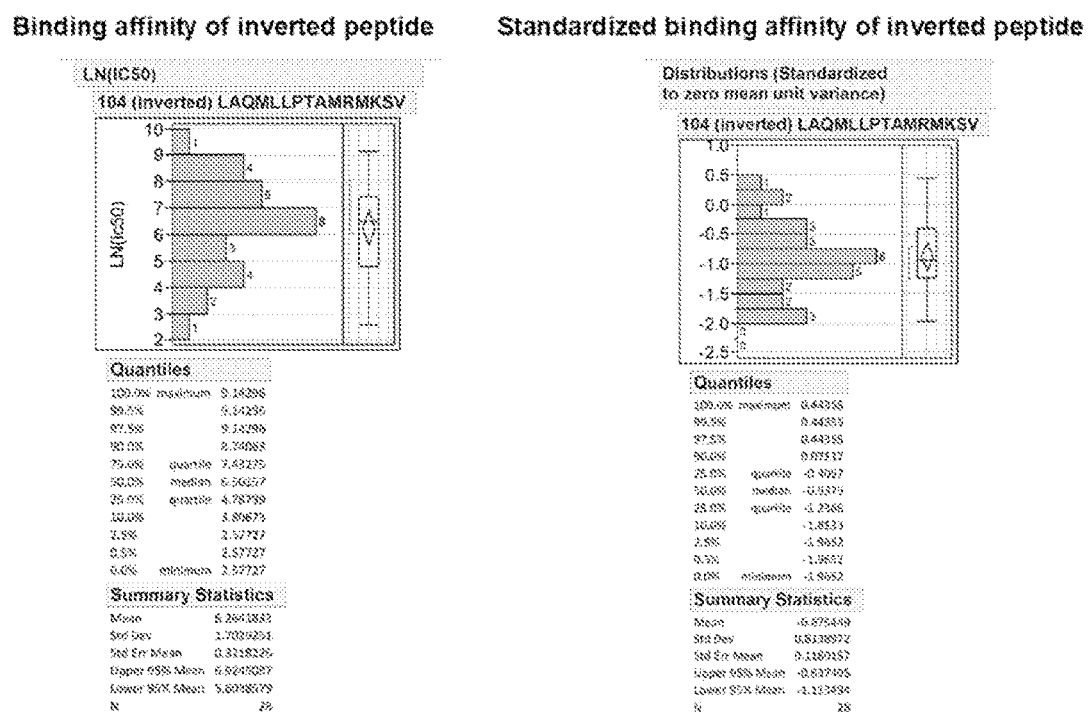
FIG. 14 shows the statistical characteristic of the inverted CLIP peptide in the context of an inverted (non-canonical) 15-mer for 28 human MHC II alleles.
Figure 16:
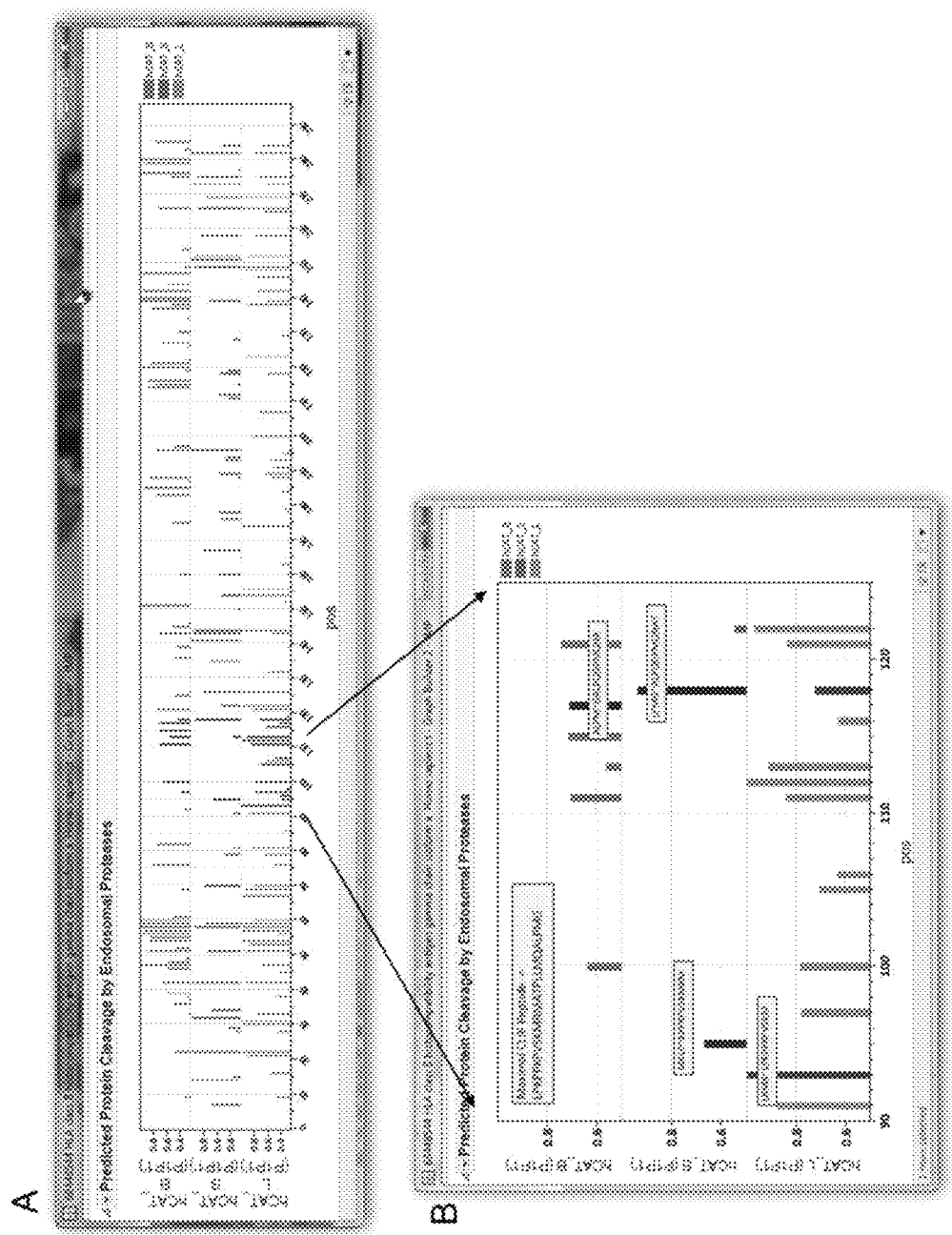
FIG. 16 shows the probability of cleavage by cathepsin B, S, L in HLA class II histocompatability antigen isoform A. Panel A shows the probability of cathepsin cleavage along the whole protein. Panel B expands the detail for amino acid positions 90-120. Highlighted (darker color bars) cleavage points are high yield promiscuous self peptides reported by Chicz et al 1993 (see Table 6 in reference) and shown in the inserted labels.

Maintaining the Core Sequence and Varying Flanking Regions to Increase Binding Affinity to One or More MHC-I Alleles of Interest In this example a 9 mer peptide was selected from prostate specific antigen. The goal was to increase the binding affinity simultaneously to two MHC 1 Alleles, A*0201 and A*2402. FIG. 10 shows the permuted plot of binding affinity within this protein. A 9 mer peptide starting at amino acid 74 was selected: LLGRHSLFH (SEQ ID NO: 28416). This was envisioned as a core (B) 5 mer and two flanking regions of 2 amino acids each. FIG. 11 shows the binding affinity to the alleles of interest of the native peptide 74. Variation of the two flanking regions provides a possible $20^4$ variants. A sample of 5000 variants yielded 396 unique variants of which 13 were shown to have an affinity of $e^2$ or more (i.e. 7.4 fold higher) than the native peptide 74. FIG. 12 shows the relative binding affinity of the resultant peptides to the alleles of interest.

Example 2

Treatment with Specific MHC Binding Peptides to Reduce Immune Reaction

Many biopharmaceutical proteins induce adverse or inhibitory acquired immune responses. By applying the analysis described herein it is possible to identify specific peptides that are highly antigenic for a specific group of HLAs. In some cases, when a T cell epitope is administered and presented as an immunogen in isolation and in increasing doses, in the absence of co-stimulatory stimuli, anergy may be induced. This is the approach taken in developing vaccines for allergens.

The array of predicted MHC binding affinity of all peptides within a biopharmaceutical of interest is identified. Specific peptides of predicted high affinity binding to specific MHC and therefore of high immunogenic potential for individuals of that immunogenetic allelic make-up are identified. These peptides are expressed as 9-mers, 15-mers or such peptides plus short flanking regions and administered to a patient prior to the administration of the biopharmaceutical from which they are derived. Typically such administration would be initiated 2-4 weeks prior to treatment with the biopharmaceutical and in multiple repeated doses with the intent of inducing anergy to the epitopes. However in some instances where a biopharmaceutical is administered to treat an acute disease (for example a sepsis) the peptides are administered at the same time as the biopharmaceutical.

In some instances the biopharmaceutical is an antibody or an antibody fusion. In other instances the biopharmaceutical is a replacement therapy (e.g., a blood clotting factor) of other protein drug. Additional peptides or polypeptides can be utilized with the compositions and methods described herein.

In some instances the native peptide is enhanced as an anergen by modifying the flanking regions of the MHC binding protein (amino acids 1-5 and 11-15 in the case of a MHC-II binding 15 mer or amino acids 1-2 and 8-9 in the case of a MHC-I binding 9-mer). Such modification is conducted by simulation of peptides with increased binding affinity to the MHC of alleles of interest and construction of the higher binding peptides.

Example 3

This Example provides additional epitope sequences developed by the processes of the present invention for *Brucella* species.

*Brucella* spp. are small, Gram negative bacteria which are intracellular and persist inside macrophages. Brucellosis has long been recognized in ruminant animals and swine and is a major cause of reproductive problems in livestock including abortions. *Brucella* bacteria are shed in milk and placental fluids and are highly infectious to humans. Species infecting domestic livestock are *B. melitensis* (goats and sheep), *B. suis* (pigs), *B. abortus* (cattle and bison), *B. ovis* (sheep), and *B. canis* (dogs). *B. abortus* also infects bison and elk in North America and *B. suis* is endemic in caribou. *Brucella* species have also been isolated from several marine mammal species.

Brucellosis, also called Bang's disease, Crimean fever, Gibraltar fever, Malta fever, Mediterranean fever, r, or undulant fever remains the most prevalent zoonosis worldwide (WHO/DFID-AHP Meeting with the participation of FAO and OIE. WHO/SDE/FOS/2006.1; Pappas G, et al (2006) The new global map of human brucellosis. Lancet Infect Dis 6: 91-99). Brucellosis is a debilitating chronic disease for those naturally infected through exposure to bacteria in milk and placental fluids of ruminant livestock (Corbel M J (1997) Brucellosis: an overview. Emerg Infect Dis 3: 213-221). As infection also occurs by inhalation of aerosols and the infective dose is low, *Brucella melitensis* is a potential bioterror agent with capacity to infect large numbers of people (Kaufmann A F, et al (1997) The economic impact of a bioterrorist attack: are prevention and post-attack intervention programs justifiable? Emerg Infect Dis 3: 83-94); less deadly but far more costly than an anthrax attack. *B. suis* has similar bioweapon potential. No effective vaccine exists to protect humans from brucellosis. Several weeks of antibiotic treatment are required, but may be unable to clear residual foci of bacteria. Historically, vaccines developed to control disease in cattle, sheep, and goats, the main natural reservoir of *B. melitensis*, comprise live attenuated *Brucella* organisms, still capable of causing disease in humans. Killed organisms are ineffective vaccines. DNA and subunit recombinant vaccines, offer potential safety, but have yet to provide long lasting protection or broad coverage. A safe and effective vaccine suitable for human use is needed to protect those facing occupational exposure, and to provide large scale protection and post-exposure intervention in the face of deployment of brucellosis as a bioterror weapon. Effective brucellosis vaccines would greatly benefit populations of highly endemic regions and would aid in reducing prevalence in the livestock reservoir.

The complete proteome sequences for multiple *Brucella* species were downloaded from patricbrc.org or Genbank and analyzed according to the methods described herein. The 54 species analyzed are shown in Table 17.

TABLE 17

Species and strains of *Brucella melitensis*, *B.suis* and *B.abortus* analyzed

| Genome Name | Genome Status | PATRIC CDS | Isolation Country | Host Name | Collection Date |
|---|---|---|---|---|---|
| *Brucella abortus* 104M | WGS | 3303 | China | | |
| *Brucella abortus* A13334 | Complete | 3308 | South Korea | cattle | |
| *Brucella abortus* NCTC 8038 | WGS | 3439 | | | |
| *Brucella abortus* S19 | Complete | 3476 | | | 1923 |
| *Brucella abortus* bv. 1 str. 134 | WGS | 3298 | China | Homo sapiens | 2001 |
| *Brucella abortus* bv. 1 str. 9-941 | Complete | 3476 | | | |
| *Brucella abortus* bv. 1 str. BCB013 | WGS | 3255 | China | Bos taurus | 2010 |
| *Brucella abortus* bv. 1 str. BCB027 | WGS | 3203 | China | Ovis aries | 1983 |
| *Brucella abortus* bv. 1 str. NI010 | WGS | 3301 | | | |
| *Brucella abortus* bv. 1 str. NI016 | WGS | 3307 | | | |
| *Brucella abortus* bv. 1 str. NI021 | WGS | 3304 | | | |
| *Brucella abortus* bv. 1 str. NI259 | WGS | 3314 | | | |
| *Brucella abortus* bv. 1 str. NI435a | WGS | 3300 | | | |
| *Brucella abortus* bv. 1 str. NI474 | WGS | 3309 | | | |
| *Brucella abortus* bv. 1 str. NI486 | WGS | 3309 | | | |
| *Brucella abortus* bv. 1 str. NI488 | WGS | 3297 | | | |
| *Brucella abortus* bv. 2 str. 86/8/59 | WGS | 3574 | | bovine | 1959 |
| *Brucella abortus* bv. 2 str. BCB034 | WGS | 3305 | China | Homo sapiens | 2000 |
| *Brucella abortus* bv. 3 str. Tulya | WGS | 3521 | | | |
| *Brucella abortus* bv. 4 str. 292 | WGS | 3429 | | bovine | 1960 |
| *Brucella abortus* bv. 5 str. B3196 | WGS | 3473 | | | |
| *Brucella abortus* bv. 6 str. 870 | WGS | 3435 | | | |
| *Brucella abortus* bv. 9 str. C68 | WGS | 3406 | | | |
| *Brucella abortus* str. 2308 A | WGS | 3473 | | | |
| *Brucella melitensis* 16M13W | WGS | 3283 | | | |
| *Brucella melitensis* 16M1W | WGS | 3312 | | | |
| *Brucella melitensis* ATCC 23457 | Complete | 3486 | | Homo sapiens | |
| *Brucella melitensis* M28 | Complete | 3366 | | | |
| *Brucella melitensis* M5-10 | WGS | 3350 | China | | |
| *Brucella melitensis* M5-90 | Complete | 3347 | | | |
| *Brucella melitensis* NI | Complete | 3321 | China | cattle | |
| *Brucella melitensis* biovar Abortus 2308 | Complete | 3467 | | | |
| *Brucella melitensis* bv. 1 str. 133 | WGS | 3327 | China | Homo sapiens | 1998 |
| *Brucella melitensis* bv. 1 str. 16M | Complete | 3499 | | Homo sapiens | |
| *Brucella melitensis* bv. 1 str. 16M [WGS] | WGS | 3538 | | | |
| *Brucella melitensis* bv. 1 str. BCB028 | WGS | 3335 | China | Ovis aries | 1956 |
| *Brucella melitensis* bv. 1 str. BCB033 | WGS | 3346 | China | Homo sapiens | 2006 |
| *Brucella melitensis* bv. 1 str. M111 | WGS | 3331 | | | |
| *Brucella melitensis* bv. 1 str. M28-12 | WGS | 3331 | China | sheep | |
| *Brucella melitensis* bv. 1 str. M5 | WGS | 3335 | | | |
| *Brucella melitensis* bv. 1 str. Rev.1 | WGS | 3440 | | | |
| *Brucella melitensis* bv. 2 str. 63/9 | WGS | 3447 | | | |
| *Brucella melitensis* bv. 3 str. 128 | WGS | 3347 | China | Homo sapiens | 1986 |
| *Brucella melitensis* bv. 3 str. Ether | WGS | 3457 | | | |
| *Brucella suis* 1330 | Complete | 3432 | | swine | |
| *Brucella suis* ATCC 23445 | Complete | 3591 | | | |
| *Brucella suis* S2-30 | WGS | 3335 | China | | |
| *Brucella suis* VBI22 | Complete | 3292 | | | |
| *Brucella suis* bv. 1 str. BCB025 | WGS | 3223 | China | Sus scrofa | 2001 |
| *Brucella suis* bv. 1 str. S2 | WGS | 3289 | | | |
| *Brucella suis* bv. 2 str. BCB032 | WGS | 3272 | China | Sus scrofa | 2008 |
| *Brucella suis* bv. 3 str. 686 | WGS | 3515 | | | |
| *Brucella suis* bv. 4 str. 40 | WGS | 3388 | Soviet Union | reindeer | |
| *Brucella suis* bv. 5 str. 513 | WGS | 3377 | | | | bv = biovar
str = strain

A determination was made of the proteins which are conserved or near conserved across these species. Protein sequences were selected using 2 criteria (a) those contained in Figfams present in all 54 strains and which were represented in the *B. melitensis* 16M reference strain by a single representative; (b) an additional group of 7 proteins which had been previously identified by experimental means to induce interferon gamma and which were not present in group (a).

High affinity MHC-I and MHC-II binding peptides and high probability B-cell epitope sequences were determined.

MHC I and MHC II binding data were first standardized to zero mean and unit variance and then for each peptide in the protein sequence the highest binding affinity of combinations of allelic pairs was computed. Finally all possible combinations of alleles were averaged to represent a population phenotype for each particular peptide in the protein sequence. The population-permuted metric over protein sequences was found to be normally distributed and the peptides selected covered regions within the proteins of predicted highest affinity within that protein—the tenth percentile and one percentile highest affinity peptides. BEPI regions were selected based on the 25th percentile Bayesian probability for predicted B-cell epitopes based on a NN predictor trained with a large dataset of BepiPred 1.0 output for 100 randomly selected proteins.

The following table summarizes the output: Table 18 shows the number of peptides identified which fulfill the criteria established.

TABLE 18

| Species | Class | Type | First SEQ number | Last SEQ number | Number |
|---|---|---|---|---|---|
| *Brucella* spp | Membrane | BEPI | 1 | 335 | 335 |
| | | MHC_I | 336 | 537 | 202 |
| | | MHC_I_top 1% | 538 | 563 | 26 |
| | | MHC_II | 564 | 676 | 113 |
| | | MHC_II_top 1% | 677 | 690 | 14 |
| | Other | BEPI | 691 | 14805 | 14115 |
| | | MHC_I | 14806 | 22134 | 7329 |
| | | MHC_I_top 1% | 22135 | 23080 | 946 |
| | | MHC_II | 23081 | 27439 | 4359 |
| | | MHC_II_top 1% | 27440 | 27857 | 418 |
| | Secreted | BEPI | 27858 | 28153 | 296 |
| | | MHC_I | 28154 | 28299 | 146 |
| | | MHC_I_top 1% | 28300 | 28314 | 15 |
| | | MHC_II | 28315 | 28398 | 84 |
| | | MHC_II_top 1% | 28399 | 28404 | 6 |

Example 4

Binding Characteristics and Cleavage of the CLIP Peptides

The "CLIP" peptide (MHC Class II invariant peptide) is produced by endosomal cleavage of the MHC gamma, also known as the "invariant chain". The MHC-gamma allele is one of the genes in the MHC locus and has substantial structural similarity to the MHC molecules. It appears to have two purposes: First, a portion of the molecule binds in the molecular groove of the MHC II molecule and is used as a chaperone for guiding the MHC II molecule in the endosomal compartment where peptide loading takes place. Second, the CLIP peptide when released by endosomal peptidase activity, binds only with a moderate binding affinity to many different MHC II alleles and serves as a placeholder for other peptides that will be loaded into the MHC molecule in its place with the assistance of MHC-DM for ultimate presentation on the surface of the antigen presenting cell.

Experimental evidence shows that the so-called "CLIP peptide" is not a single peptide but actually a group of peptides with slightly different lengths (ragged ends) produced by differential endosomal peptidase cleavage activity. The longest of these peptides has the sequence LPKPPKPVSKMRMATPLLMQALPMG ((SEQ ID NO: 28417). The underlined sequence has been shown in experiments by others (Chicz R M et al, 1993 J Exp Med., Specificity and Promiscuity among Naturally Processed Peptides Bound to HLA-DR Alleles; Villadangos, J A et at 1997, J Exp Med, Degradation of Mouse Invariant Chain: Roles of Cathepsins S and D and the Influence of Major Histocompatability Complex Polymorphism) to be the primary binding region. It has the characteristic of binding to many different MHC II molecules (so is sometimes called a promiscuous peptide) with what is generally considered a moderate affinity of about e6.26=525 nM equivalent to about −0.96σ (approx −1σ) below the mean (FIG. 13). In fact, the neural net (NN) predictions suggest that several different binding registers will bind with a very similar binding affinity (IC50). An interesting feature of this molecule was determined recently where new experiments (Schlundt, A. 2012, J Mol. Biol Peptide Linkage to the alpha Subunit of MHC II Creates a Stably Inverted Antigen Presentation Complex) suggest that the peptide can bind, not only in the standard or canonical N ◇ C orientation, but also in the reverse C ◇ N orientation. Interestingly, the NN predictions for binding of the reverse peptide are also very comparable to the canonical orientation. As can be seen in FIG. 14, for several binding registers the affinity is actually higher for the inverted orientation that the canonical. A caveat to this observation is that the experimental procedures that are used to estimate the binding affinity to an MHC molecule are a bulk measurement done without knowledge of which orientation the peptides are assuming. It could be that the molecule assumes N ◇ C orientation or a C ◇ N or a mixture of the two. FIG. 15 shows the predicted binding affinity in several different binding registers for the canonical and inverted peptide orientation for a single common human MHC II allele (DRB1*01:01). The results are typical of those we have seen for the other 27 human alleles, as well as those from other species such as the mouse.

It follows that peptides from proteins of other derivations (including but not limited to microbial, mammalian, insect, allergen, etc.) may also be bound to MHC molecules in canonical or non-canonical orientation and thus may be presented by MHC as T cell epitopes in either orientation.

Furthermore, with reference to CLIP, the experimental determinations (Chicz et at vide infra) of peptide presentation by MHC molecules on antigen presenting cells provided a system for independent verification of the cathepsin cleavage predictions. The peptides presented on the MHC molecules at the cell surface should have been excised by the endosomal peptidases. Therefore the NN cleavage predictions for the endosomal peptidases, cathepsin B, L and S were compared to the N and C termini of the presented peptides. The cleavage predictions were found to be highly concordant with peptides attached to MHC II molecules and which had been detected by mass spectrometry. The endosomal peptidases are quite aggressive enzymes and cleave at a wide variety of amino acid sequences. Consistent with this, several different cleavage positions are predicted in this vicinity of the CLIP peptide molecule. The median length of peptide eluted and detected by mass spectrometry is 17 amino acids or two amino acids longer than the 15-mer binding pocket in the MHC II molecule generally recognized. The results of this Comparison are shown in FIG. 16. The experiments were carried out with virus transformed human B cells and in this cell type cathepsin S is thought to be the predominant endopeptidase activity. The primary eluted peptide (MRMATPLLMQALPM (SEQ ID NO: 28418) can be seen in FIG. 16 to be bracketed by the cathepsin S cleavage on both the N- and C-termini.

In addition to the invariant chain several additional peptides were also found loaded into the MHC II molecule (Chicz et al, vide infra). These peptides had "ragged" ends extending several amino acids in both the N-terminal and C-terminal side of the binding pocket. In each case the cleavage predictions matched the peptides that were detected.

The experiments described above with reference to CLIP showed a critical relationship between cathepsin cleavage and MHC presentation. The observations with MHC II were extended and shown to also be consistent with observations with respect to MHC I presentation of the shorter 9-mer peptides. Peptides presented on cell surfaces bound to MHC I molecules arise via proteasomal cleavages of protein molecules tagged for destruction in the cytoplasm. Resulting fragments produced in this part of the process are longer (up to about 20-mers) than can be accommodated in the binding pocket of MHC I molecules. These fragments are delivered to the MHC loading compartment by specialized molecular machinery called TAP (transporter associated antigen processing) where the resident peptidases trim the peptides to fit into the binding groove.

Example 5

Binding Characteristics and Cleavage of *Brucella melitensis* Methionine Sulphoxide Reductase A 9-mer peptide, RYCINSASL (SEQ ID NO: 28419) (RL9) from *Brucella melitensis* methionine sulphoxide reductase B has been found to be presented on MHC I molecules and produce populations of T-cells which recognize the pMHC complex (Durward, M. et al 2010 Infection and Immunity Discordant *Brucella melitensis* Antigens Yield Cognate CD8 T Cells In Vivo).

Figure 17:
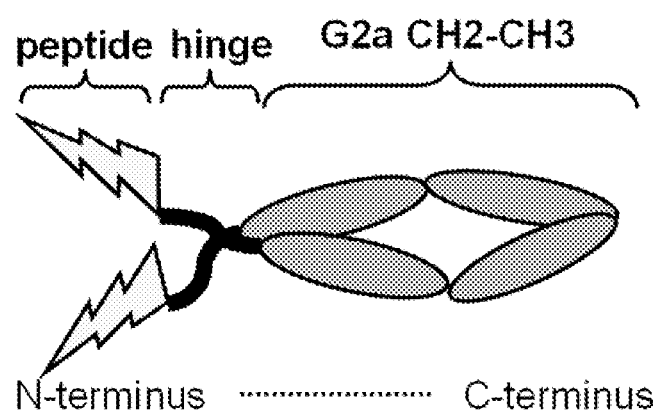
FIG. 17 shows a construct comprising an epitope peptide of interest at the N-terminus, the hinge region and the constant regions CH2 and CH3 from the murine IgG2a immunoglobulin. The molecule dimerizes via formation of disulphide bonds at the hinge.
Figure 18:
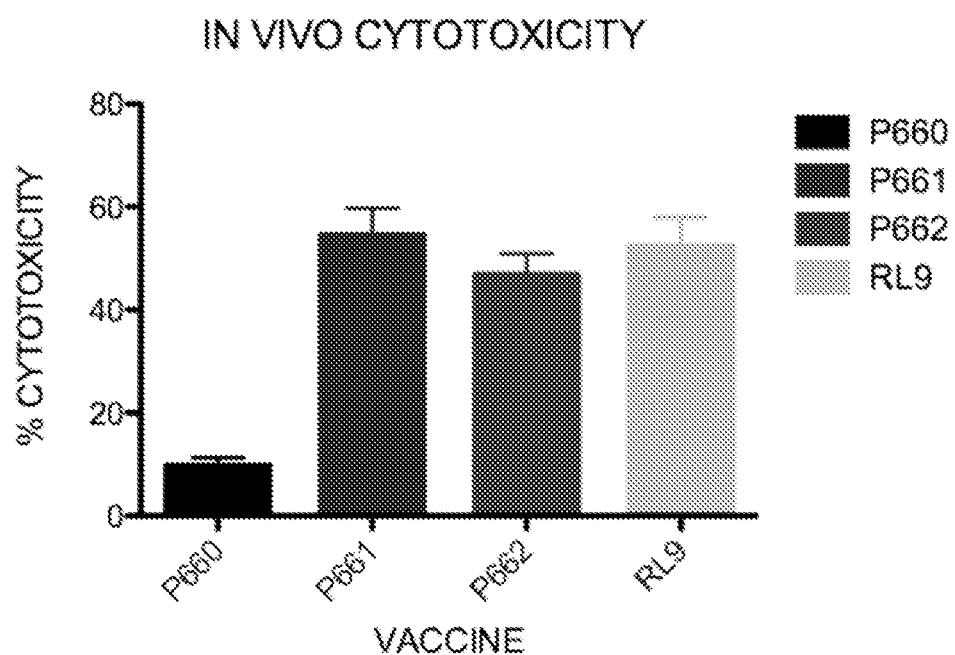
FIG. 18 shows the in vivo clearance of RL9 pulsed splenocytes in immunized mice. Mice were immunized and boosted once with affinity-purified RL-G2a(CH2-CH3) (P661) or RL-G2a(CH2-CH3)-RL (P662) or synthetic peptide RL9. One week after the boost, RL9-pulsed (labeled CFSEhi) and unpulsed (labeled CFSElo) splenocytes from naïve mice were adoptively transferred into the immunized mice via retrobulbar injection. Six hours post transfer, spleens were removed from immunized mice and analyzed for surviving pulsed, labeled target cells using flow cytometry. % specific lysis=1−[naive/vaccinated]×100; where r=% CFSELo cells÷% CFSEHi cells. P660=immunized with isotype-matching, irrelevant antibody.

Further to the studies published by Durward et at we showed that immunization of mice with the RL9 peptide leads to a protective response pattern in mice. We produced two versions of the RL-G2aFc molecule shown in FIG. 17, one with an N-terminal peptide fusion, the other with both N-terminal and C-terminal peptide fusions. Mice were immunized to test the two carrier proteins carrying known effective peptide (RL9). Mice immunized with the RL-G2a (CH2-CH3) or RL-G2a(CH2-CH3)-RL construct were able to reduce the number of RL9-pulsed target cells at a significantly higher rate than control immunized mice (FIG. 18) indicating that RL-G2a(CH2-CH3) vaccine induces a cellular cytotoxic response against target splenocytes displaying RL9 peptide, consistent with the protective response pattern known to eliminate *Brucella* infection. The data show the G2a(CH2-CH-3) carrier protein bearing the larger CEG peptide is correctly cleaved and RL9 peptide specific effector cells are created.

In view of the observations of the critical role of cathepsin cleavage in presentation of CLIP peptides, described in the Example 5 above, an experiment was designed to further examine the role of cathepsin in epitope definition.

Figure 19:
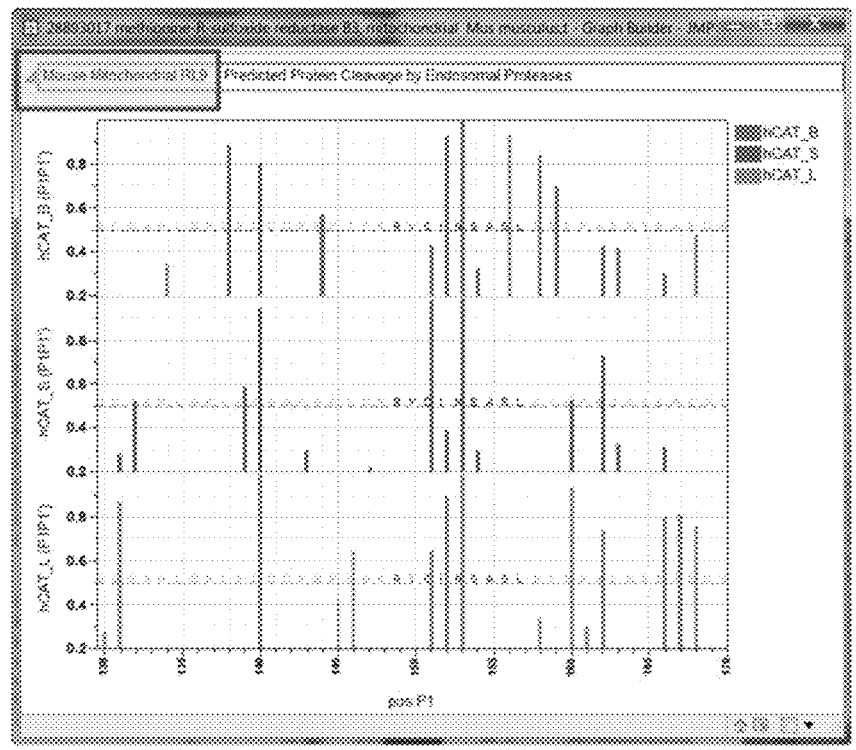
FIG. 19 shows the probability of cathepsin cleavage in methionine sulphoxide reductase B. Panel A shows the predicted cleavage of murine methionine sulphoxide reductase B. Panel B shows the probability of cleavage of Brucella melitensis methionine sulphoxide reductase B. In both panels the 9 mer peptide of interest RYCINSASL is shown.
Figure 19:
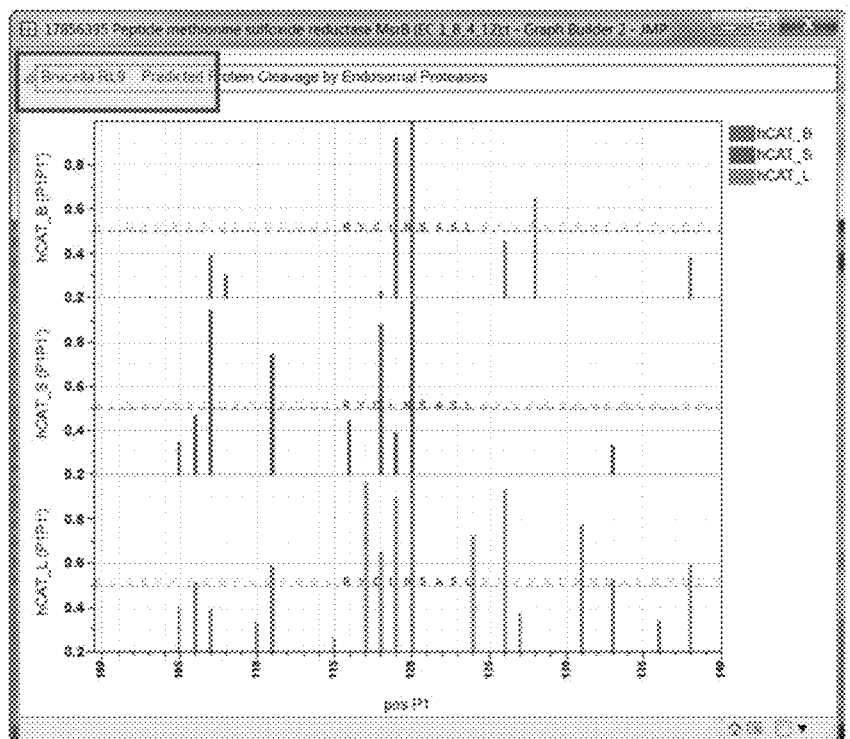

An interesting feature of the peptide identified, RYCINSASL (SEQ ID NO: 28419), is that it is derived from the active site of a metabolic enzyme widely distributed in nature. Mice contain the identical 9-mer peptide in their mitochondrial version of the enzyme. Thus, it would be expected that the mice would recognize the RYCINSASL (SEQ ID NO: 28419) peptide as "self" and not produce an immunological response. Nevertheless, mice infected with *B. melitensis* produce a profound immunological response to this peptide; it is not recognized as self. We noted that the flanking residues outside of the active site 9-mer are quite different between the murine endogenous and *B. melitensis* forms of the enzyme. The differences in amino acids in the flanking positions change the probability of the N- and C-terminal bonds being cleaved. In contrast to the peptide from *B. melitensis*, the peptide in the mouse mitochondrial enzyme is not predicted to be excised (FIG. 19).

In order to test this experimentally we replaced 6 amino acids on the N- and C-terminal side of the RL9 peptide in the *Brucella* enzyme to make it non-cleavable. This is shown in FIG. 20.

Cloning of *Brucella* RL(105-135) Peptides into mG2a Carrier

Existing wild-type *Brucella* RL(105-135) peptide cloned into p500695. The wt *Brucella* amino acid sequence contains cathepsin S cleavage sites upstream of the RL9 peptide as shown in SEQ ID NOS: 28412 and 28413.

Modified *Brucella* RL(105-135)mod peptide was cloned into mG2a carrier, this sequence has the RL9 flanking regions from *Brucella* replaced with murine flanking regions that are predicted to have no cathepsin S cleavage sites, the two flanking regions are marked in SEQ ID Nos.: 28415 AND 28416 and in FIG. 20.

Cloning procedure: The amino acid sequence encoding *Brucella melitensis* methionine sulfoxide reductase (Accession #NP_541797) position aa 105-135 was backtranslated using the Lasergene software (DNAstar, Madison, WI) built-in mammalian non-degenerate backtranslation code. Proper restriction enzyme sites were added to both ends of the RL(105-135) sequence and the nucleotide sequence was synthesized using a commercial vendor (IDT, Coralville, IA). The sequence for the modified RL(105-135)mod was similarly assembled in silico and then submitted for synthesis. The obtained synthesized RL(15-135) gene sequences are digested with the specific restriction sites and in-frame cloned upstream of the murine G2a (hinge-CH2-CH3)-containing retroviral expression retrovector.

In vivo testing: The expression retrovectors containing the RL(105-135) or RL(105-135)mod sequence were used to make stable CHO expression cell lines to produce both peptides as N-terminal murine IgG2a hinge-Fc portion. BR-RL(105-135)-mG2a and BR-RL(105-135)mod-mG2a is harvested from cell supernatant and used to immunize mice via subcutaneous injection at the tail at 25 ug/mouse dose and formulated with Sigma (S6322) and CpG adjuvants. One or two boosts are given after the first injection. One week after the last boost, splenocytes are collected from immunized mice and cultivated in vitro. Splenocytes from naïve mice are pulsed with synthesized RL9 or irrelevant control peptide and then added to the harvested effector cells. After a 5 h incubation, cells are harvested and monitored for T-cell phenotype (CD4, CD8, CD3), activation status (LFA-1) and intracellular cytokine (INFg) production using flow cytometry. This analysis will yield information as to whether the removal of a predicted cathepsin cleavage site changes processing of peptides upon uptake by antigen presenting cells and subsequent stimulation of T-cells.

It is anticipated that mice vaccinated with the modified peptide sequence will not display the peptide on the MHC I surface molecules nor generate a T-cell response.

Seq 1. BR-RL(105-135)-G2a(CH2-CH3)-BR-RL,
nucleotide sequence, ID:500695n (SEQ ID NO: 28420)
TTCCCCGACGGCCCCGTGGACCGCGGCGGCCTGCGCTACTGCATCAACT
CCGCCTCCCTGCGCTTCGTGCCCAAGGACCGCATGGAGGCCGAG -continued

```
1-93 BR-RL(105-135)
Seq. 2. BR-RL(105-135)-G2a(CH2-CH3)-BR-RL, amino
acid sequence, ID:500695p
                                    (SEQ ID NO: 28421)
FPDGPVDRGGLRYCINSASLRFVPKDRMEAE Seq. 3. BR-RL(105-135)mod-G2a(CH2-CH3)-BR-RL,
nucleotide sequence, ID:500695n
                                    (SEQ ID NO: 28422)
TTCCCCGACGGCCCTCCTCGTCCGACCGGCAAAAGATACTGCATCAACT
CAGCATCCTTGTCCTTCACTCCTGCAGACCGCATGGAGGCCGAG
```

| | |
|---|---|
| 1-15 | *Brucella* sequence |
| 16-33 | Murine sequence |
| 34-60 | *Brucella* RL9 peptide |
| 61-78 | Murine sequence |
| *79-93* | *Brucella sequence* |

```
Seq. 4. BR-RL(105-135)mod-G2a(CH2-CH3)-BR-RL,
amino acid sequence, ID:500695p
                                    (SEQ ID NO: 28423)
FPDGPPRPTGKRYCINSASLSFTPADRMEAE
```

| | |
|---|---|
| 1-5 | *Brucella* sequence |
| 6-11 | Murine sequence |
| 12-20 | *Brucella* RL9 peptide |
| 21-26 | Murine sequence |
| 27-31 | *Brucella* sequence |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A process of identifying variant cancer cell epitopes that bind to an MHC binding region and producing a vaccine comprising:

a) obtaining amino acid sequences for a cancer cell protein;

b) providing peptide binding prediction equations for multiple MHC binding regions derived by:

(i) assembling experimentally derived data comprising a multiplicity of measurements of amino acid physicochemical properties;

(ii) producing a correlation matrix of the experimentally derived data;

(iii) deriving by Principal Component Analysis multiple uncorrelated dimensionless, weighted and ranked proxy descriptors to describe at least 80% of the variance in said physicochemical properties of individual amino acids, (iv) using said proxy descriptors to describe individual amino acids in peptides with known binding affinities thereby creating vectors which describe said peptides with known binding affinities, and (v) via neural network modeling, deriving said binding prediction equations by comparing said vectors with said known binding affinities of said peptides;

(c) in-putting said amino acid sequences from said cancer cell protein into a computer;

(d) identifying peptides of interest in said cancer cell protein, wherein the peptides of interest are suspected cancer cell epitopes, and determining the binding affinity of the peptides of interest by applying the MHC binding prediction equations;

(e) generating in silico at least 1000 variants of the peptides of interest by substituting individual amino acids of the peptides with a different amino acid;

(f) applying proxy descriptors derived from the Principal Component Analysis of step (b) to describe each of the variant peptides generated in step (e) and applying the MHC binding prediction equations of step (b) to each of the variant peptides to determine the predicted MHC binding of each variant peptide;

(g) comparing the predicted binding to an MHC binding region of each of the variant peptides generated in step (e) with the binding affinity of the peptides of interest in the cancer protein to identify variant peptide sequences with higher or lower predicted binding affinity to said MHC binding region;

(h) synthesizing one or more of said variant peptide sequences which are identified as having a higher or lower predicted binding affinity to said MHC binding region;

(i) formulating the synthesized peptides with a pharmaceutical carrier to provide a vaccine, and (j) administering the vaccine to a subject that has cancer under conditions such that an immune response is generated.

2. The process of claim 1 wherein said synthesized peptide is identified as having higher or lower binding affinity to more than one binding partner.

SEQUENCE LISTING

The patent contains a lengthy sequence listing. A copy of the sequence listing is available in electronic form from the USPTO web site (https://seqdata.uspto.gov/?pageRequest=docDetail&DocID=US12374421B2). An electronic copy of the sequence listing will also be available from the USPTO upon request and payment of the fee set forth in 37 CFR 1.19(b)(3).

3. The process of claim 1, wherein said binding affinity of said variant peptide sequence is increased as compared to the binding affinity of the peptide of interest in the cancer protein.

4. The process of claim 1, wherein said binding affinity of said variant peptide sequence is decreased as compared to the binding affinity of the peptide of interest in the cancer protein.

5. The process of claim 1, wherein said binding affinity of the variant peptide sequence is increased or decreased by >1 standard deviation units.

6. The process of claim 1, wherein said binding affinity of the variant peptide sequence is increased or decreased by >2 standard deviation units.

7. The process of claim 1, wherein from about 10 to about 100 peptide sequences are selected for synthesis.

8. The process of claim 1, wherein at least 2 amino acids of said synthesized peptide sequence are modified.

9. The process of claim 1, wherein from 1,000 to about 5,000 variant peptide sequences are generated in step (e).

10. The process of claim 1, wherein from about 5,000 to about 10,000 variant peptide sequences are generated in step (e).

11. The process of claim 1, wherein from about 1 to about 10 peptide sequences are selected for synthesis in step (h).

\* \* \* \* \*